United States Patent
Blain et al.

(10) Patent No.: US 8,992,533 B2
(45) Date of Patent: Mar. 31, 2015

(54) VERTEBRAL FACET JOINT DRILL AND METHOD OF USE

(75) Inventors: Jason Blain, Encinitas, CA (US); Eric Kovach, Carlsbad, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 403 days.

(21) Appl. No.: 12/859,009

(22) Filed: Aug. 18, 2010

(65) Prior Publication Data

US 2011/0040301 A1 Feb. 17, 2011

Related U.S. Application Data

(63) Continuation-in-part of application No. 12/035,366, filed on Feb. 21, 2008.

(60) Provisional application No. 60/891,159, filed on Feb. 22, 2007.

(51) Int. Cl.
*A61B 17/00* (2006.01)
*A61B 17/16* (2006.01)
*A61B 17/56* (2006.01)
*A61B 17/70* (2006.01)

(52) U.S. Cl.
CPC ......... *A61B 17/1608* (2013.01); *A61B 17/1642* (2013.01); *A61B 17/1671* (2013.01); *A61B 17/562* (2013.01); *A61B 17/7064* (2013.01)
USPC ............................................. 606/80; 606/79

(58) Field of Classification Search
CPC .................................................. A61B 17/7064
USPC ............................................. 606/80, 180, 79
See application file for complete search history.

(56) References Cited

U.S. PATENT DOCUMENTS

| | | | |
|---|---|---|---|
| 86,016 | A | 1/1869 | Howell |
| 1,822,280 | A | 9/1931 | Ervay |
| 1,822,330 | A | 9/1931 | Ainslie |
| 3,111,945 | A | 11/1963 | Von Solbrig |
| 3,867,728 | A | 2/1975 | Stubstad et al. |
| 3,875,595 | A | 4/1975 | Froning |

(Continued)

FOREIGN PATENT DOCUMENTS

| | | |
|---|---|---|
| CA | 2437575 | 4/2009 |
| DE | 9304368 | 5/1993 |

(Continued)

OTHER PUBLICATIONS

CurvTek Bone Tunneling System surgical tecnhique; Arthrotek; Biomet; 2000.*

(Continued)

*Primary Examiner* — David Bates
(74) *Attorney, Agent, or Firm* — Knobbe, Martens, Olson & Bear, LLP

(57) ABSTRACT

Devices and methods for creating lumens in the articular process of the vertebra are provided. An embodiment of the invention can be a tool that can cut a curved lumen through the articular process. The tool can have a lumen-forming arm with a rotating drill contained within that can be powered by a drill motor. The lumen-forming arm can be axially translated to cut a path through the articular process. Methods of using the resulting lumens to anchor or stabilize facet joint prosthesis, and also altering the spacing and motion at the facet joints of the vertebral column, are provided.

19 Claims, 82 Drawing Sheets

(56) References Cited

U.S. PATENT DOCUMENTS

| | | |
|---|---|---|
| 3,879,767 A | 4/1975 | Stubstad |
| 4,001,896 A | 1/1977 | Arkangel |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,231,121 A | 11/1980 | Lewis |
| 4,312,337 A | 1/1982 | Donohue |
| 4,349,921 A | 9/1982 | Kuntz |
| 4,502,161 A | 3/1985 | Wall |
| 4,535,764 A | 8/1985 | Ebert |
| 4,634,445 A | 1/1987 | Helal |
| 4,662,371 A | 5/1987 | Whipple et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,863,477 A | 9/1989 | Monson |
| 4,904,260 A | 2/1990 | Ray et al. |
| 4,907,577 A | 3/1990 | Wu |
| 4,911,718 A | 3/1990 | Lee et al. |
| 4,919,667 A | 4/1990 | Richmond |
| 4,936,848 A | 6/1990 | Bagby |
| 4,941,466 A | 7/1990 | Romano |
| 4,969,909 A | 11/1990 | Barouk |
| 5,000,165 A | 3/1991 | Watanabe |
| 5,002,546 A | 3/1991 | Romano |
| 5,015,255 A | 5/1991 | Kuslich |
| 5,047,055 A | 9/1991 | Hao et al. |
| 5,062,845 A | 11/1991 | Kuslich et al. |
| 5,071,437 A | 12/1991 | Steffee |
| 5,092,866 A | 3/1992 | Breard et al. |
| 5,112,346 A | 5/1992 | Hiltebrandt et al. |
| 5,127,912 A | 7/1992 | Ray et al. |
| 5,147,404 A | 9/1992 | Downey |
| 5,171,280 A | 12/1992 | Baumgartner |
| 5,192,326 A | 3/1993 | Bao et al. |
| 5,209,755 A | 5/1993 | Abrahan et al. |
| 5,258,031 A | 11/1993 | Salib et al. |
| 5,300,073 A | 4/1994 | Ray et al. |
| 5,306,275 A | 4/1994 | Bryan |
| 5,306,308 A | 4/1994 | Gross et al. |
| 5,306,309 A | 4/1994 | Wagner et al. |
| 5,330,479 A | 7/1994 | Whitmore |
| 5,360,431 A | 11/1994 | Puno et al. |
| 5,368,596 A | 11/1994 | Brookhart |
| 5,370,697 A | 12/1994 | Baumgartner |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,462,542 A | 10/1995 | Alesi, Jr. |
| 5,487,756 A | 1/1996 | Kallesoe et al. |
| 5,491,882 A | 2/1996 | Walston et al. |
| 5,496,318 A | 3/1996 | Howland et al. |
| 5,507,823 A | 4/1996 | Walston et al. |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,545,229 A | 8/1996 | Parsons et al. |
| 5,549,619 A | 8/1996 | Peters et al. |
| 5,556,431 A | 9/1996 | Buttner-Janz |
| 5,562,738 A | 10/1996 | Boyd et al. |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |
| 5,586,989 A | 12/1996 | Bray, Jr. |
| 5,591,165 A | 1/1997 | Jackson |
| 5,603,713 A | 2/1997 | Aust et al. |
| 5,638,700 A | 6/1997 | Shechter |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,716,415 A | 2/1998 | Steffee |
| 5,725,582 A | 3/1998 | Bevan et al. |
| 5,741,260 A | 4/1998 | Songer et al. |
| 5,741,261 A | 4/1998 | Moskovitz et al. |
| 5,766,251 A | 6/1998 | Koshino |
| 5,766,253 A | 6/1998 | Brosnahan |
| 5,772,663 A | 6/1998 | Whiteside et al. |
| 5,797,916 A | 8/1998 | McDowell |
| 5,824,093 A | 10/1998 | Ray et al. |
| 5,824,094 A | 10/1998 | Serh an et al. |
| 5,836,948 A | 11/1998 | Zucherman et al. |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,879,396 A | 3/1999 | Walston et al. |
| 5,888,203 A | 3/1999 | Goldberg |
| 5,893,889 A | 4/1999 | Harrington |
| 5,895,428 A | 4/1999 | Berry |
| RE36,221 E | 6/1999 | Breard et al. |
| 5,951,555 A | 9/1999 | Rehak et al. |
| 5,997,542 A | 12/1999 | Burke |
| 6,001,130 A | 12/1999 | Bryan et al. |
| 6,014,588 A | 1/2000 | Fitz |
| 6,019,763 A | 2/2000 | Nakamura et al. |
| 6,019,792 A | 2/2000 | Cauthen |
| 6,039,763 A | 3/2000 | Shelokov |
| 6,048,342 A | 4/2000 | Zucherman et al. |
| 6,050,998 A | 4/2000 | Fletcher |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,099,531 A | 8/2000 | Bonutti |
| 6,106,558 A | 8/2000 | Picha |
| 6,113,637 A | 9/2000 | Gill et al. |
| 6,132,464 A | 10/2000 | Martin |
| 6,132,465 A | 10/2000 | Ray et al. |
| 6,146,422 A | 11/2000 | Lawson |
| 6,156,067 A | 12/2000 | Bryan et al. |
| 6,179,839 B1 | 1/2001 | Weiss et al. |
| D439,340 S | 3/2001 | Michelson |
| 6,200,322 B1 | 3/2001 | Branch et al. |
| 6,293,949 B1 | 9/2001 | Justis et al. |
| D450,122 S | 11/2001 | Michelson |
| 6,368,325 B1 | 4/2002 | McKinley et al. |
| 6,368,350 B1 | 4/2002 | Erickson et al. |
| 6,375,573 B2 * | 4/2002 | Romano .................. 464/58 |
| 6,379,386 B1 | 4/2002 | Resch et al. |
| 6,419,678 B1 | 7/2002 | Asfora |
| 6,419,703 B1 | 7/2002 | Fallin et al. |
| 6,436,101 B1 | 8/2002 | Hamada et al. |
| 6,470,207 B1 | 10/2002 | Simon et al. |
| 6,565,605 B2 | 5/2003 | Goble et al. |
| 6,572,617 B1 | 6/2003 | Senegas |
| 6,579,318 B2 | 6/2003 | Varga et al. |
| 6,579,319 B2 | 6/2003 | Goble et al. |
| 6,589,244 B1 | 7/2003 | Sevrain et al. |
| 6,600,956 B2 | 7/2003 | Maschino et al. |

(56) References Cited

U.S. PATENT DOCUMENTS

| | | |
|---|---|---|
| 6,607,530 B1 | 8/2003 | Carl et al. |
| 6,610,091 B1 | 8/2003 | Reiley |
| 6,626,944 B1 | 9/2003 | Taylor |
| 6,669,697 B1 | 12/2003 | Pisharodi |
| 6,669,729 B2 | 12/2003 | Chin |
| 6,706,068 B2 | 3/2004 | Ferree |
| 6,743,232 B2 | 6/2004 | Overaker et al. |
| 6,761,720 B1 | 7/2004 | Senegas |
| 6,764,491 B2 | 7/2004 | Frey et al. |
| 6,770,095 B2 | 8/2004 | Grinberg et al. |
| 6,783,527 B2 | 8/2004 | Drewry et al. |
| 6,790,210 B1 | 9/2004 | Cragg et al. |
| 6,811,567 B2 | 11/2004 | Reiley |
| 6,902,566 B2 | 6/2005 | Zucherman et al. |
| 6,908,484 B2 | 6/2005 | Zubok et al. |
| 6,966,930 B2 | 11/2005 | Arnin et al. |
| 6,974,478 B2 | 12/2005 | Reiley et al. |
| 6,974,479 B2 | 12/2005 | Trieu |
| D517,404 S | 3/2006 | Schluter |
| 7,008,429 B2 | 3/2006 | Goldbek |
| 7,013,675 B2 | 3/2006 | Marquez-Pickering |
| 7,051,451 B2 | 5/2006 | Augostino et al. |
| 7,074,238 B2 | 7/2006 | Stinson et al. |
| 7,101,375 B2 | 9/2006 | Zucherman et al. |
| 7,223,269 B2 | 5/2007 | Chappuis |
| D565,180 S | 3/2008 | Liao |
| 7,371,238 B2 | 5/2008 | Sololeski et al. |
| 7,458,981 B2 | 12/2008 | Fielding et al. |
| 7,517,358 B2 | 4/2009 | Petersen |
| 7,537,611 B2 | 5/2009 | Lee |
| 7,559,940 B2 | 7/2009 | McGuire et al. |
| 7,563,286 B2 | 7/2009 | Gerber et al. |
| 7,608,104 B2 | 10/2009 | Yuan et al. |
| 7,799,077 B2 | 9/2010 | Lang et al. |
| 7,806,895 B2 | 10/2010 | Weier et al. |
| 7,846,183 B2 | 12/2010 | Blain |
| 7,862,590 B2 | 1/2011 | Lim et al. |
| 7,935,136 B2 | 5/2011 | Alamin et al. |
| 7,993,370 B2 | 8/2011 | Jahng |
| 7,998,172 B2 | 8/2011 | Blain |
| 8,163,016 B2 | 4/2012 | Linares |
| 8,192,468 B2 | 6/2012 | Biedermann et al. |
| 8,216,275 B2 | 7/2012 | Fielding et al. |
| 8,246,655 B2 | 8/2012 | Jackson et al. |
| 8,394,125 B2 | 3/2013 | Assell et al. |
| 8,652,137 B2 | 2/2014 | Blain et al. |
| 8,740,942 B2 | 6/2014 | Blain |
| 8,740,949 B2 | 6/2014 | Blain |
| 8,858,597 B2 | 10/2014 | Blain |
| 8,882,804 B2 | 11/2014 | Blain |
| 2001/0018614 A1 | 8/2001 | Bianchi |
| 2002/0018799 A1 | 2/2002 | Spector et al. |
| 2002/0019637 A1 | 2/2002 | Frey et al. |
| 2002/0029039 A1 | 3/2002 | Zucherman et al. |
| 2002/0040227 A1 | 4/2002 | Harari |
| 2002/0065557 A1 | 5/2002 | Goble et al. |
| 2002/0072800 A1 | 6/2002 | Goble et al. |
| 2002/0077700 A1 | 6/2002 | Varga et al. |
| 2002/0086047 A1 | 7/2002 | Mueller et al. |
| 2002/0120335 A1 | 8/2002 | Angelucci et al. |
| 2002/0123806 A1 | 9/2002 | Reiley |
| 2002/0151895 A1 | 10/2002 | Soboleski et al. |
| 2002/0173800 A1 | 11/2002 | Dreyfuss et al. |
| 2002/0173813 A1 | 11/2002 | Peterson et al. |
| 2002/0198527 A1 | 12/2002 | Muckter |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0187454 A1 | 10/2003 | Gill et al. |
| 2003/0191532 A1 | 10/2003 | Goble et al. |
| 2003/0204259 A1 | 10/2003 | Goble et al. |
| 2003/0216669 A1 | 11/2003 | Lang et al. |
| 2003/0233146 A1 | 12/2003 | Grinberg et al. |
| 2004/0006391 A1 | 1/2004 | Reiley |
| 2004/0010318 A1 | 1/2004 | Ferree |
| 2004/0024462 A1 | 2/2004 | Ferree et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0087954 A1 | 5/2004 | Allen et al. |
| 2004/0116927 A1 | 6/2004 | Graf |
| 2004/0127989 A1 | 7/2004 | Dooris et al. |
| 2004/0143264 A1 | 7/2004 | McAfee |
| 2004/0176844 A1 | 9/2004 | Zubok et al. |
| 2004/0215341 A1 | 10/2004 | Sybert et al. |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0015146 A1 | 1/2005 | Louis et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serh an et al. |
| 2005/0059972 A1 | 3/2005 | Biscup |
| 2005/0131409 A1* | 6/2005 | Chervitz et al. ............... 606/61 |
| 2005/0131538 A1 | 6/2005 | Chervitz et al. |
| 2005/0143818 A1* | 6/2005 | Yuan et al. ............. 623/17.11 |
| 2005/0159746 A1 | 7/2005 | Grab et al. |
| 2005/0177240 A1 | 8/2005 | Blain |
| 2005/0197700 A1 | 9/2005 | Boehem et al. |
| 2005/0251256 A1 | 11/2005 | Reiley |
| 2005/0256494 A1 | 11/2005 | Datta |
| 2006/0004367 A1* | 1/2006 | Alamin et al. ............... 606/74 |
| 2006/0036323 A1 | 2/2006 | Carl et al. |
| 2006/0041311 A1 | 2/2006 | McLeer |
| 2006/0084985 A1 | 4/2006 | Kim |
| 2006/0085072 A1 | 4/2006 | Funk et al. |
| 2006/0111782 A1 | 5/2006 | Petersen |
| 2006/0149375 A1 | 7/2006 | Yuan et al. |
| 2006/0200137 A1 | 9/2006 | Soboleski et al. |
| 2006/0241601 A1 | 10/2006 | Trautwein et al. |
| 2006/0241758 A1 | 10/2006 | Peterman et al. |
| 2006/0293691 A1 | 12/2006 | Mitra et al. |
| 2007/0055236 A1 | 3/2007 | Hudgins et al. |
| 2007/0078464 A1 | 4/2007 | Jones et al. |
| 2007/0118218 A1 | 5/2007 | Hooper |
| 2007/0149976 A1 | 6/2007 | Hale et al. |
| 2007/0179619 A1 | 8/2007 | Grab |
| 2007/0250166 A1 | 10/2007 | McKay |
| 2008/0183211 A1 | 7/2008 | Lamborne et al. |
| 2008/0208249 A1 | 8/2008 | Blain et al. |
| 2008/0228225 A1 | 9/2008 | Trautwein et al. |
| 2008/0287996 A1 | 11/2008 | Soholeski et al. |
| 2009/0018662 A1 | 1/2009 | Pasquet et al. |
| 2009/0024166 A1 | 1/2009 | Carl et al. |
| 2009/0076617 A1 | 3/2009 | Ralph et al. |
| 2009/0125066 A1 | 5/2009 | Kraus et al. |
| 2009/0138048 A1 | 5/2009 | Baccelli et al. |
| 2009/0264928 A1 | 10/2009 | Blain |
| 2009/0264929 A1 | 10/2009 | Alamin et al. |
| 2009/0270918 A1 | 10/2009 | Attia et al. |
| 2010/0234894 A1 | 9/2010 | Alamin et al. |
| 2010/0274289 A1 | 10/2010 | Carls et al. |
| 2010/0318133 A1 | 12/2010 | Tornier |
| 2011/0082503 A1 | 4/2011 | Blain |
| 2011/0098816 A1 | 4/2011 | Jacob et al. |
| 2011/0313456 A1 | 12/2011 | Blain |
| 2012/0101502 A1 | 4/2012 | Kartalian et al. |
| 2012/0150231 A1 | 6/2012 | Alamin et al. |
| 2012/0221048 A1 | 8/2012 | Blain |
| 2012/0221049 A1 | 8/2012 | Blain |
| 2012/0271354 A1 | 10/2012 | Baccelli et al. |
| 2012/0310244 A1 | 12/2012 | Blain et al. |
| 2013/0245693 A1 | 9/2013 | Blain |
| 2014/0228883 A1 | 8/2014 | Blain |

(56) References Cited

U.S. PATENT DOCUMENTS

| | | | |
|---|---|---|---|
| 2014/0257397 A1 | 9/2014 | Akbarnia et al. |
| 2014/0277142 A1 | 9/2014 | Blain |
| 2014/0277148 A1 | 9/2014 | Blain |

FOREIGN PATENT DOCUMENTS

| | | |
|---|---|---|
| DE | 20112123 | 10/2001 |
| DE | 10135771 | 2/2003 |
| EP | 0322334 | 6/1989 |
| EP | 0392124 | 10/1990 |
| EP | 0610837 | 8/1994 |
| EP | 1 201 202 | 5/2002 |
| EP | 1 201 256 | 5/2002 |
| FR | 2722980 | 2/1996 |
| GB | 2 366 736 | 3/2002 |
| JP | 08502668 | 3/1996 |
| JP | 10179622 | 7/1998 |
| JP | 2007503884 | 3/2007 |
| JP | 2007518524 | 7/2007 |
| JP | 2007-521881 | 8/2007 |
| MX | PA6012309 | 1/2007 |
| WO | WO 93/14721 | 8/1993 |
| WO | WO 94/04088 | 3/1994 |
| WO | WO 98/48717 | 11/1998 |
| WO | WO 99/23963 | 5/1999 |
| WO | WO 00/38582 | 7/2000 |
| WO | WO 00/53126 | 9/2000 |
| WO | WO 01/30248 | 5/2001 |
| WO | WO 02/065954 | 8/2002 |
| WO | WO 02/096300 | 12/2002 |
| WO | WO 03/101350 | 12/2003 |
| WO | WO 2004/071358 | 8/2004 |
| WO | WO 2005/020850 | 3/2005 |
| WO | WO 2005/072661 | 8/2005 |

OTHER PUBLICATIONS

King et al. Mechanism of Spinal Injury Due to Caudocephalad Acceleration, *Orthop. Clin. North Am.*, 6:19 1975.
Jul. 10, 2008 International Search report and Written Opinion for Application No. PCT/US2008/054607, filed Feb. 21, 2008.
International Search Report, International Application No. PCT/US2011/047432, mailed Dec. 12, 2011.
3rd Party lab notebook, 2 pages, dated May 20, 2003.
E-mail from 3rd party citing U.S. Appl. No. 60/721,909; U.S. Appl. No. 60/750,005 and U.S. Appl. No. 60/749,000.
PARTEQ Innovations, "Facet Joint Implants & Resurfacing Devices," Technology Opportunity Bulletin, Tech ID 1999-012.
Dec. 5, 2006 Int'l Search Report for App. No. PCT/US2005/003753 filed Feb. 4, 2005.
Mar. 10, 2008 European Examination Report for European App. No. EP05712981 filed Feb. 4, 2005.
Apr. 6, 2009 European Examination Report for European App. No. EP05712981 filed Feb. 4, 2005.
Dec. 15, 2009 First Official Report for Australian App No. 2005213459, filed Feb. 4, 2005.
Dec. 15, 2010 Second Official Report for Australian App No. 2005213459, filed Feb. 4, 2005.
Jun. 15, 2010 Examination Report for related European App. No. EP05712981, filed Feb. 4, 2005.
May 25, 2010 Notice of Reasons for Rejection for Japanese App No. 2006-552309, filed Feb. 4, 2005.
Feb. 15, 2011 Decision of Rejection for Japanese App No. 2006-552309, filed Feb. 4, 2005.
Feb. 15, 2011 Notice of Reasons for Rejection for Japanese App No. 2010-221380 filed Feb. 4, 2005.
Sep. 2, 2011 Office Action for Canadian App No. 2555355.
Mar. 14, 2011 Partial European Search Report for App No. EP 10 17 8979 filed on Feb. 4, 2005.
Jul. 24, 2007 Supp Partial European Search Report for European App No. EP 05712981.
Int'l Preliminary Report on Patentability for PCT App. No. PCT/US2004/028094 (WO 05/020850) filed Aug. 27, 2004.
Int'l Preliminary Report on Patentability for PCT App. No. PCT/US2005/000987 (WO 05/072661) filed Jan. 13, 2005.
Int'l Search Report for PCT App. No. PCT/CA2002/00193 (WO 02/065954) filed Feb. 15, 2002.
Int'l Search Report for related PCT App. No. PCT/US2005/000987 (WO 05/072661) filed Jan. 13, 2005.
Oct. 21, 2013 Office Action for U.S. Appl. No. 13/221,185, filed Aug. 30, 2011.
Oct. 8, 2013 Notice of Allowance for U.S. Appl. No. 12/035,366, filed Feb. 21, 2008.
Nov. 8, 2013 Office Action for related U.S. Appl. No. 12/960,309, filed Dec. 3, 2010.
May 30, 2012 Int'l Search Report and Written Opinion for Int'l App. No. PCT/US2012/026470.
Jun. 20, 2012 Int'l Search Report and Written Opinion for Int'l App. No. PCT/US2012/026472.
Official Communication in Australian Application No. AU2013237744, dated Sep. 2, 2014.
Official Communication in Canadian Application No. 2,803,783, dated Sep. 29, 2014.
Official Communication in European Application No. 14175088.5, dated Sep. 8, 2014.
Official Communication in European Application No. 14177951.2, dated Nov. 13, 2014.
Official Communication in European Application No. 11818586.7, dated Nov. 6, 2014.
Official Communication in Japanese Application No. 2012-272106, dated Dec. 3, 2013.
Official Communication in Japanese Application No. 2012-272106, dated May 26, 2014.
Official Communication in Australian Application No. 2011292297, dated Jul. 10, 2013.
International Preliminary Report on Patentability in International Application No. PCT/US2011/047432, dated Feb. 28, 2013.
International Preliminary Report on Patentability and Written Opinion in International Application No. PCT/US2012/026470, dated Sep. 6, 2013.
International Preliminary Report on Patentability and Written Opinion in International Application No. PCT/US2012/026472, dated Mar. 20, 2014.
International Search Report and Written Opinion in International Application No. PCT/US2014/019325, dated Jun. 17, 2014.

\* cited by examiner

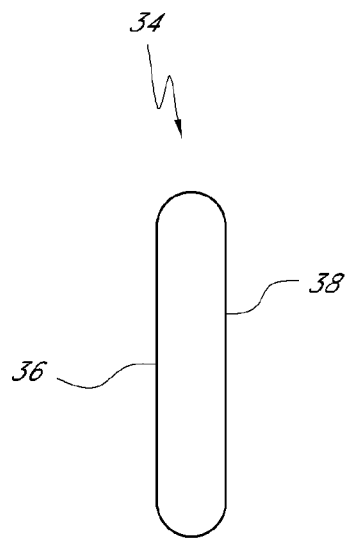
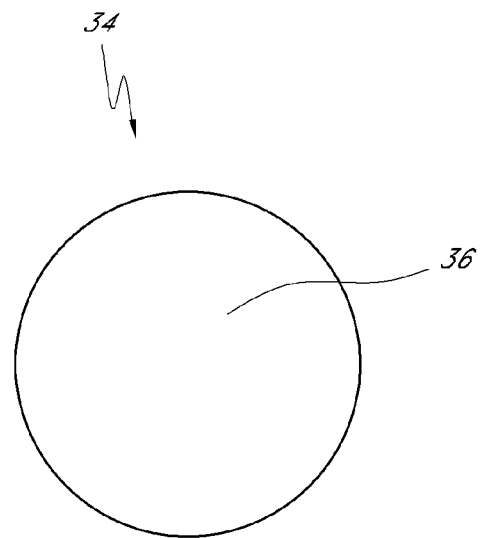
*FIG. 7A*  *FIG. 7B*
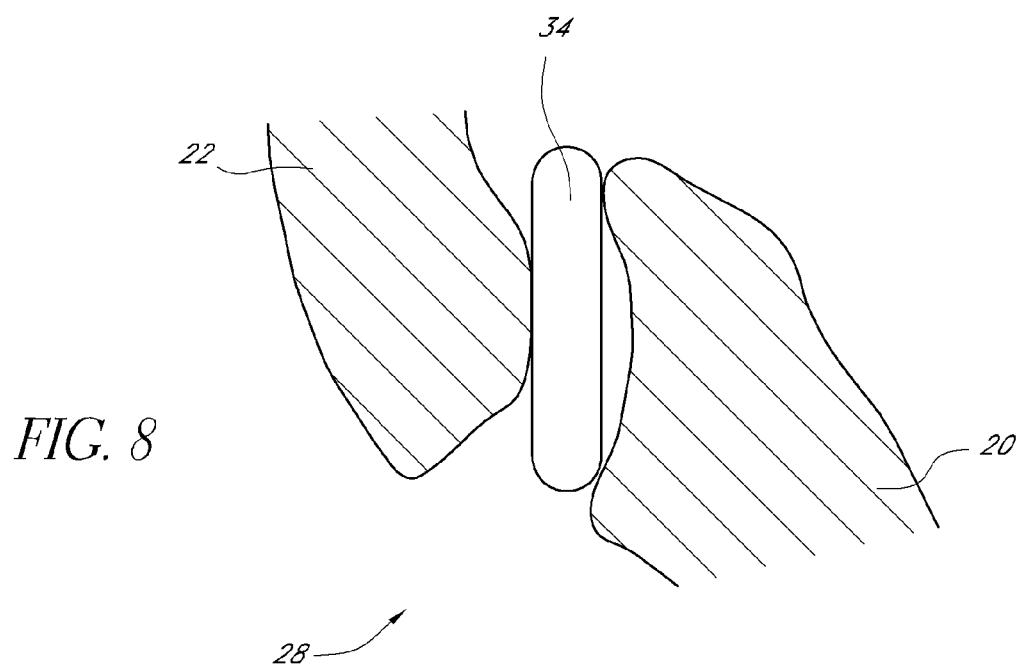
*FIG. 8*

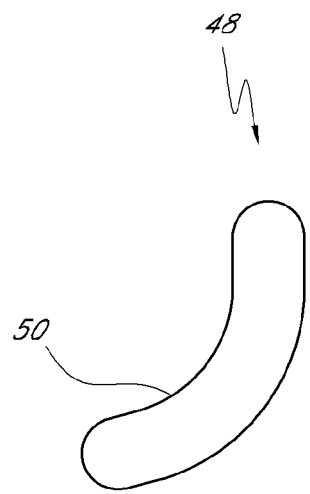
*FIG. 12A*
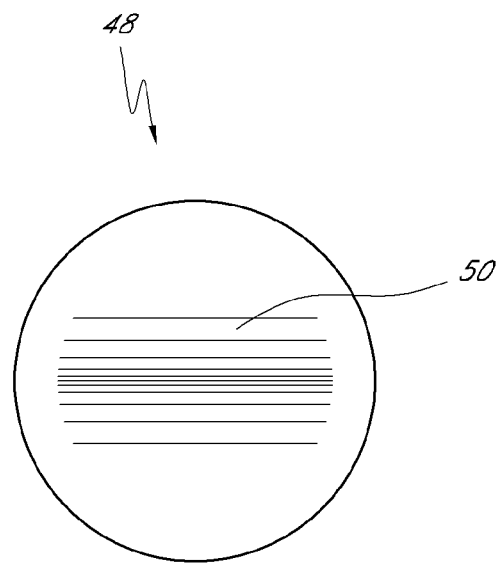
*FIG. 12B*
*FIG. 13*
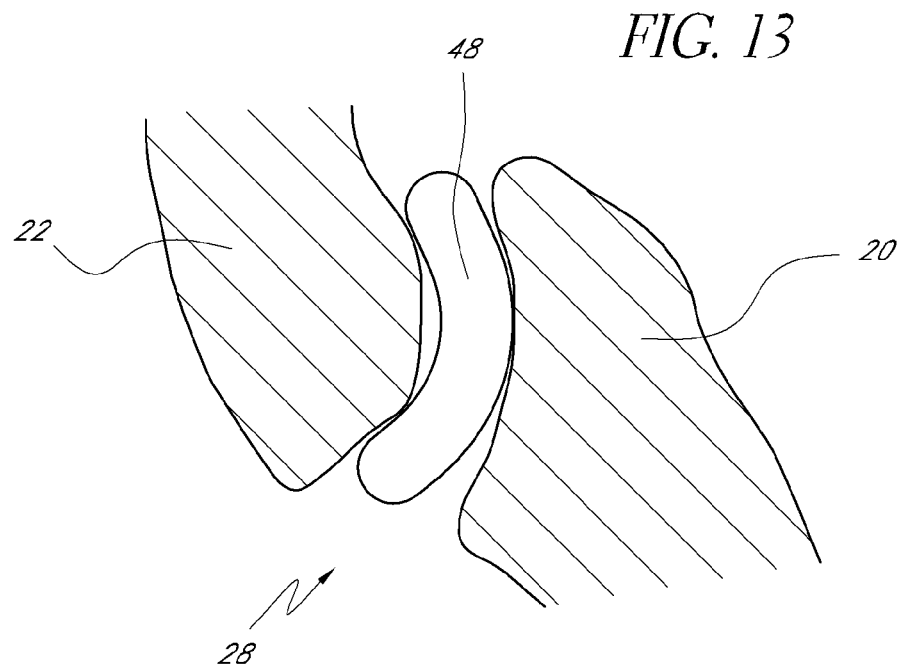

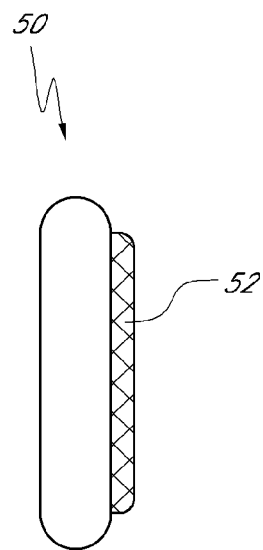
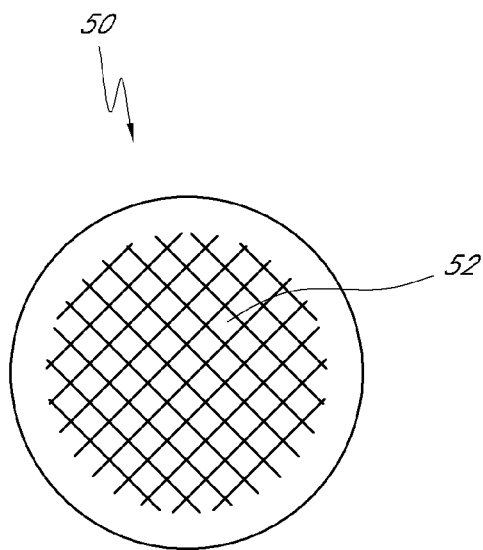
FIG. 14A                                    FIG. 14B
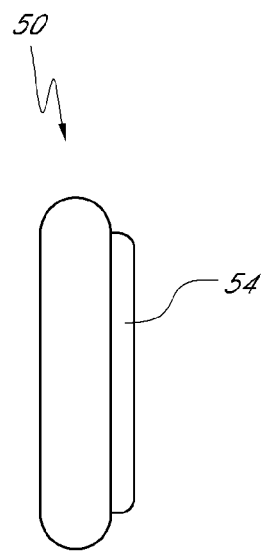
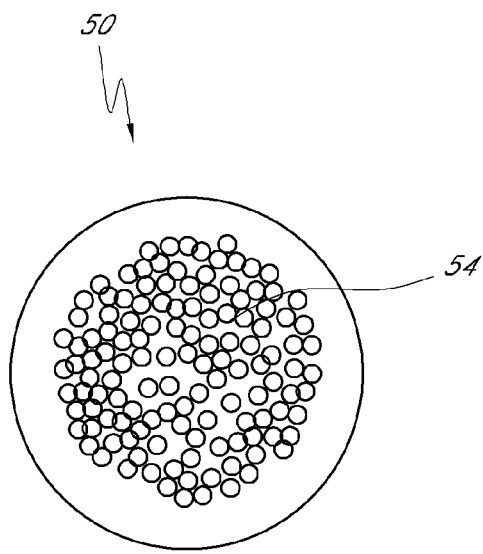
FIG. 15A                                    FIG. 15B

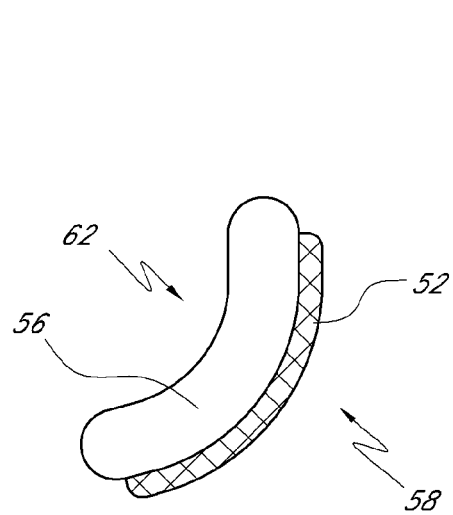
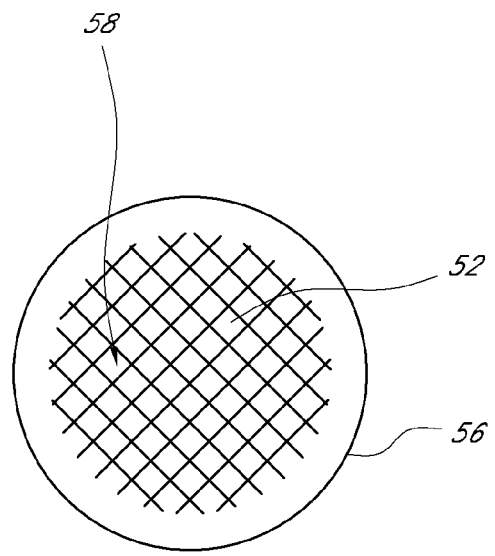
FIG. 16A  FIG. 16B
FIG. 17
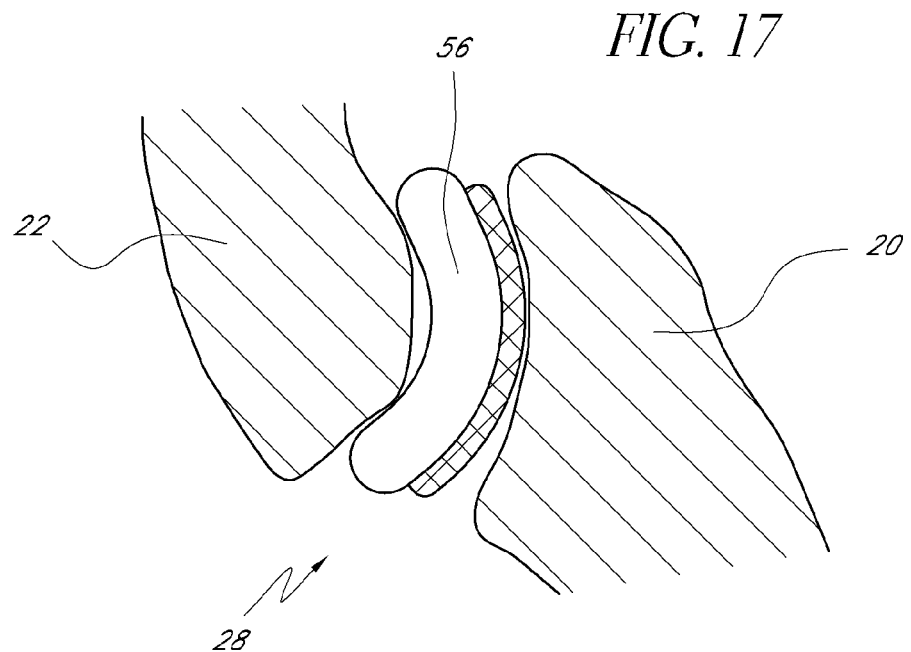

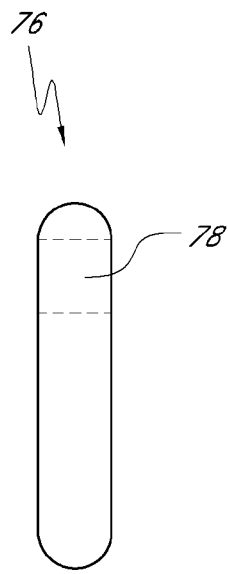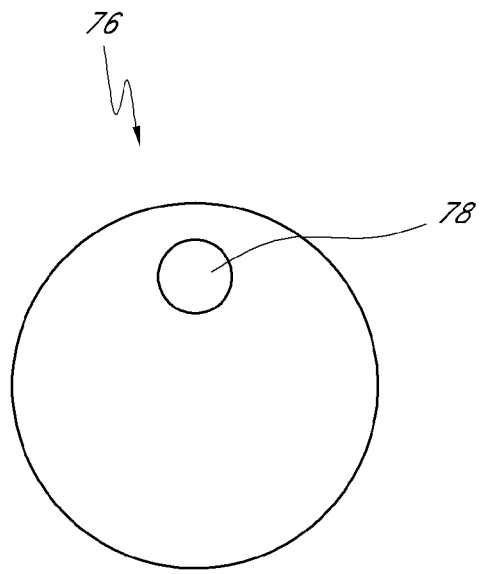
FIG. 22A               FIG. 22B
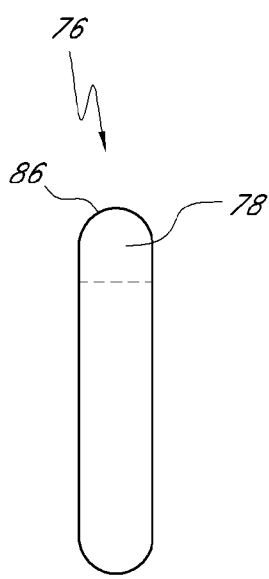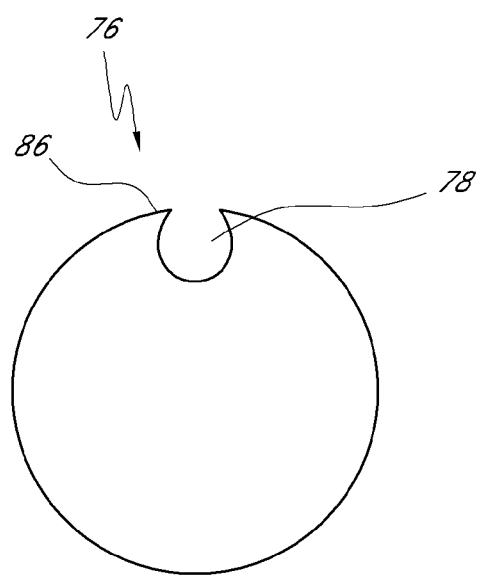
FIG. 23A               FIG. 23B

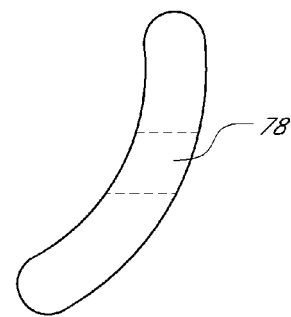 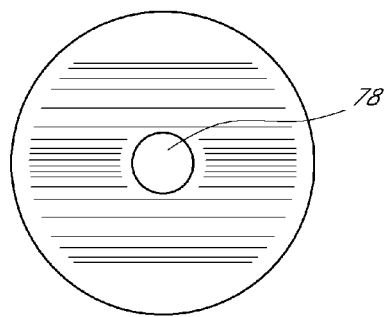
FIG. 25A  FIG. 25B
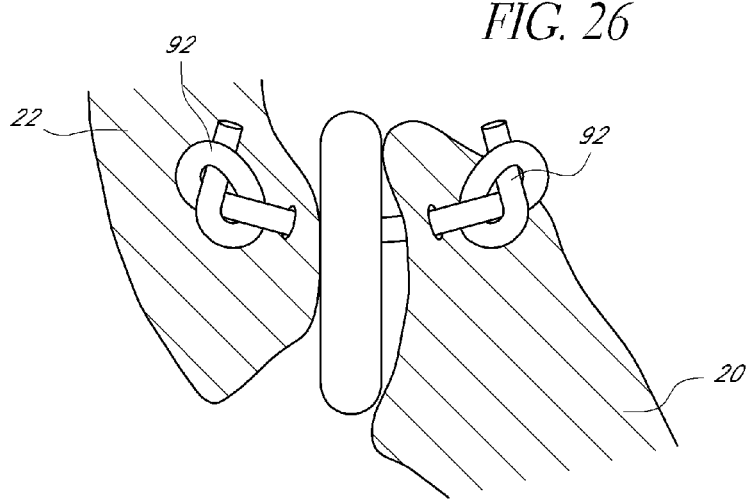
FIG. 26

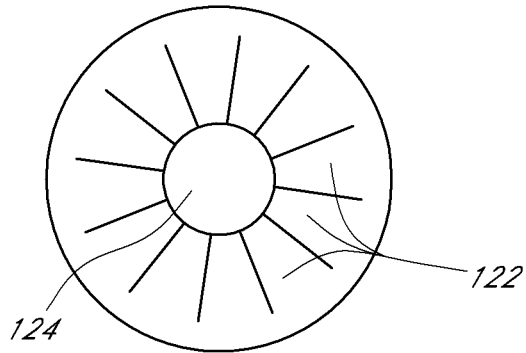
FIG. 34A    FIG. 34B
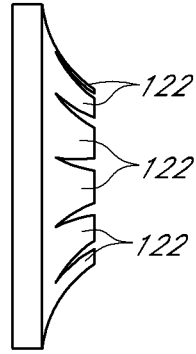
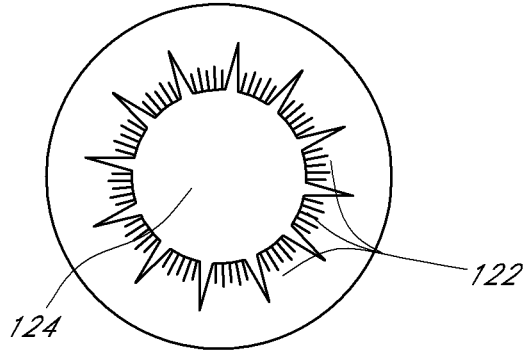
FIG. 35A    FIG. 35B

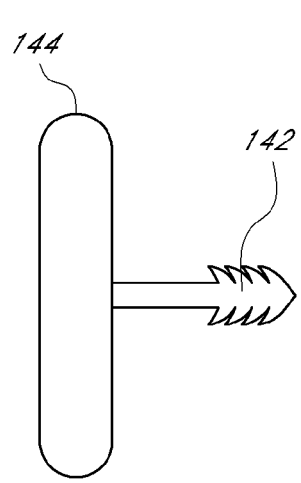
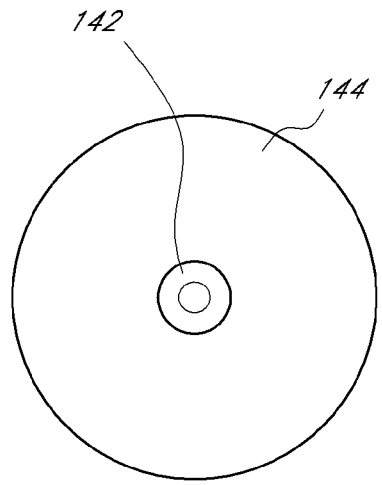
*FIG. 40A*  *FIG. 40B*
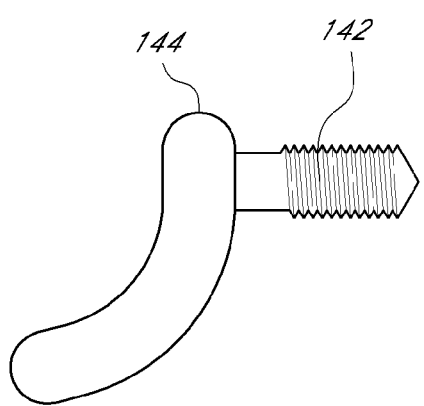
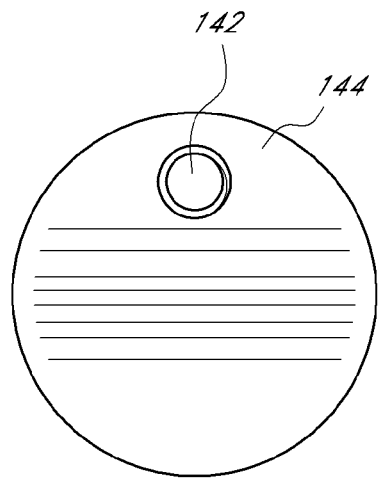
*FIG. 41A*  *FIG. 41B*

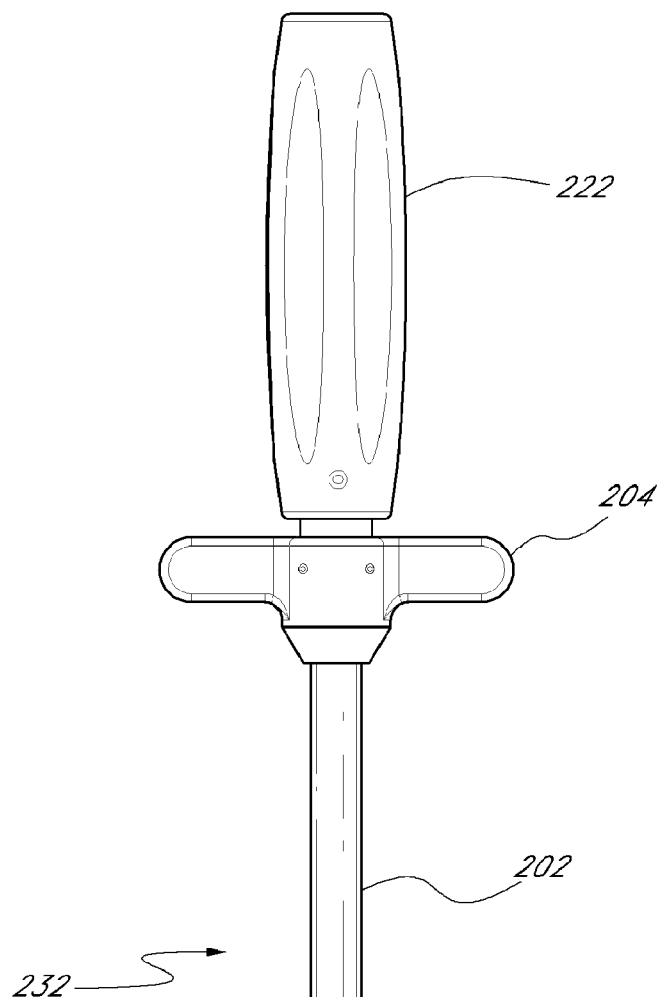
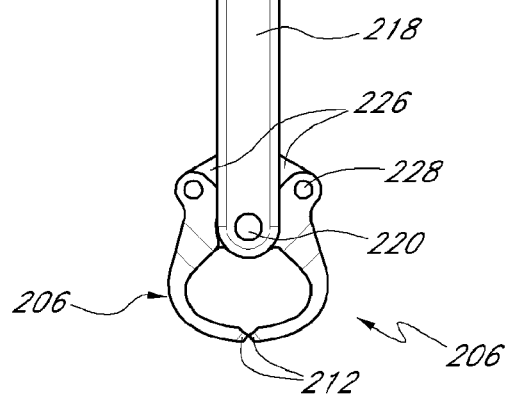
FIG.53A

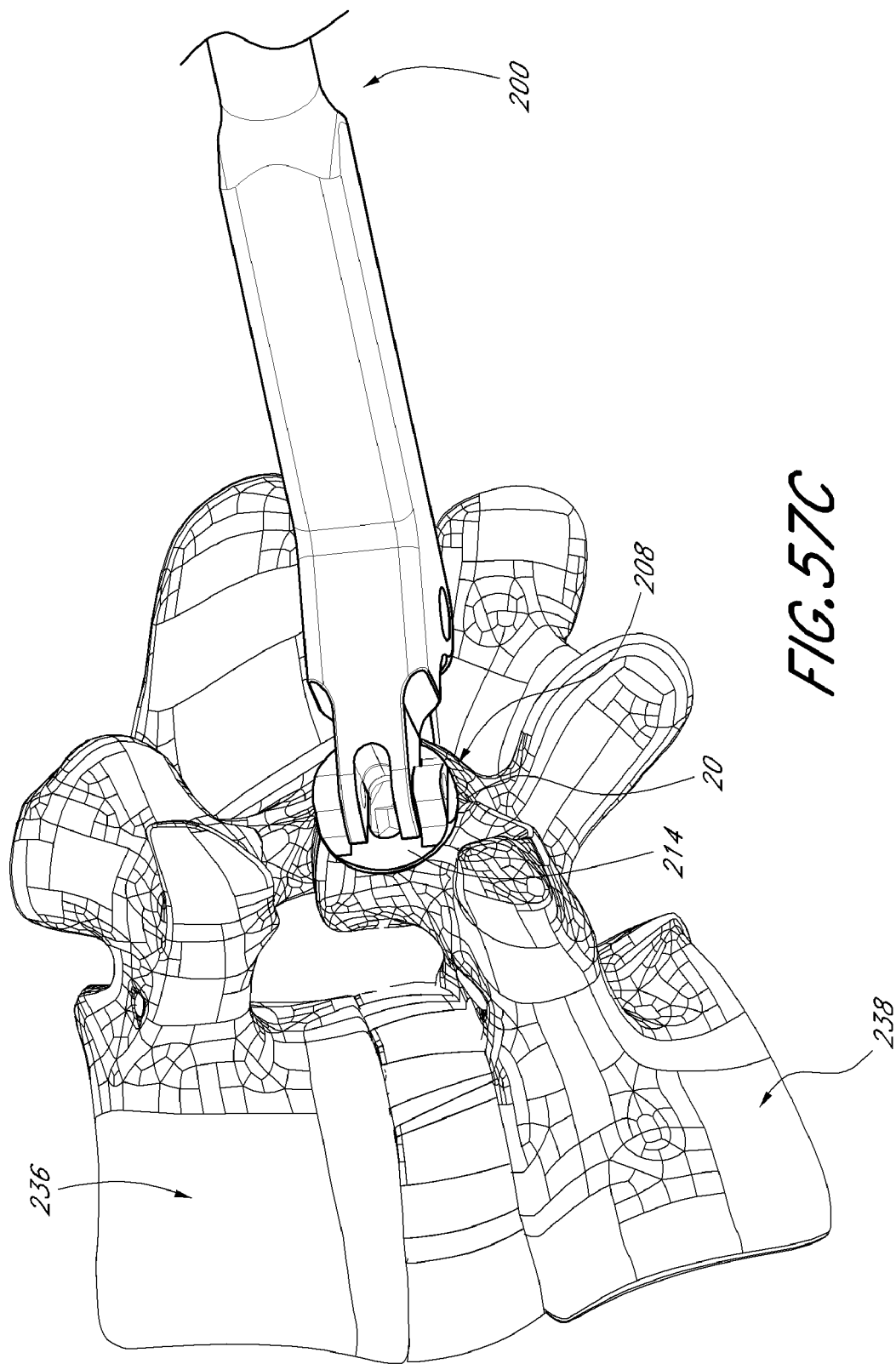

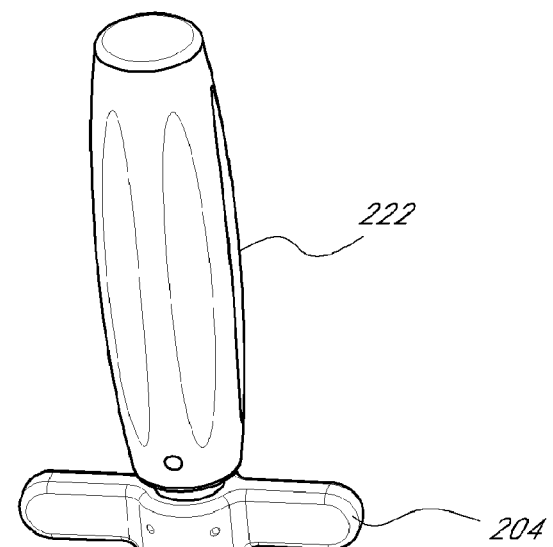
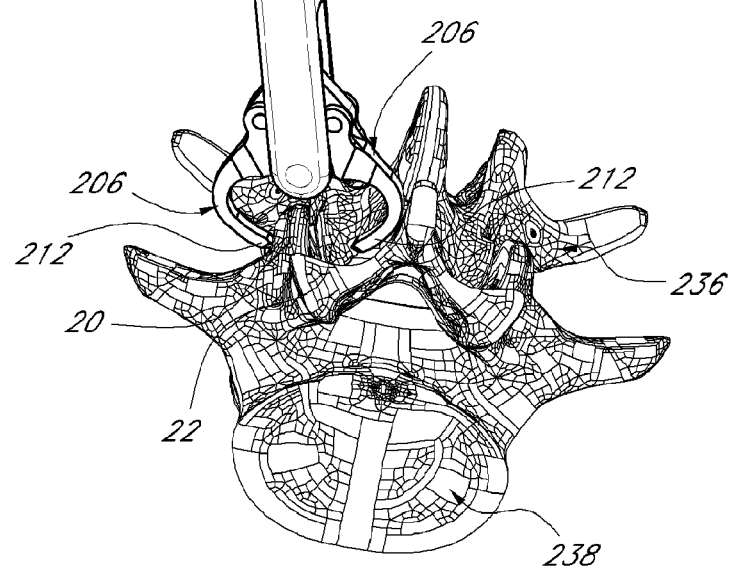
FIG.58A

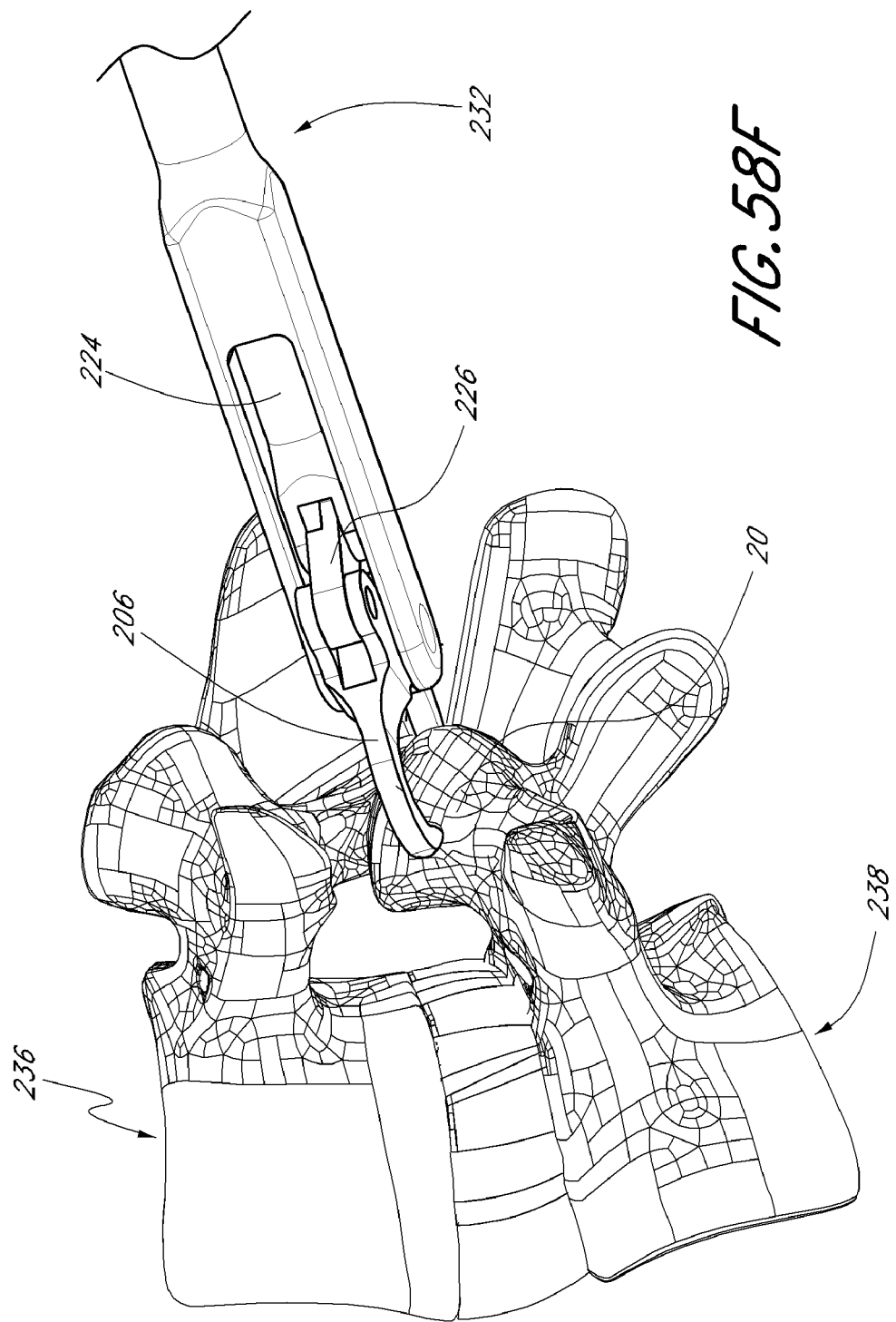

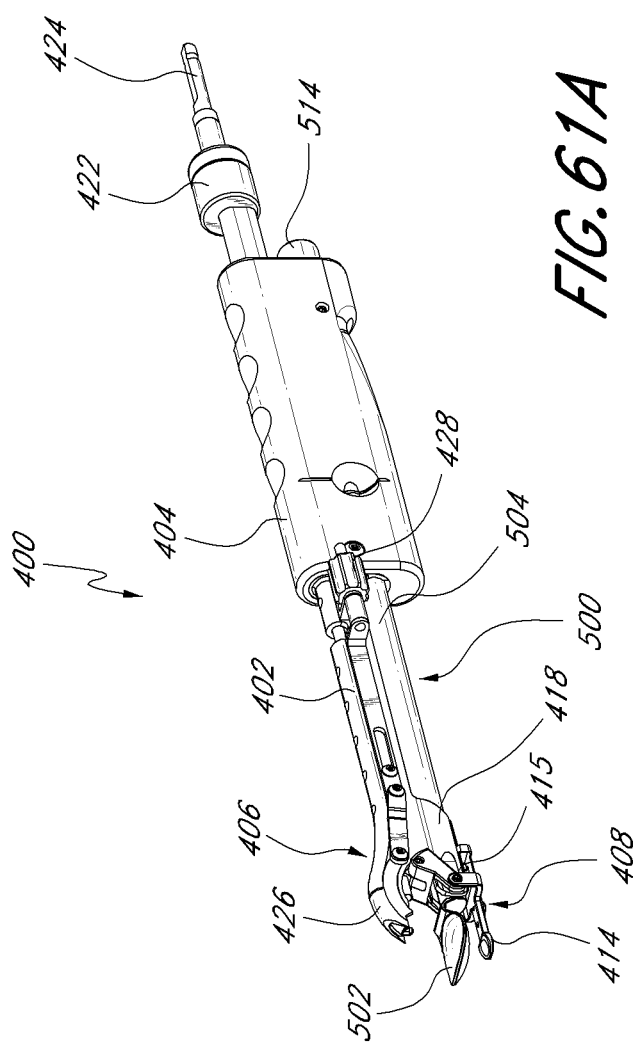

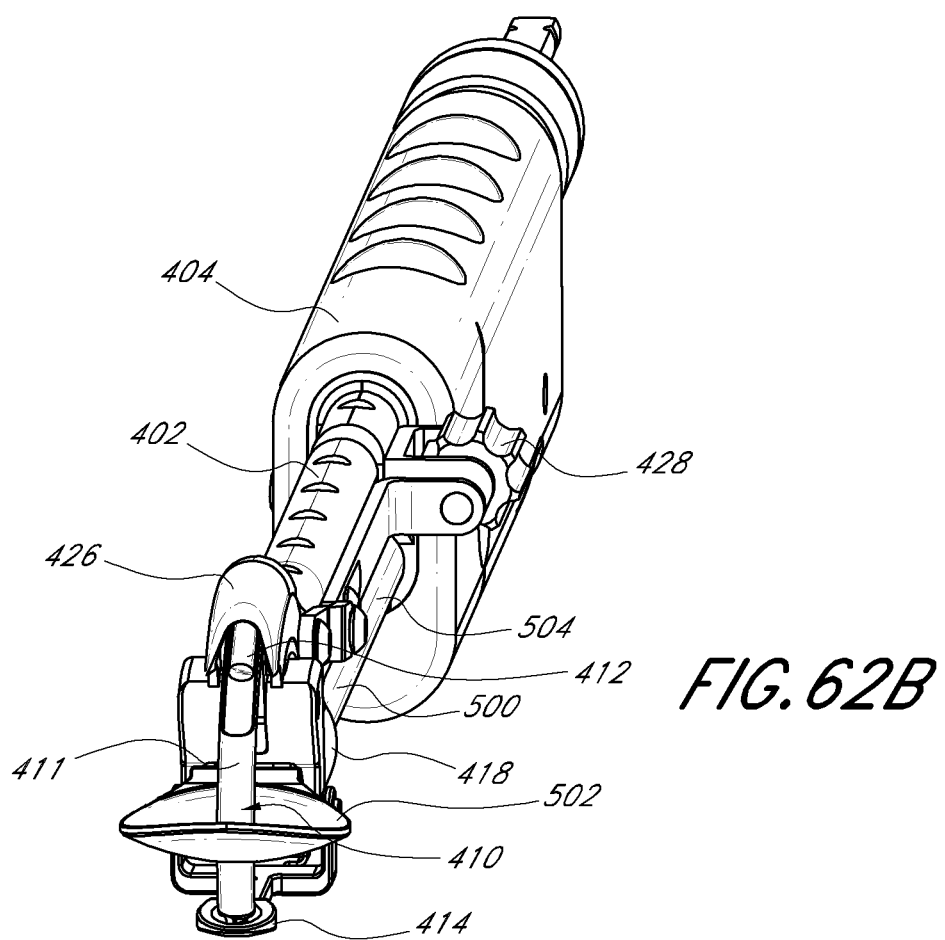

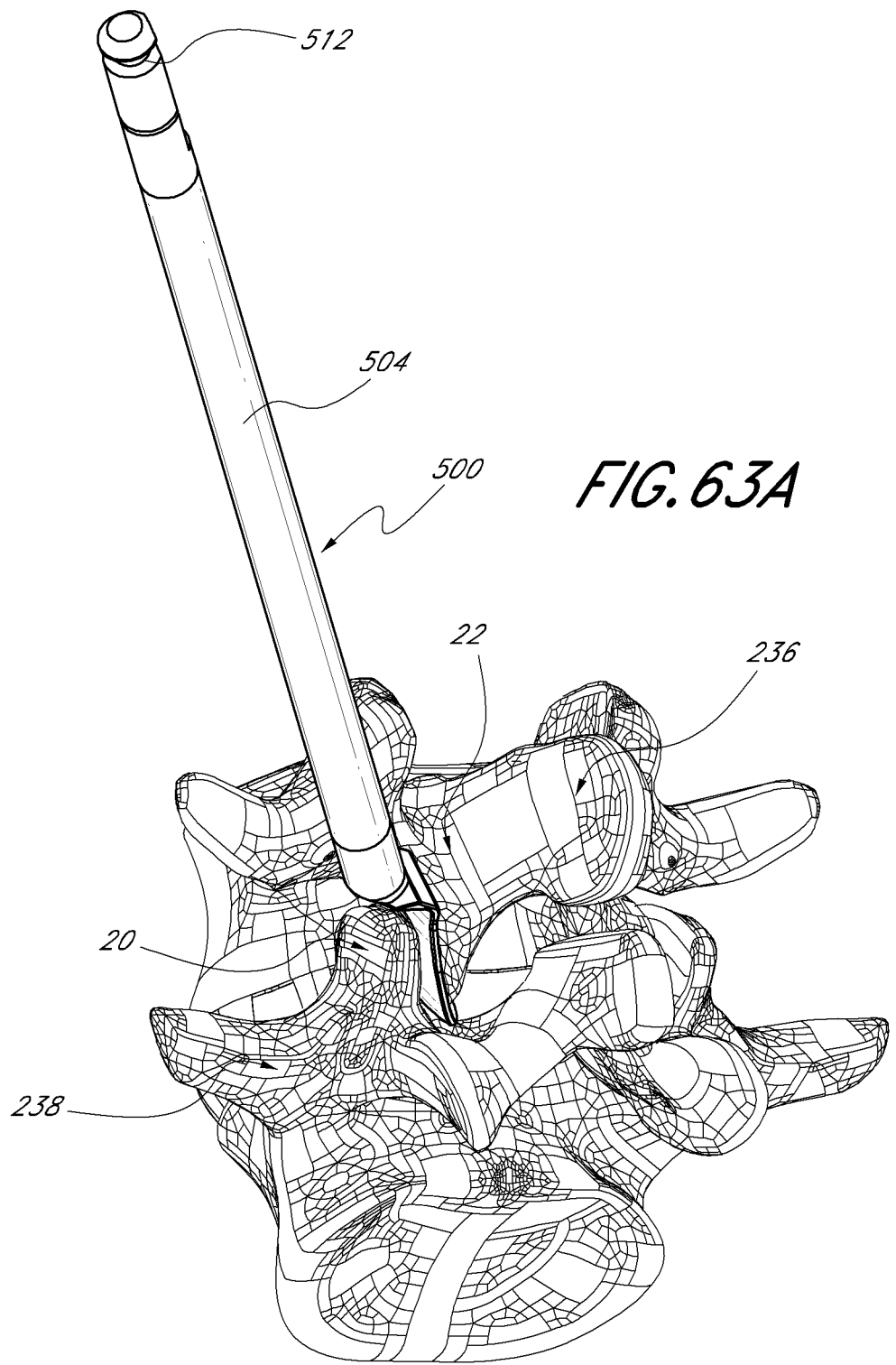

VERTEBRAL FACET JOINT DRILL AND METHOD OF USE

CROSS-REFERENCE TO RELATED APPLICATIONS

The present application is a continuation-in-part of U.S. application Ser. No. 12/035,366 filed on Feb. 21, 2008, which claims priority under 35 U.S.C. §119(e) to U.S. Provisional Application No. 60/891,159 filed on Feb. 22, 2007, the disclosures of which are incorporated by reference herein in their entireties.

TECHNICAL FIELD

The present invention relates to devices for creating holes in the articular processes of the vertebra and the surgical method of using the devices for creation of holes and the use of the holes with facet joint prosthesis retainers.

BACKGROUND

Traumatic, inflammatory, and degenerative disorders of the spine can lead to severe pain and loss of mobility. According to some studies, back and spinal musculoskeletal impairments are the leading causes of lost work productivity in the United States. Pain as a result of some type of spinal impairment may have its source in a variety of pathologies or clinical conditions.

One source for back and spine pain is related to degeneration of the facets of the spine or facet arthritis. Bony contact or grinding of degenerated facet joint surfaces may play a role in some pain syndromes. While many technological advances have focused on the spinal disc and artificial replacement or repair of the disc, little advancement in facet repair has been made. Facet joint and disc degeneration frequently occur together. Thus, there is a need to address the clinical concerns raised by degenerative facet joints.

The current standard of care to address the degenerative problems with the facet joints is to fuse the two adjacent vertebrae together. By performing this surgical procedure, the relative motion between the two adjacent vertebrae is stopped, thus stopping motion of the facets and any potential pain generated as a result thereof. This surgical procedure has a high rate of morbidity and can potentially lead to further clinical complications such as adjacent segment disorders. This procedure is also not reversible. Therefore, if the patient has an unsatisfactory result, they maybe subject to additional surgical fusion procedures.

SUMMARY OF THE INVENTION

The present invention aims at addressing the clinical condition of the patient while allowing the patient to maintain mobility not common with fusion procedures. The device and procedure allow the restoration of the relative spacing between the facets within the facet joint, alleviating the bone on bone contact that is common in degenerative facet joints and often the source of pain generation, while allowing relative motion between the facets to continue post-operatively.

While other implants have been proposed with the objective of addressing facet degeneration by restoring motion, the subject device offers the benefit of requiring little to no bony resection in order for it to be placed within the spine. This advantage provides the opportunity for the patient to rely more on those anatomical structures unaffected by degeneration while providing for very little morbidity in the surgical procedure.

Devices and methods for creating holes in the articular process of the vertebra are provided. Methods of using the resulting holes to anchor or stabilize facet joint prosthesis, and also altering the spacing and motion at the facet joints of the vertebral column, are provided.

In some embodiments, a device for forming a curved lumen in an articular process of a vertebral column can comprise a shaft comprising a proximal section and a distal section. At least one lumen-forming arm can be slideably coupled to the shaft, comprising a tube biased in a curved shape toward the distal section and a flexible drill bit extending axially through the tube and axially rotatable within the tube, the flexible drill bit comprising a drill bit tip configured to cut through a vertebral articular process. A coupler can be disposed toward the proximal section of the shaft and connected to the flexible drill bit, wherein the coupler is configured to transfer axial rotation to the flexible drill bit. The at least one lumen-forming arm can be slideable from a retracted configuration to an advanced configuration, wherein in the advanced configuration the at least one lumen-forming arm extends in the curved shape from the distal section of the shaft.

In some embodiments, the device for forming a curved lumen in an articular process of a vertebral column can comprise an opposing target member. In some embodiments, the arm guide can be distally extendable and comprise a pointed tip configured to secure to the vertebra. Furthermore, the device can comprise a spacing member coupled to the shaft, wherein the spacing member comprises a spacer positioned adjacent the at least one lumen-forming arm.

In some embodiments, a device for forming a lumen in an articular process of a vertebral column can comprise a shaft and at least one lumen-forming arm slideably coupled to the shaft and comprising a drill bit configured to cut through a vertebral articular process. A coupler can be connected to the drill bit, wherein the coupler is configured to transfer axial rotation to the drill bit. The at least one lumen-forming arm can be slideable from a retracted configuration to an advanced configuration, wherein in the advanced configuration the at least one lumen-forming arm can extend from the shaft.

A method for forming a lumen in the articular process of the vertebra can comprise accessing an articular process of a spine and positioning a lumen-forming arm comprising a drill bit against a first articular process. The method can also include the step of rotating the drill bit by coupling a rotational power source to the drill bit and manipulating the lumen-forming arm through the articular process to form a through lumen.

In some embodiments, the method for forming a lumen in the articular process of the vertebra can further comprise positioning a spacer between the first articular process and a second articular process. In some embodiments, the lumen formed in the method can be curved.

One embodiment of the invention comprises a device for treating spinal disorders while preserving movement at a facet joint. The device comprises a prosthesis having a first face and a second face, where the first face is adapted to be secured to the adjacent articular surface of a facet and the second surface is configured for sliding contact with an adjacent structure. In one embodiment, the device is dimensioned to substantially fit within a joint capsule of the facet joint and has a thickness generally equal to the normal anatomic spacing between the two facets of the facet joint. In some embodiments, the device has a curve adapted to match the natural shape of a facet and a size adapted to fit substantially within a joint capsule of the facet joint. The device may comprise at least one material selected from the group consisting of polymers, polyetheretherketone (PEEK), polyetherketoneketone (PEKK), polyethylene, fluoropolymers, hydrogels, elastomers, ceramics, zirconia, alumina, silicon nitride; metal(s), titanium, titanium alloy, cobalt chromium, stainless steel, and combinations of these materials. In one embodiment, the second face of the device comprises a highly polished surface. In one embodiment, the first face may comprise a roughened surface or a porous surface. In some embodiments, at least one face of the device is sufficiently malleable to be capable of generally conforming to the shape of an adjacent surface or structure under normal anatomical loads.

In one embodiment of the invention, a device for treating spinal disorders while preserving movement at a facet joint is provided. The device may comprise a prosthesis having a first face and a second face, where the first face is adapted for sliding contact with a first articular process of a facet joint and the second surface is configured for sliding contact with a second articular process of the facet joint. In one embodiment, the device is dimensioned to substantially fit within a joint capsule of the facet joint and has a thickness generally equal to the normal anatomic spacing between the two facets of a facet joint. In one embodiment, the device has a curve adapted to match the natural shape of a facet and a size adapted to fit substantially within a joint capsule of the facet joint. The device has a thickness approximately equal to the normal anatomic spacing between the two facets of the facet joint. In one embodiment, the device has an average thickness within the range of about 0.5 mm to about 3 mm. In one embodiment, the device has an average thickness within the range of about 1 mm to about 2 mm. In another embodiment, the device has a diameter within the range of about 5 mm to about 25 mm. In another embodiment, the device has a size within the range of about 10 mm to about 20 mm in diameter. In one embodiment, at least one face of the device has a bone contacting surface area of about 25 $mm^2$ to about 700 $mm^2$. In another embodiment, at least one face of the device has a bone contacting surface area of about 20 $mm^2$ to about 400 $mm^2$. In still another embodiment of the device, at least one face of the device has a bone contacting surface area of about 20 $mm^2$ to about 100 $mm^2$. In one embodiment, the device has at least one face comprising a highly polished surface. In some embodiments, at least one face of the device is sufficiently malleable to be capable of generally conforming to the shape of at least a portion of an articular process under normal anatomical conditions.

The prosthesis may further comprise an anchoring assembly configured to generally maintain at least a portion of the prosthesis between the first articular process and the second articular process of the facet joint. The anchoring assembly may comprise an elongate member and at least one retaining member. In one embodiment, the elongate member comprises a wire or cable. In another embodiment, the elongate member comprises a solid wire or cable. In still another embodiment, the elongate member comprises a braided cable. The retaining member may comprise a set screw retaining ring. In one embodiment, at least one end of the device comprises a threaded interface. In one embodiment, the retaining member comprises a threaded retainer. In some embodiments, the retaining member is integrally formed with one end of the elongate member.

In another embodiment of the invention, the device for treating facet joint dysfunction is provided. The device comprises a body with a first face and a second face adapted to contact the bony or cartilaginous articular surfaces of the facets of adjacent vertebrae. The device has at least one retaining interface capable of accepting an elongate retainer through it. An elongate retainer is adapted for generally maintaining the location of the body with respect to the facet joint. The retainer has a first portion adapted to engage a first facet of the facet joint and a second portion adapted to engage a second facet of the facet joint. In some embodiments of the invention, the device has a generally circular cross-section and a diameter adapted to fit substantially within a joint capsule of the facet joint. The device has a thickness generally equal to the normal anatomic spacing between the two facets of the facet joint. In still other embodiments of the device, the device has a curve adapted to match the natural shape of the facet and a size adapted to substantially fit within a joint capsule of the facet. The device may comprise at least one material selected from the group consisting of polymers, polyetheretherketone, polyetherketoneketone, polyethylene, fluoropolymers, hydrogels, elastomers, ceramics, zirconia, alumina, silicon nitride; metal(s), titanium, titanium alloy, cobalt chromium, stainless steel, and combinations of these materials. The elongate retainer may comprise a braided polymer, a braided metal, or a solid structure. In some embodiments of the invention, the elongate retainer comprises a flexibility sufficient to tie a knot in the elongate retainer. In another embodiment, at least one end of the elongate retainer has a threaded metal section adapted to accept a threaded knot. A threaded knot is provided to retain the elongate retainer against an articular process. In one embodiment of the invention, the threaded section is pressed or crimped onto the elongate retainer. The threaded section and knot may comprise titanium, titanium alloy, cobalt chromium or stainless steel. In some embodiments of the invention, the device comprises at least one face of the highly polished surface. In some embodiments, the elongate member may comprise at least one element with an enlarged cross-sectional area. The elongate member may comprise at least one end of with a bulbous retainer, a flared retainer, a T-bar retainer or an integral ring retainer. In some embodiments, at least one face of the device is sufficiently malleable to be capable of generally conforming to the shape of at least a portion of an articular surface.

In one embodiment of the invention, a prosthesis for treating facet joint dysfunction is provided. The prosthesis comprises a body with a first face and a second face, where at least one face adapted for sliding contact with the bony or cartilaginous articular surfaces of the facets of adjacent vertebrae or the prosthesis has at least one retaining interface capable of accepting a retainer member. The retaining member is adapted for securing the location of the body with respect to at least of the articular surfaces. The retaining member may comprise a first portion adapted to engage the retaining interface of the body and a second portion adapted to engage a first facet of the facet joint. The retainer may further comprise a third portion adapted to engage a second facet of the facet joint. In one embodiment, the retainer comprises a threaded shaft and a retaining interface of the body comprises a threaded hole with an opening on one face of the body. The retaining member may also comprise a projection extending from the body. In still another embodiment, the retaining member comprises a longitudinal member adapted to engage the retaining interface of the body and at least one retainer being capable of engaging the longitudinal member. The retaining ring may comprise a set screw retaining ring. The set screw of the retaining member may have a blunted tip, curved tip, or piercing tip. Alternatively, at least one of the retaining rings may be a friction fit retaining ring. The body of the prosthesis may be curved. The prosthesis may comprise at least one material selected from the group consisting of polymers, polyetheretherketone, polyetherketoneketone, polyethylene, fluoropolymers, hydrogels, elastomers, ceramics, zirconia, alumina, silicon nitride; metal(s), titanium, titanium alloy, cobalt chromium, stainless steel, and combinations of these materials. In some embodiments, at least one face of the prosthesis is sufficiently malleable to be capable of generally conforming to the shape of at least a portion of an articular surface.

In one embodiment, a prosthesis for treating facet joint dysfunction is provided. The prosthesis comprises a first body with a first face and a second face and a second body within a first face and a second face. The first face of each body is adapted to articulate with the first face of the other body and the second face of each body is adapted to engage a facet of a facet joint. The prosthesis may further comprise a retaining member adapted for securing a location of at least one body. In some embodiments, at least one face of the prosthesis is sufficiently malleable to be capable of generally conforming to the shape of at least a portion of an articular surface.

In another embodiment of the invention, a method for treating vertebral dysfunction is provided. This method comprises opening a facet joint capsule between two facets of adjacent vertebral bodies, distracting the adjacent vertebral bodies from a first spacing to a second spacing and placing the spacer between the two facets to maintain the second spacing. The method may further comprise the steps of securing the spacer to one facet of the facet joint. The method may also comprise securing the spacer in the facet joint capsule. The step of securing the spacer may comprise introducing a hole through each facet, threading a retainer through the hole of the first facet, threading the retainer through the hole in the spacer, threading the retainer through the hole of the second facet, and tying a knot in at least one end of the retainer. The method may further comprise the steps of introducing a hole through a first facet and a second facet, advancing the retainer through the hole of the first facet, advancing the retainer through the hole in the spacer, threading the retainer through the hole of the second facet and threadably engaging an anchor to at least one end of the retainer. The step of securing the spacer may further comprise providing a spacer with a retaining member and advancing the retaining member at least partially into a facet to engage the facet. The method may also further comprise the step of conforming the shape of at least a portion of the spacer to at least a portion of a facet of the facet joint. In a further embodiment, the conforming step is performed after the placing step. In another embodiment, the conforming step is performed while the spacer is generally located between the facets of the facet joint.

In another embodiment of the invention, a method of treating the facet joint is provided. The method comprises providing a prosthesis dimension to fit within a facet joint capsule, accessing a facet joint capsule between two articular prosthesis of two vertebrae, inserting a prosthesis generally within the joint capsule and maintaining the prosthesis generally between the two articular prosthesis without penetrating the surface of a vertebrae. Maintaining the prosthesis may comprise anchoring the prosthesis to the joint capsule tissue, or generally closing the joint capsule over the prosthesis. The prosthesis can also be maintained between the articular prosthesis by suturing the prosthesis to the surrounding soft tissue. The method may also further comprise the step of conforming the shape of at least a portion of the prosthesis to at least a portion of a facet of the facet joint. In a further embodiment, the conforming step is performed after the inserting step. In another embodiment, the conforming step is performed while the prosthesis is generally located between the facets of the facet joint.

BRIEF DESCRIPTION OF THE DRAWINGS

The structure and operation of the invention will be better understood with the following detailed description of embodiments of the invention, along with the accompanying illustrations, in which:

FIGS. 7A and 7B are schematic views of one embodiment of a facet joint prosthesis comprising a circular disc;

FIG. 8 is a schematic view of the prosthesis from FIG. 7A implanted in a facet joint;

FIGS. 12A and 12B are schematic views of one embodiment of a facet joint prosthesis comprising a curved disc;

FIG. 13 is a schematic view of the prosthesis from FIG. 12A implanted in a facet joint;

FIGS. 14A and 14B are schematic views of one embodiment of a facet joint prosthesis comprising a disc with a roughened surface on one face;

FIGS. 15A and 15B are schematic views of one embodiment of a facet joint prosthesis comprising a disc with a porous surface on one face;

FIGS. 16A and 16B are schematic views of one embodiment of a facet joint prosthesis comprising a bent disc with a roughened surface on the greater face;

FIG. 17 is a schematic view of the prosthesis from FIG. 16A implanted in a facet joint;

FIGS. 22A and 22B are schematic views of one embodiment of a facet joint prosthesis with a retaining interface comprising an eccentrically located hole;

FIGS. 23A and 23B are schematic views of one embodiment of a facet joint prosthesis with a retaining interface comprising an edge contiguous hole;

FIGS. 25A and 25B are schematic views of one embodiment of a facet joint prosthesis comprising a curved disc with a retaining interface;

FIG. 26 depicts one embodiment of the invention where the cable is engaged to the articular processes using knots in the cable;

FIGS. 34A to 35B are one embodiment of the invention comprising friction fit retaining rings. FIGS. 34A and 34B depict the retaining rings in their reduced state and FIGS. 35A and 35B depict the retaining rings in their expanded state;

FIGS. 36B and 36C depict a threaded retaining member with a pivotable washer;

FIGS. 40A and 40B are schematic views of one embodiment of a facet joint prosthesis with an integral retaining member comprising a centrally located barbed spike;

FIGS. 41A and 41B are schematic views of one embodiment of a facet joint prosthesis with an integral retaining member comprising an eccentrally located barbed spike;

FIGS. 51A to 51C are posterior views of the surgical procedure and FIGS. 51D and 51E are cross sectional views of the surgical procedure.

FIGS. 53A to 53F are one embodiment of the tool with punch drill arms.

FIGS. 57A to 57E show an embodiment of the method of use of the tool in FIGS. 52A to 52F wherein it is used to create a hole in the articular process of the vertebra.

FIGS. 58A to 58G show an embodiment of the method of use of the tool in FIGS. 53A to 53E wherein it is used to create a hole in the articular process of the vertebra.

FIGS. 61A to 61D illustrate various views of the curved lumen forming tool having a drill bit, according to an embodiment of the present invention.

FIGS. 62A and 62B illustrate a side elevational view and front close-up perspective view of the tool in FIGS. 61A to 61D with the lumen-forming arm in the extended configuration.

FIGS. 63A to 63D illustrate an embodiment of the method of use of the tool in FIGS. 61A to 61D wherein the tool is positioned among the articular processes of the vertebrae.

DETAILED DESCRIPTION

A. Anatomy of the Spine

Figure 1:
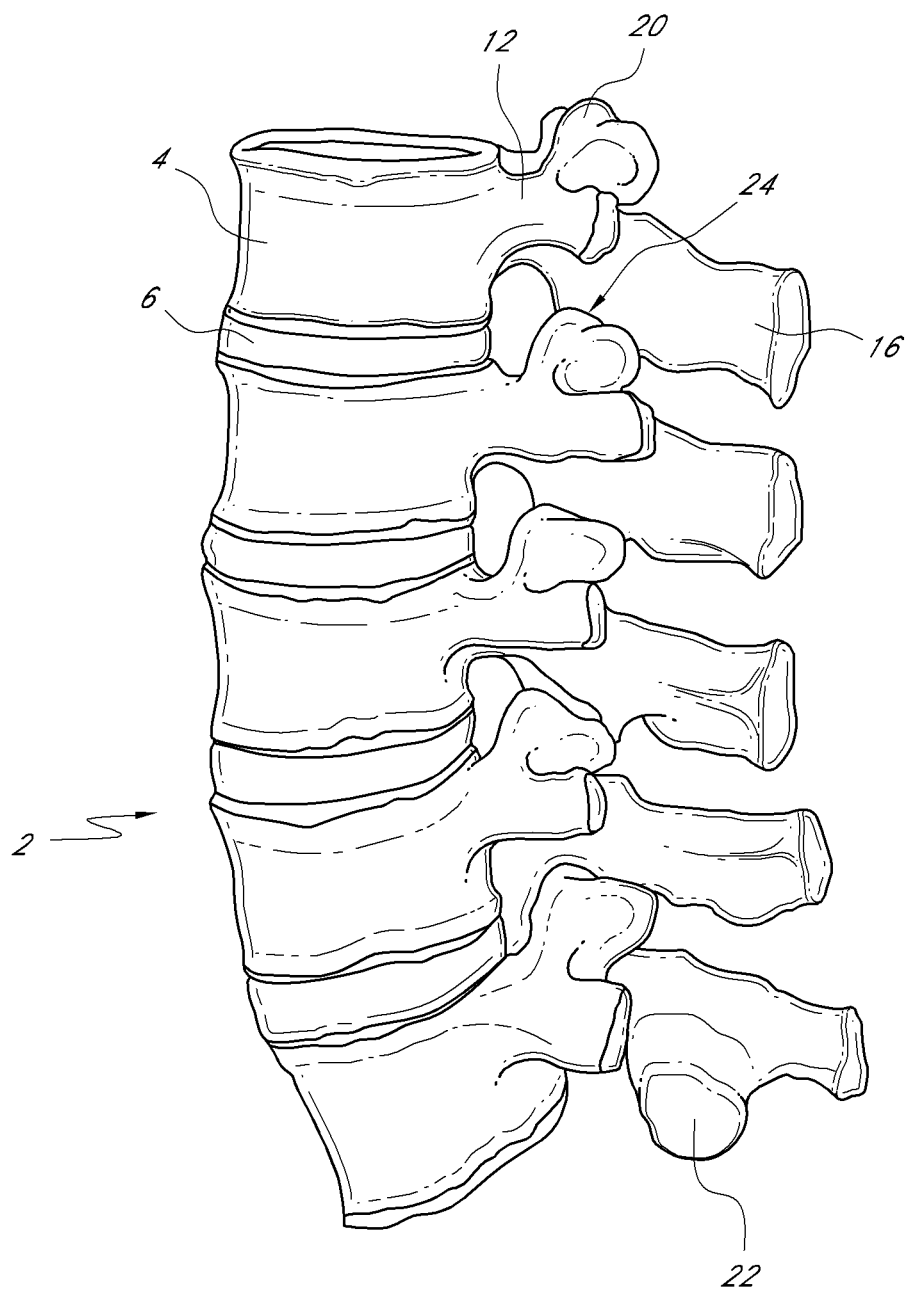
FIG. 1 is a lateral elevational view of a portion of the vertebral column.
Figure 2A:
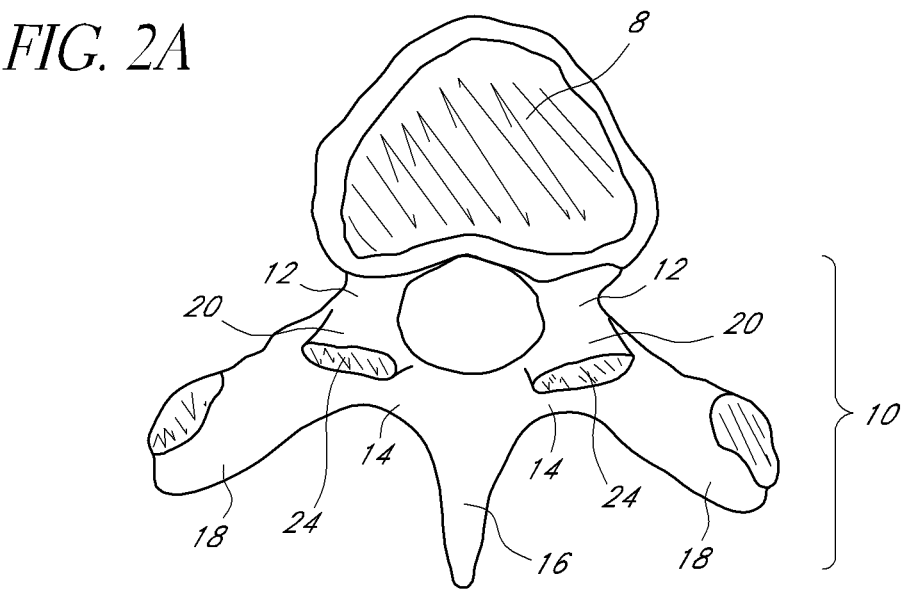
FIGS. 2A and 2B are schematic superior and side views of an isolated thoracic vertebra.
Figure 2B:
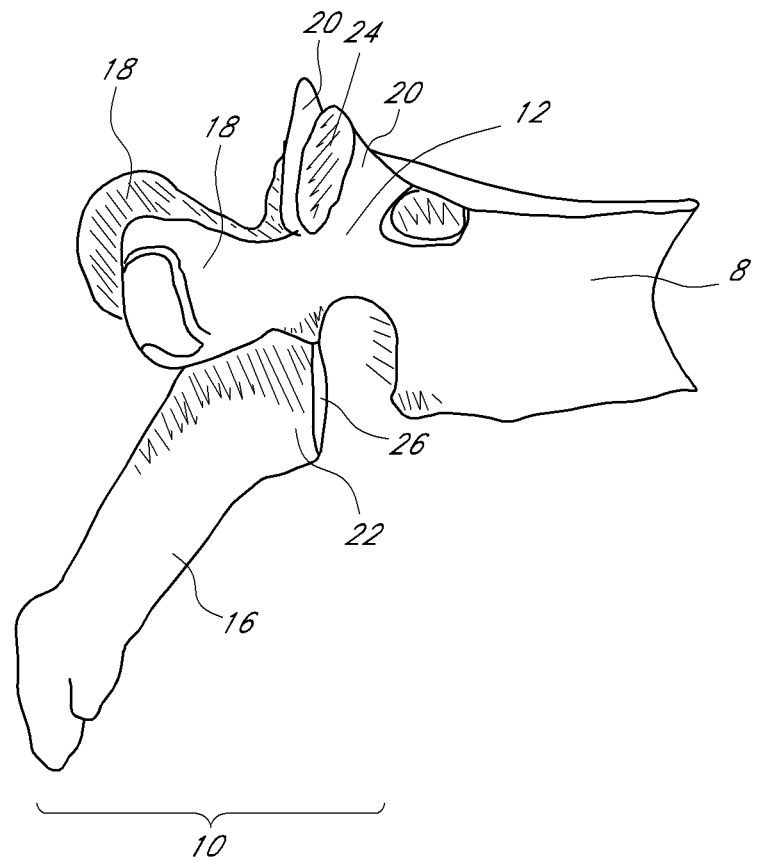
Figure 3A:
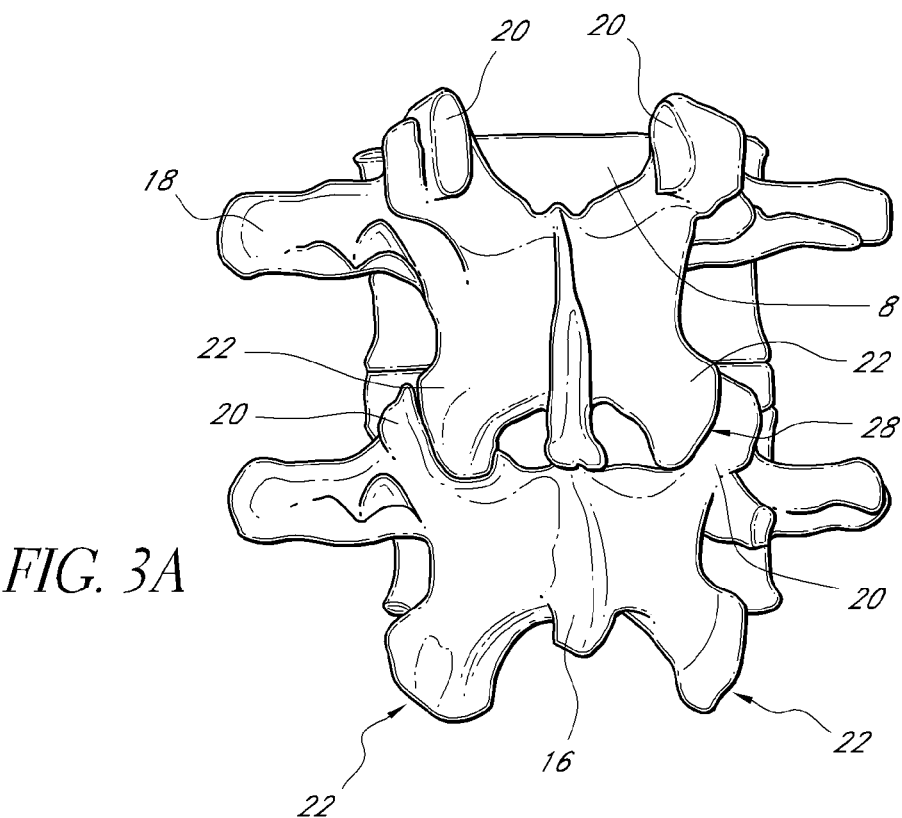
FIGS. 3A and 3B are schematic posterior and posterior-oblique elevational views of a portion of the vertebral column.
Figure 3B:
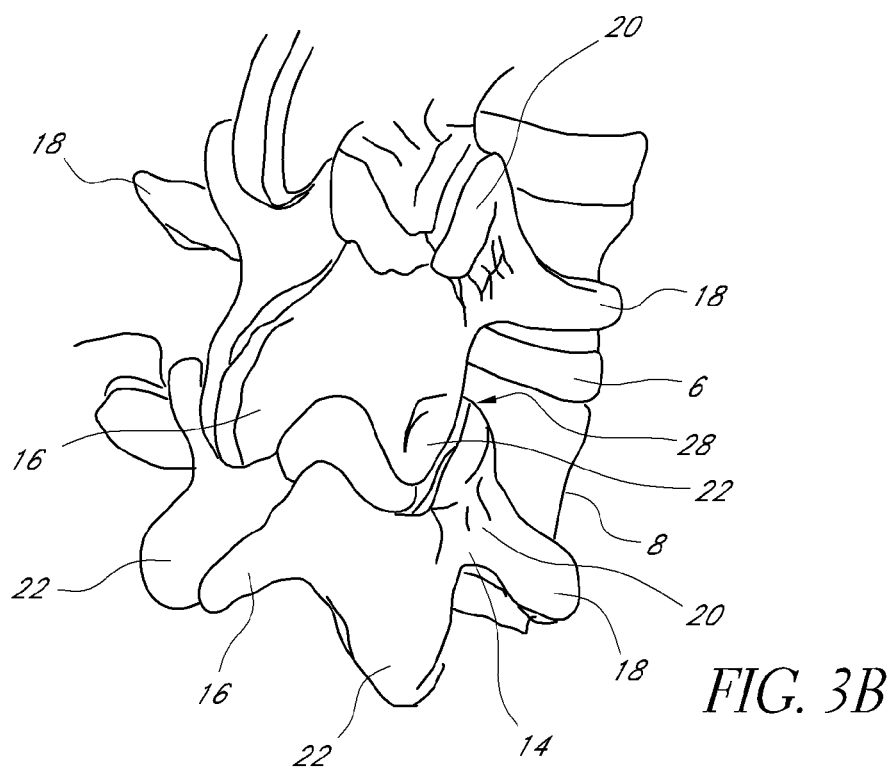
Figure 4A:
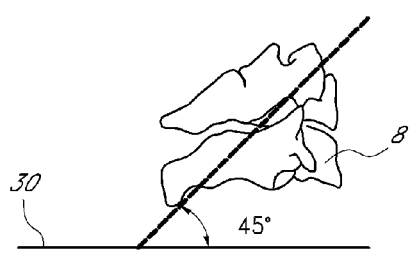
FIGS. 4A and 4B are schematic side and superior views of a facet joint in the cervical vertebrae.
Figure 4B:
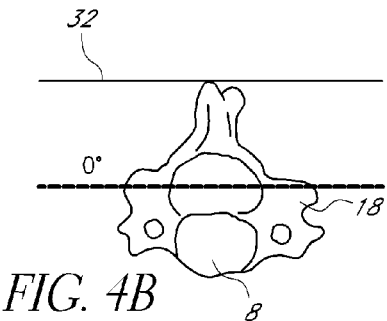

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 comprises two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 with the articular processes of the adjacent vertebra. See FIGS. 3A and 3B. The facet joints are true synovial joints with cartilaginous surfaces and a joint capsule.

Figure 5A:
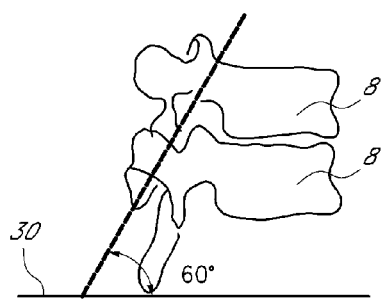
FIGS. 5A and 5B are schematic side and superior views of a facet joint in the thoracic vertebrae.
Figure 5B:
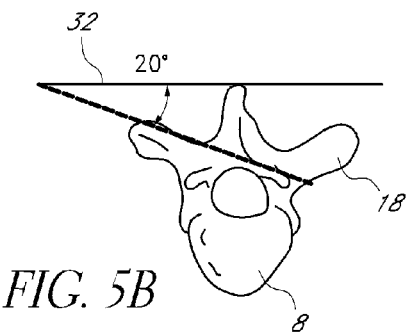
Figure 6A:
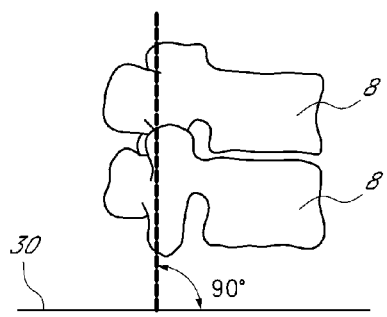
FIGS. 6A and 6B are schematic side and superior views of a facet joint in the lumbar vertebrae.
Figure 6B:
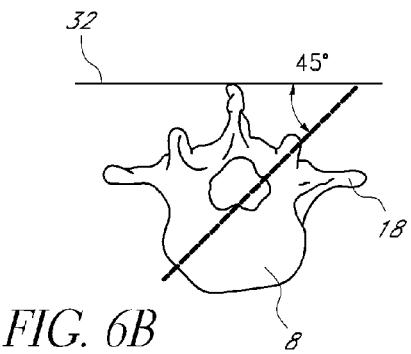

The orientation of the facet joints vary, depending on the level of the vertebral column. In the C1 and C2 vertebrae, the facet joints are parallel to the transverse plane. FIGS. 4A to 6B depict the orientations of the facet joints at different levels of the vertebral column. In the C3 to C7 vertebrae shown in FIGS. 4A and 4B, the facets are oriented at a 45-degree angle to the transverse plane 30 and parallel to the frontal plane 32, respectively. This orientation allows the facet joints of the cervical vertebrae to flex, extend, lateral flex and rotate. At a 45-degree angle in the transverse plane 30, the facet joints of the cervical spine can guide, but do not limit, the movement of the cervical vertebrae. FIGS. 5A and 5B depict the thoracic vertebrae, where the facets are oriented at a 60-degree angle to the transverse plane 30 and a 20-degree angle to the frontal plane 32, respectively. This orientation is capable of providing lateral flexion and rotation, but only limited flexion and extension. FIGS. 6A and 6B illustrate the lumbar region, where the facet joints are oriented at 90-degree angles to the transverse plane 30 and a 45-degree angle to the frontal plane 32, respectively. The lumbar vertebrae are capable of flexion, extension and lateral flexion, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. Mechanism of Spinal Injury Due to Caudocephalad Acceleration, *Orthop. Clin. North Am.*, 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

B. Joint Prosthesis

Figure 9A:
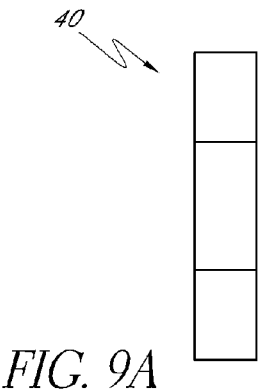
FIGS. 9A and 9B are schematic views of one embodiment of a facet joint prosthesis comprising an octagonal disc.
Figure 9B:
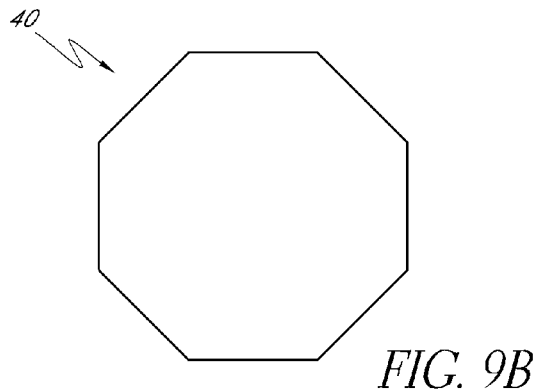

In one embodiment of the invention, a device for restoring the spacing between two facets of a facet joint is provided. As shown in FIGS. 7A and 7B, the device comprises a prosthesis 34 with a least two faces, a first face 36 adapted to contact the articular surface of one facet of the facet joint and a second face 38 adapted to contact the articular surface of the other facet. In one embodiment, the prosthesis 34 has a generally circular profile and is sized to fit generally within the joint capsule of the facet joint 28. FIG. 8 illustrates the prosthesis 34 of FIGS. 7A and 7B positioned in a facet joint. In other embodiment of the invention, the prosthesis can have any of a variety of profiles, including but not limited to square, rectangle, oval, star, polygon or combination thereof. An octagonal prosthesis is shown in FIGS. 9A and 9B. In one embodiment of the invention, a prosthesis having the desired shape is selected from an array of prostheses after radiographic visualization of the articular processes and/or by radio-contract injection into the facet joint to visualize the joint capsule. In one embodiment, the prosthesis has a diameter of about 4 mm to about 30 mm. In another embodiment, the prosthesis has a diameter of about 5 mm to about 25 mm. In still another embodiment, the prosthesis has a diameter of about 10 mm to about 20 mm. In one embodiment, the prosthesis has a cross-sectional area of about 10 mm$^2$ to about 700 mm$^2$. In another embodiment, the prosthesis has a cross-sectional area of about 25 mm$^2$ to about 500 mm$^2$. In still another embodiment, the prosthesis has a cross-sectional area of about 20 mm$^2$ to about 400 mm$^2$, and preferably about 25 mm$^2$ to about 100 mm$^2$.

Figure 10A:
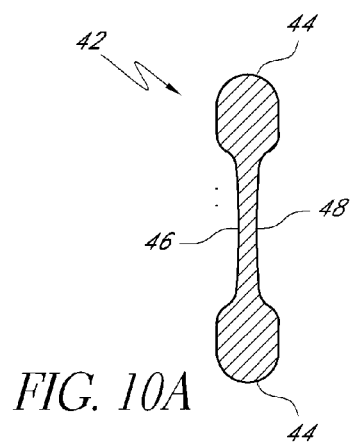
FIGS. 10A and 10B are schematic views of one embodiment of a facet joint prosthesis comprising a biconcave disc.
Figure 10B:
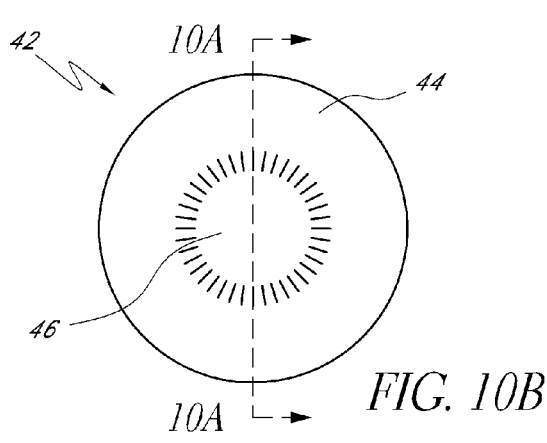
Figure 11A:
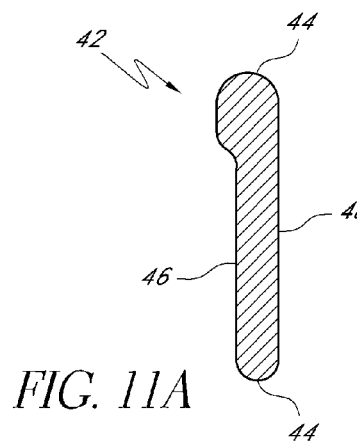
FIGS. 11A and 11B are schematic views of one embodiment of a facet joint prosthesis comprising a single-face variable thickness disc.
Figure 11B:
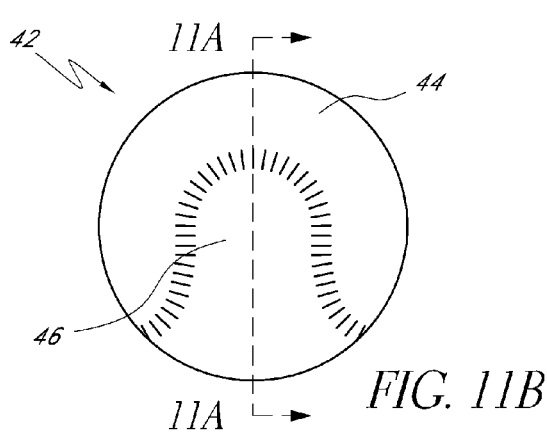

The prosthesis has a thickness generally equal to about the anatomic spacing between two facets of a facet joint. The prosthesis generally has a thickness within the range of about 0.5 mm to about 3.0 mm. In certain embodiments, the prosthesis has a thickness of about 1 mm to about 2 mm. In one preferred embodiment, the prosthesis has a thickness of about 0.5 mm to about 1.5 mm. In one embodiment, the thickness of the prosthesis is nonuniform within the same prosthesis. For example, in FIGS. 10A and 10B, the thickness of the prosthesis 42 is increased around the entire outer edge 44, along at least one and, as illustrated, both faces 46, 48. In FIGS. 11A and 11B, only a portion of the edge 44 on one face 46 of the prosthesis 42 has a thickness that is greater than the thickness of a central region, and, optionally, also thicker than the typical anatomic spacing between two facets of a facet joint. An increased edge thickness may resist lateral displacement of the prosthesis out of the facet joint.

In some embodiments of the invention, the prosthesis is configured to provide an improved fit with the articular process and/or joint capsule. For example, in FIGS. 12A and 12B, the prosthesis 49 has a bend, angle or curve 50 to generally match the natural shape of an articular facet. FIG. 13 depicts the prosthesis of FIGS. 12A and 12B positioned in a facet joint. The prosthesis may be rigid with a preformed bend. Alternatively, the prosthesis may be sufficiently malleable that it will conform post implantation to the unique configuration of the adjacent facet face. Certain embodiments of the invention, such as those depicted in FIG. 8 and FIG. 13, the prosthesis is configured to be implanted between the articular processes and/or within the joint capsule of the facet joint, without securing of the prosthesis to any bony structures. Such embodiments can thus be used without invasion or disruption of the vertebral bone and/or structure, thereby maintaining the integrity of the vertebral bone and/or structure.

In one embodiment, at least a portion of one surface of the prosthesis is highly polished. A highly polished portion of the prosthesis may reduce the surface friction and/or wear in that portion of the prosthesis as it contacts bone, cartilage or another surface of the prosthesis. A highly polished surface on the prosthesis may also decrease the risk of the prosthesis wedging between the articular surfaces of the facet joint, which can cause pain and locking of the facet joint.

In one embodiment, shown in FIGS. 14A and 14B, at least a portion of one surface of the prosthesis 50 has a roughened surface 52. A roughened surface may be advantageous when in contact with a bone or tissue surface because it may prevent slippage of the prosthesis 50 against the bone and aid in maintaining the prosthesis 50 in the joint. In one embodiment of the invention, shown in FIGS. 15A and 15B, at least a portion of one surface of the prosthesis 50 has a porous surface 54. A porous surface 54 can be created in any a variety of ways known in the art, such as by applying sintered beads or spraying plasma onto the prosthesis surface. A porous surface 54 can allow bone to grow into or attach to the surface of the prosthesis 50, thus securing the prosthesis 50 to the bone. In one embodiment, an adhesive or sealant, such as a cyanoacrylate, polymethylmethacrylate, or other adhesive known in the art, is used to bond one face of the prosthesis to an articular surface.

In one embodiment of the invention, one surface of the prosthesis is roughened or porous and a second surface that is highly polished. The first surface contacts or engages one facet of the facet joint and aids in maintaining the prosthesis between the articular surfaces. The second surface of the prosthesis is highly polished and contacts the other facet of the facet joint to provide movement at that facet joint. FIGS. 16A and 16B represent one embodiment of the prosthesis comprising a curved or bent disc 56 with a roughened surface 52 on the greater face 58 of the disc and a highly polished surface 60 on the lesser face 62. FIG. 17 depicts the prosthesis of FIGS. 16A and 16B positioned in a facet joint. The prosthesis generally maintains a fixed position relative to the facet contacting the roughened surface while the movement of the facet joint is preserved between the other facet and the highly polished lesser face of the prosthesis.

Figure 18A:
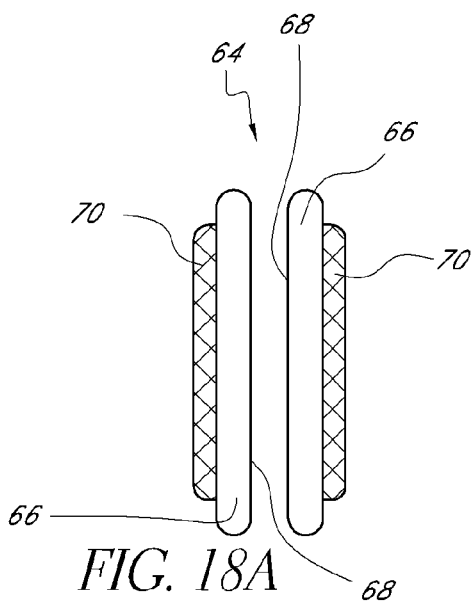
FIGS. 18A and 18B are schematic views of one embodiment of a facet joint prosthesis comprising two discs, each with a roughened surface on one face.
Figure 18B:
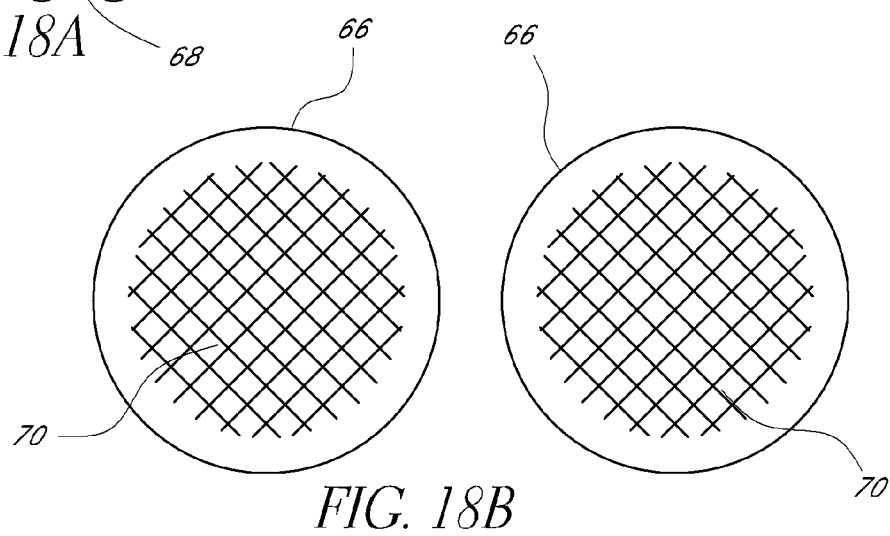
Figure 19:
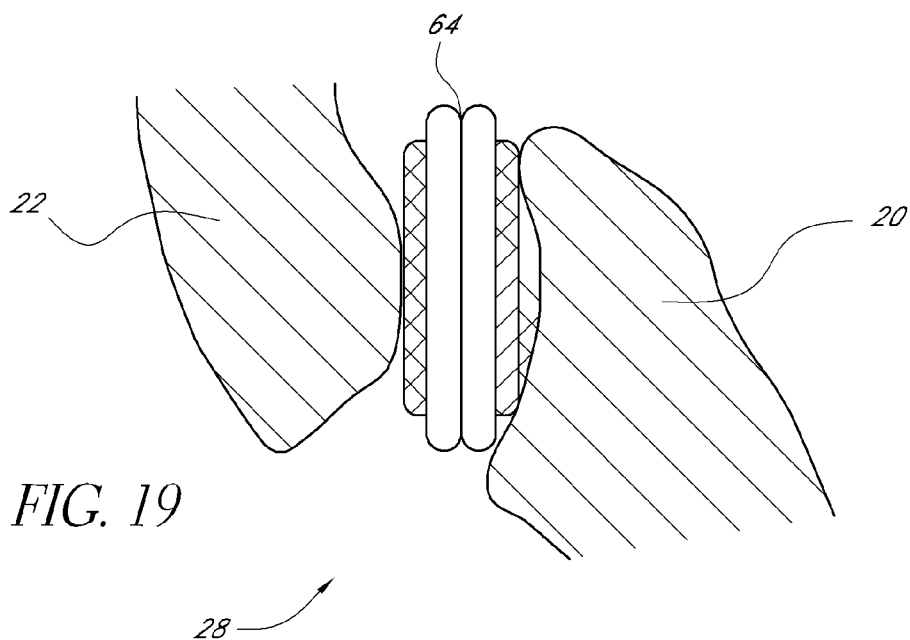
FIG. 19 is a schematic view of the prosthesis from FIG. 18A implanted in a facet joint.

FIGS. 18A and 18B show one embodiment of the invention, where the prosthesis 64 comprises two separate discs 66, each disc comprising a first face 68 that articulates with the complementary first face 68 of the other disc, and a second face 70 adapted to secure the disc to the adjacent bone or cartilage of one facet of the facet joint 28. In one embodiment of the invention, the thickness of one disc will generally be about half of the anatomic spacing between two facets of the facet joint. In other embodiments of the invention, the prosthesis comprises three or more discs. In one embodiment the total thickness of all the discs is generally about 25% to about 300% of the anatomic spacing between the two facets. In another embodiment, the total thickness of the discs is generally about 50% to about 150% of the anatomic spacing. In still another embodiment, the total thickness of the discs is about 75% to about 125% of the anatomic spacing. Each disc of the two-part prosthesis can otherwise also have features similar to those of a single-disc prosthesis, including but not limited to curved or bent configurations, highly polished or roughened surfaces, and other feature mentioned below. The two discs need not have the same size, thickness, configuration or features. FIG. 19 depicts one embodiment of a two-part prosthesis 64 positioned within a facet joint 28.

The prosthesis can be manufactured from any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the above materials.

C. Prosthesis with a Retaining Configuration

In one embodiment of the invention, the prosthesis is maintained between the two facets of the facet joint by taking advantage of the joint capsule and/or other body tissue surrounding the facet joint to limit the migration of the prosthesis out of the facet joint. In some embodiments of the invention, the shape of the prosthesis itself is capable of resisting displacement of the prosthesis from its position generally between the facet joint surfaces. In one embodiment, a concave or biconcave configuration resists displacement of the prosthesis by providing an increased thickness at the periphery of the prosthesis that requires a larger force and/or greater distraction of facet joint surfaces in order to cause displacement. In other embodiments, surface treatments or texturing are used to maintain the prosthesis against a facet of the facet joint, as described previously. In some embodiments, a combination of disc configuration, surface texturing and existing body tissue or structures are used to maintain the position of the prosthesis.

Bone growth facilitators, electrical current, or other known techniques may be used to accelerate osteoincorporation of textured or microporous anchoring surfaces.

D. Prosthesis with a Retaining Member

The prosthesis may be configured with a retaining interface to engage a retaining member that facilitates retention of the prosthesis within the joint capsule of the facet joint. Use of a retaining member may be advantageous for preventing migration of the prosthesis over time use or with the extreme ranges of vertebral movement that may distract the articular surfaces sufficiently to allow the prosthesis to slip out.

1. Wire/Cable Retaining Member

Figure 20:
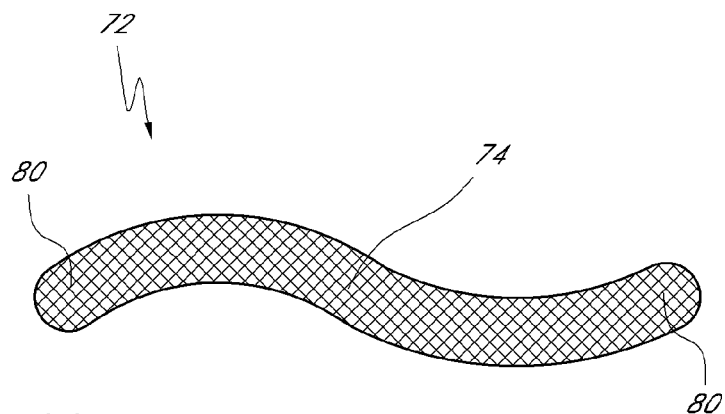
FIG. 20 is a schematic view of a retaining member comprising a braided cable.
Figures 21A, 21B:
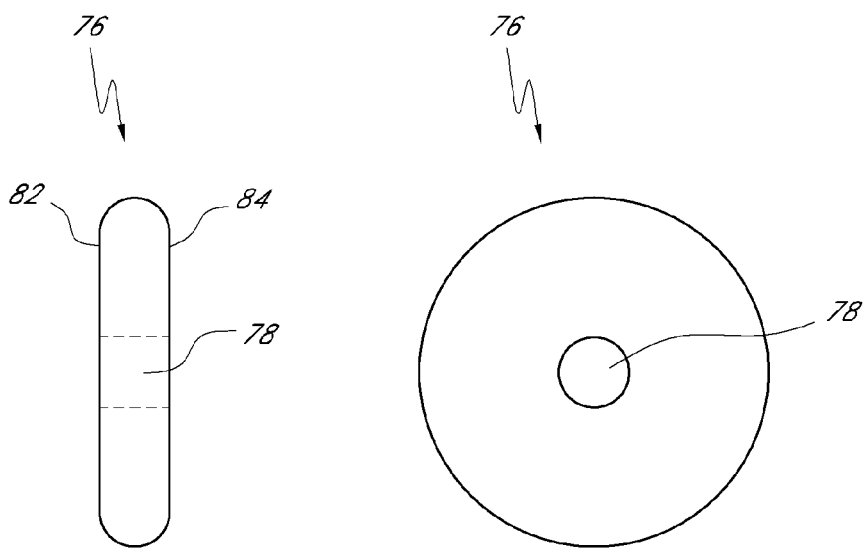
FIGS. 21A and 21B are schematic views of one embodiment of a facet joint prosthesis with a retaining interface comprising a centrally located hole.

In one embodiment of the invention, shown in FIGS. 20 to 21B, the retaining member comprises a wire or cable 72 with a portion 74 that engages the prosthesis 76 at a retaining interface 78, and at least one other portion 80 that engages or anchors to the bone or soft tissue surrounding the facet joint. The wire or cable may be solid, braided or multi-filamented. The retaining member in this embodiment will be described primarily as a cable or wire, but it is to be understood that any of a variety of elongate structures capable of extending through a central aperture will also work, including pins, screws, and single strand or multistrand polymeric strings or weaves, polymeric meshes and fabric and other structures that will be apparent to those of skill in the art in view of the disclosure herein.

The cross-sectional shape of the retaining member can be any of a variety of shapes, including but not limited to circles, ovals, squares, rectangles, other polygons or any other shape. The wire or cable generally has a diameter of about 0.5 mm to about 2 mm and a length of about 5 mm to about 60 mm. In another embodiment, wire or cable has a diameter of about 0.25 mm to about 1 mm, and preferably about 0.75 mm to about 1.25 mm. The diameter of the wire or cable may vary along the length of the wire or cable. In one embodiment, the wire or cable has a length of about 10 mm to about 40 mm. In another embodiment, the wire or cable has a length of about 20 mm to about 30 mm.

In one embodiment, shown in FIGS. 21A and 21B, the retaining interface 78 of the prosthesis 76 is a conduit between the two faces 82, 84 of the prosthesis 76, forming an aperture 78. In one embodiment, the aperture 78 has a diameter larger than the diameter of the wire or cable 72, to provide the prosthesis 76 with a range of motion as the facet joint moves. The aperture 78 inside diameter may be at least about 110%, often at least about 150% and in certain embodiments at least about 200% or 300% or greater of the outside diameter or corresponding dimension of the retaining member in the vicinity of the engagement portion 78. The cross-sectional shape of the aperture 78 can match or not match the cross sectional shape of the wire or cable used.

Figure 24A:
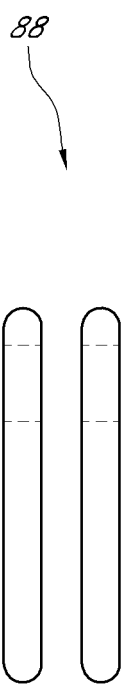
FIGS. 24A and 24B are schematic views of one embodiment of a facet joint prosthesis comprising two discs, each with an eccentrically located hole.
Figure 24B:
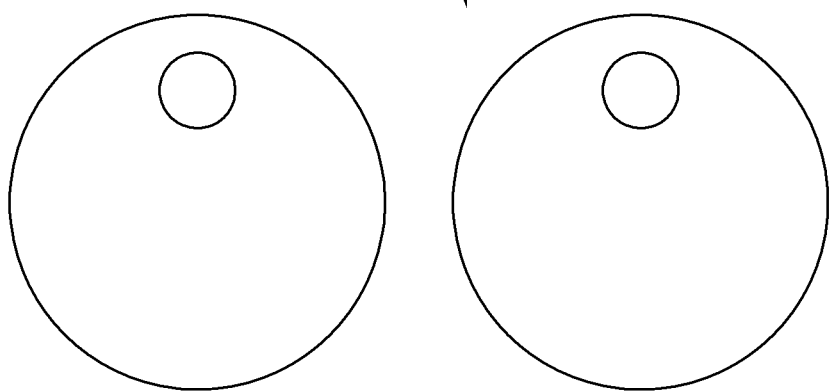

In another embodiment, the retaining interface 78 extends only partially through the prosthesis 72. The retaining interface 78 may be located generally in the center of the prosthesis, or it may be located eccentrically, as depicted in FIGS. 22A and 22B. In one embodiment, shown in FIGS. 23A and 23B, the retaining interface 78 is located at the edge 86 of the prosthesis 76 such that the interior surface of the hole 78 is contiguous with the outer edge of the prosthesis. This configuration of the retaining interface 78 does not require the cable 72 to be threaded through the retaining interface 78 and may facilitate engagement of the retaining member with the prosthesis. FIGS. 24A and 24B depict an embodiment of the invention comprising a two-part prosthesis 88. Either a single cable or two separate cables may be used retain both discs within the facet joint. FIGS. 25A and 25B depict another embodiment of the invention comprising a curved prosthesis 90 with a retaining interface 78 adapted to accept a cable.

Figure 27A:
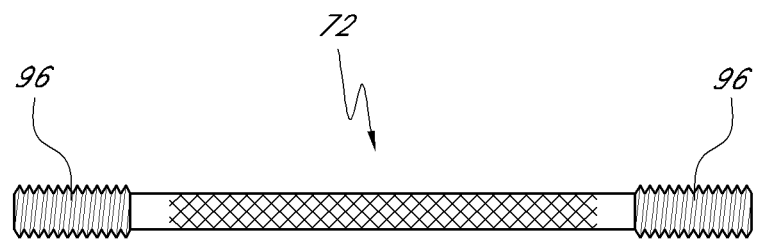
FIGS. 27A and 27B depict another embodiment of the retaining member comprising a braided cable with threaded ends adapted to accept threaded nuts.
Figure 27B:
Figure 28:
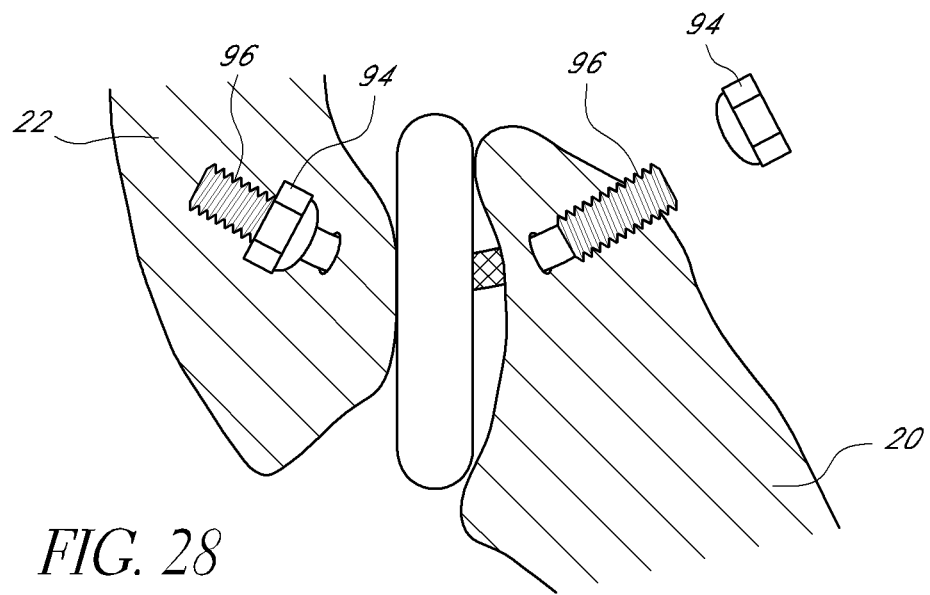
FIG. 28 depicts one embodiment of the invention where a cable is engaged to the articular processes using nuts threaded onto the cable.

In FIG. 26, the wire or cable 72 is secured to the articular processes 20, 22 by tying one or more knots 92 in the cable 72 that can resist pulling of the wire or cable through the articular process. In another embodiment, one or both ends of the wire or cable are provided with an anchor to resist migration of the implants. As shown in FIGS. 27A and 27B, one or both ends of the wire or cable 72 may be threaded such that a nut 94 can be tightened on the wire or cable 72 to secure the wire or cable to the articular processes 20, 22. FIG. 28 depicts the attachment of a nut onto a threaded end of a cable. The threaded portion 96 of the wire or cable can be secured to the cable by pressing, crimping or twisting the threaded 96 portion onto the cable 72. In one embodiment, the threaded portion 96 is made from titanium, titanium alloy, cobalt chromium, stainless steel, or any combination thereof. In one embodiment, the wire or cable has two threaded ends 96 for engaging the bony or cartilaginous tissue, one portion for each facet of the facet joint.

Figure 29:
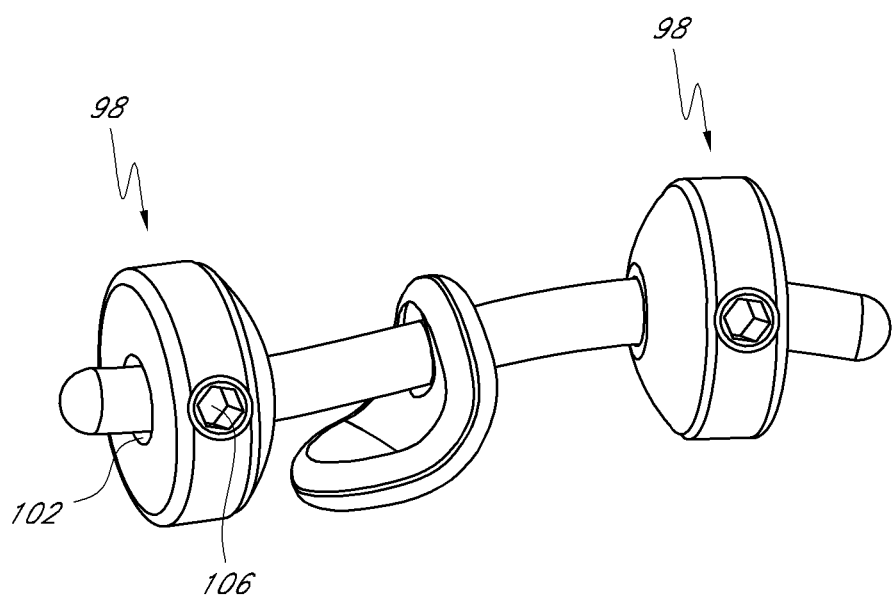
FIG. 29 depicts a preferred embodiment of the invention comprising a curved prosthesis, cable and two set-screw retaining rings.
Figure 30A:
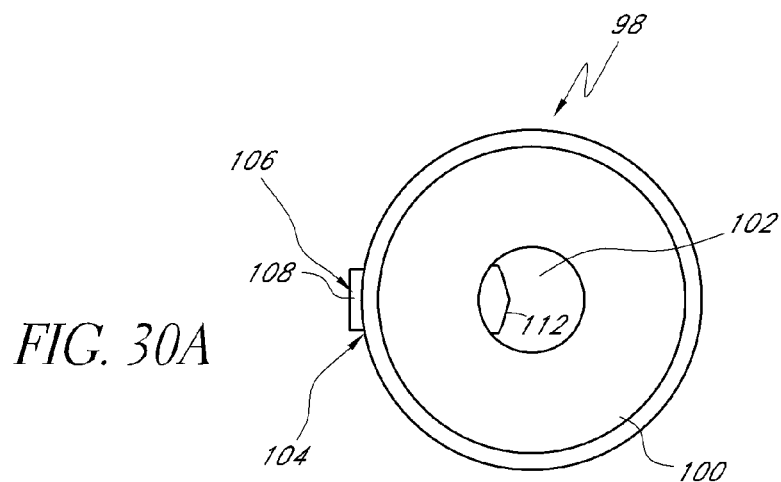
FIGS. 30A and 30B are elevational and cross-sectional views of one embodiment of the set-screw retaining rings, respectively.
Figure 30B:
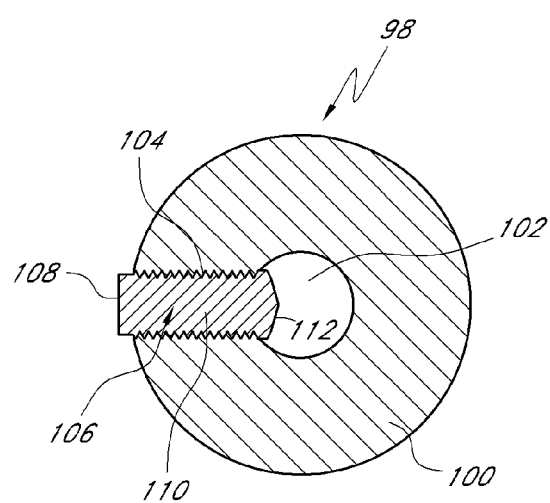
Figure 31:
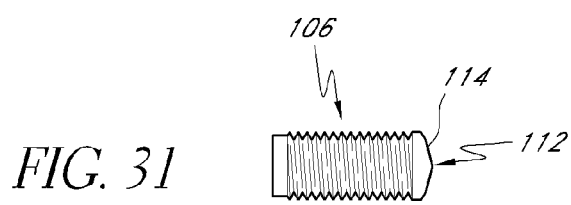
FIGS. 31 through 33 are elevational views of various embodiments of the screw in the set-screw retaining rings.
Figure 32:
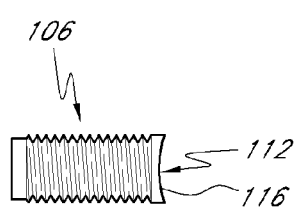
Figure 33:
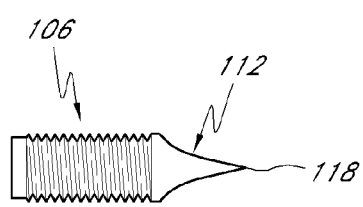

In another embodiment, shown in FIG. 29, the wire or cable is secured to the articular process with retaining rings 98. As depicted in FIGS. 30A and 30B, the retaining rings 98 comprise a ring 100 with a central lumen 102 and a locking element to facilitate locking the ring 100 to a retaining member. The central lumen 102 is adapted to accept insertion of a wire or cable through it. The illustrated locking element is in the form of a side lumen 104 which is threaded and configured to accept a rotatable screw 106 with a proximal end 108, a threaded body 110 and a distal end 112. The threaded body 110 is complementary to the threads of the side lumen 104 so that when the screw 106 is rotated at its distal end 112, the proximal end 108 of the screw 106 moves further into the central lumen 102 and is capable of applying increasing force to a wire or cable inserted through the central lumen 102. In one embodiment, the force on the wire or cable is capable of creating a friction fit or a mechanical interfit to resist movement between the wire or cable and the retaining ring 98, thereby securing the wire or cable to the articular process 20 or 22. As shown in FIGS. 31 to 33, the distal end 112 of the screw 106 can be configured to engage the wire or cable in any of a variety designs, including but no limited to a blunt tip 114, curved tip 116 and piercing tip 118.

In another embodiment, depicted in FIGS. 34A and 34B, the wire or cable is securable to the articular process with a retaining ring 120 have radially inward biased projections 122 defining a central lumen 124. The central lumen has a cross-sectional shape smaller than that of the wire or cable but is capable of enlargement when the inward projections 122 are bent away, as shown in FIGS. 35A and 35B. The inward projections 122 apply increasing force to the wire or cable within the central lumen 124 as the projections 122 are bent, thereby creating a friction fit.

In one embodiment of the invention, one end of the wire or cable retaining member is preformed with a retainer for engaging the articular process. The retainer may be a preformed ring, bulb, flared end, T-bar end, or any of a variety of shapes having a greater cross sectional area than the other portions of the wire or cable retaining member. This configuration of the wire or cable retaining member is adapted to engage an articular process by passing the free end of a wire or cable retaining member through an articular process such that the end with the preformed retainer can engage the articular process.

Figure 36A:
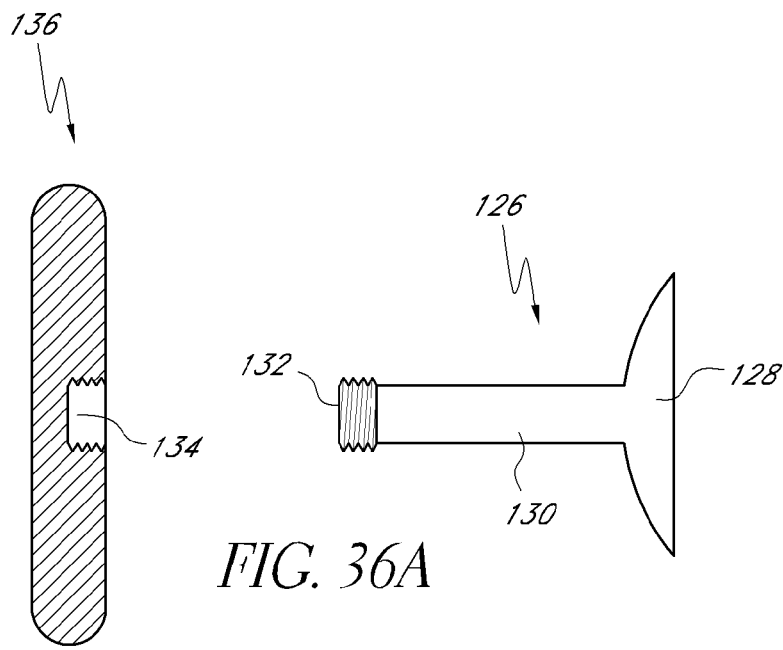
FIGS. 36A to 36C illustrate embodiments of the invention comprising a prosthesis with a close-ended threaded retaining interface and a threaded retaining member.
Figure 36B:
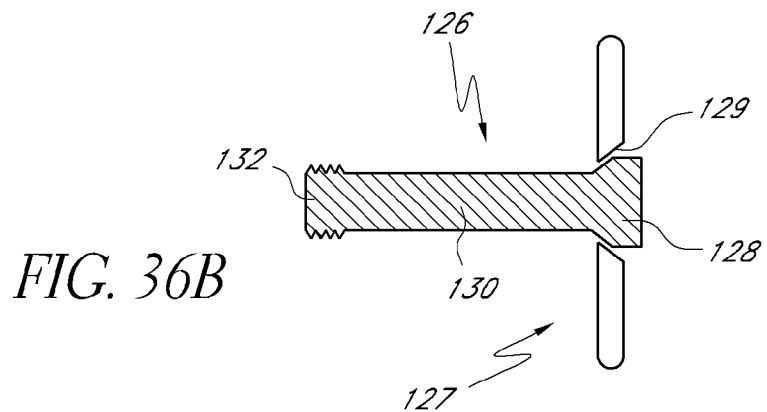
Figure 36C:
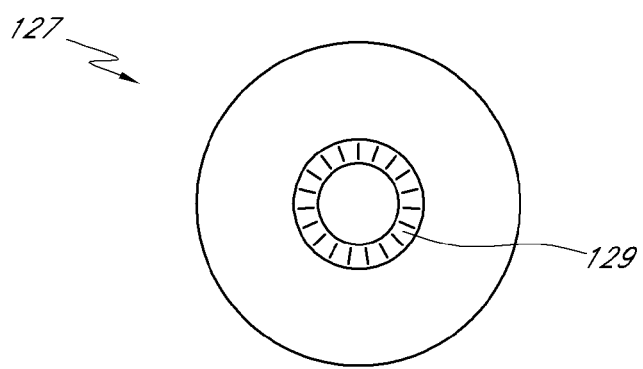

In one embodiment, the wire or cable retaining member is secured to the articular processes with sufficient laxity or length between the secured ends or between the prosthesis and one secured end so that the two articular processes are not fixed in position relative to each other and remain capable of performing movements such as flexion, extension, lateral flexion and/or rotation. In one embodiment, the retaining member comprises a cable of braided polymer, including but not limited to a braided polymer such as PEEK or PEKK, or a braided metal, such as braided cobalt chromium or titanium. The cable can be selected with different degrees of flexibility to provide different degrees of movement at that facet joint. The cable has a first segment capable of engaging the prosthesis at its retaining interface to limit the movement 2. Screw/Bolt Retaining Member In one embodiment of the invention, shown in FIG. 36A, the retaining member comprises a screw or bolt 126 with a proximal end 128, body 130 and distal end 132. The distal end 132 of the screw or bolt is capable of forming a mechanical interfit with a complementary retaining interface 134 on the prosthesis or spacer 136. The distal end 132 typically comprises threads, but one skilled in the art will understand that other configurations may be used to form a mechanical interfit. The complementary retaining interface 134 on the prosthesis 136 could be a threaded through hole or preferably, a close-ended hole. The proximal end 128 of the screw or bolt 126 has a hex or other type of interface known in the art, capable of engaging a rotating tool to manipulate the screw or bolt 126. The body of the screw or bolt 126 has a length sufficient to at least span the length of the hole or conduit created through the articular process for securing the prosthesis. In FIG. 36B, the retaining member further comprises a pivotable washer 127 with a pivot surface 129 that articulates with the proximal end 128 of the screw 126. In one embodiment, the pivotable washer 127 is capable of a range of positions relative to the screw 126 and provides the screw 126 with a better surface area contact with the bone.

Figure 37A:
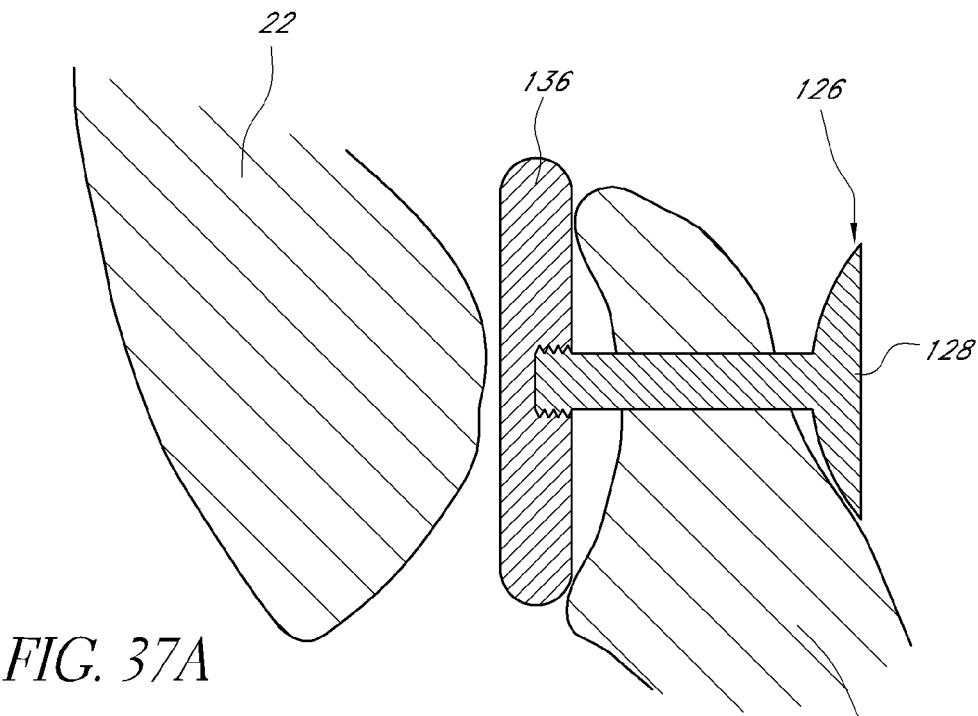
FIG. 37A is a cross sectional view of the prosthesis in FIG. 36A implanted in a facet joint.
Figure 37B:
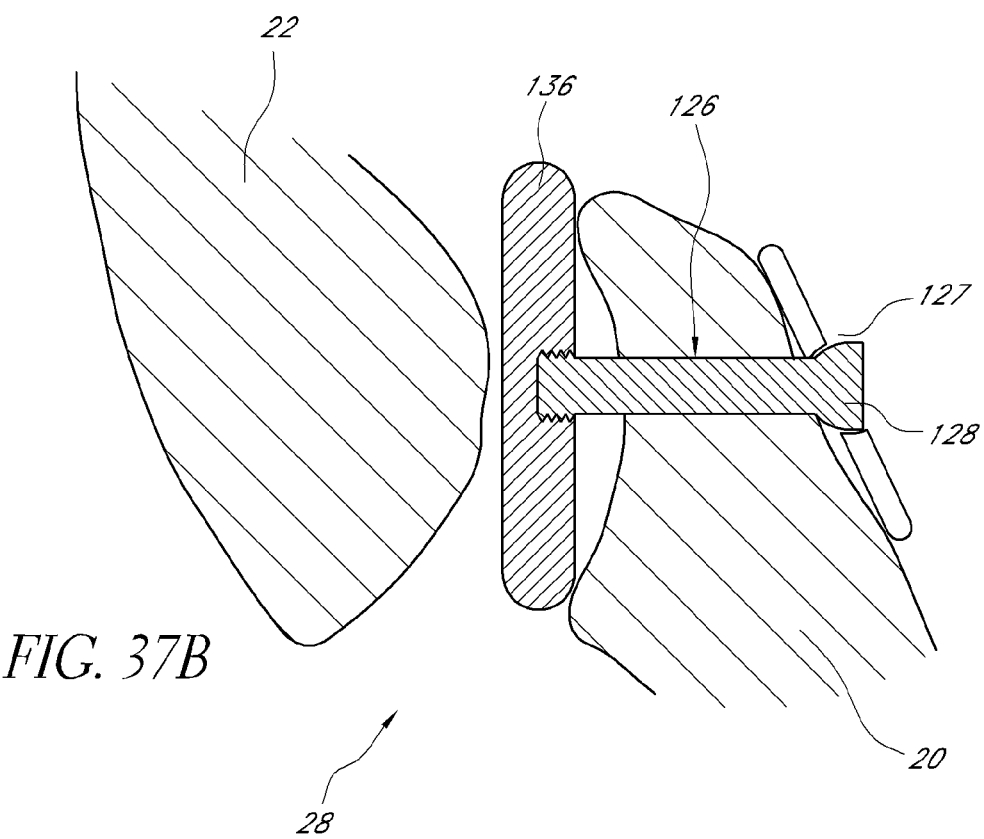
FIG. 37B is a cross sectional view of the prosthesis in FIG. 36B implanted in a facet joint.
Figure 38:
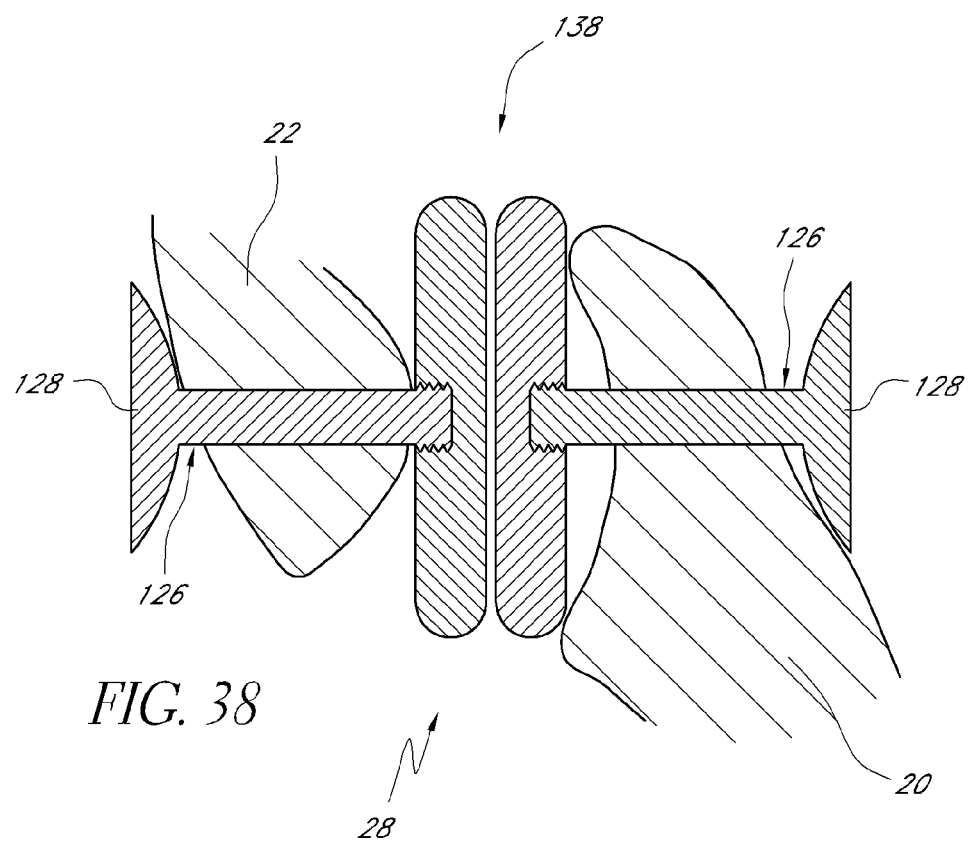
FIG. 38 is a cross sectional view of a two-part prosthesis comprising flat discs implanted into a facet joint.
Figure 39:
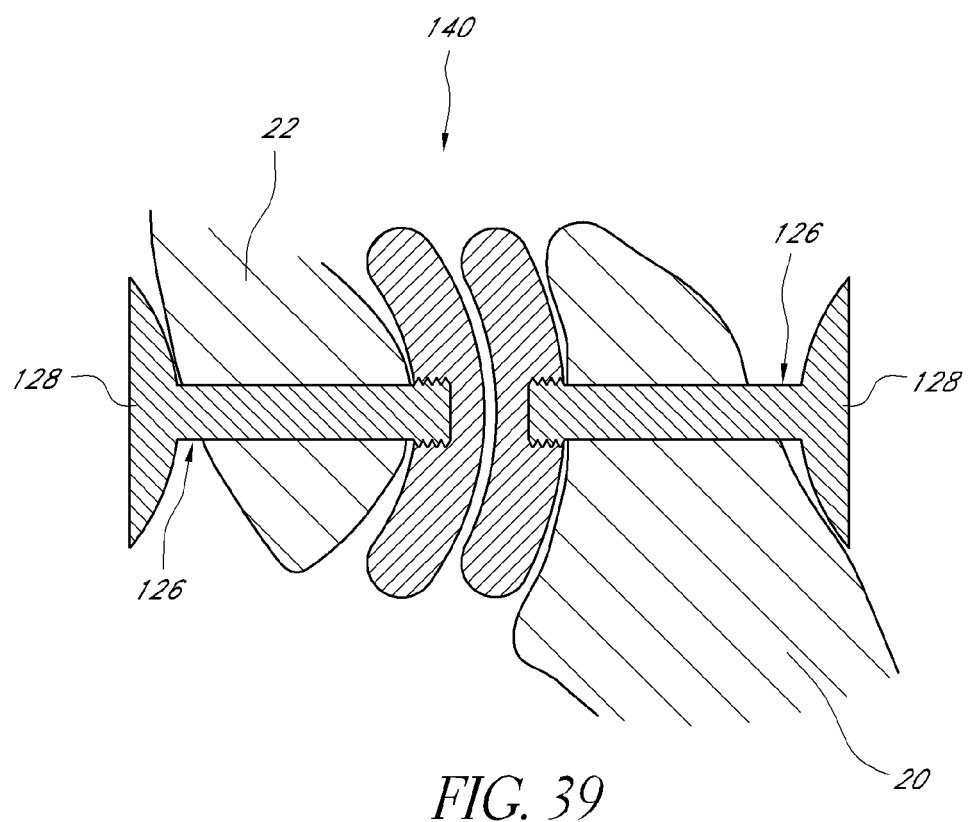
FIG. 39 is a cross sectional view of a two-part prosthesis comprising curved discs implanted into a facet joint.

FIG. 37 is a cross-sectional view of a facet joint 28 with a spacer 136 bolted to one articular process 20 of a facet joint 28. The spacer 136 position is fixed relative to one facet 24 of the joint 28, but provides for spacing and movement of the other facet 26 with respect to the spacer 136. In embodiments of the invention comprising a two-part prosthesis, shown in FIGS. 38 and 39, each disc may have its own screw or bolt retaining member. FIG. 38 depicts a flat two-part prosthesis 138 and FIG. 39 depicts a curved two-part prosthesis 140.

3. Projection Retaining Member

Figure 42:
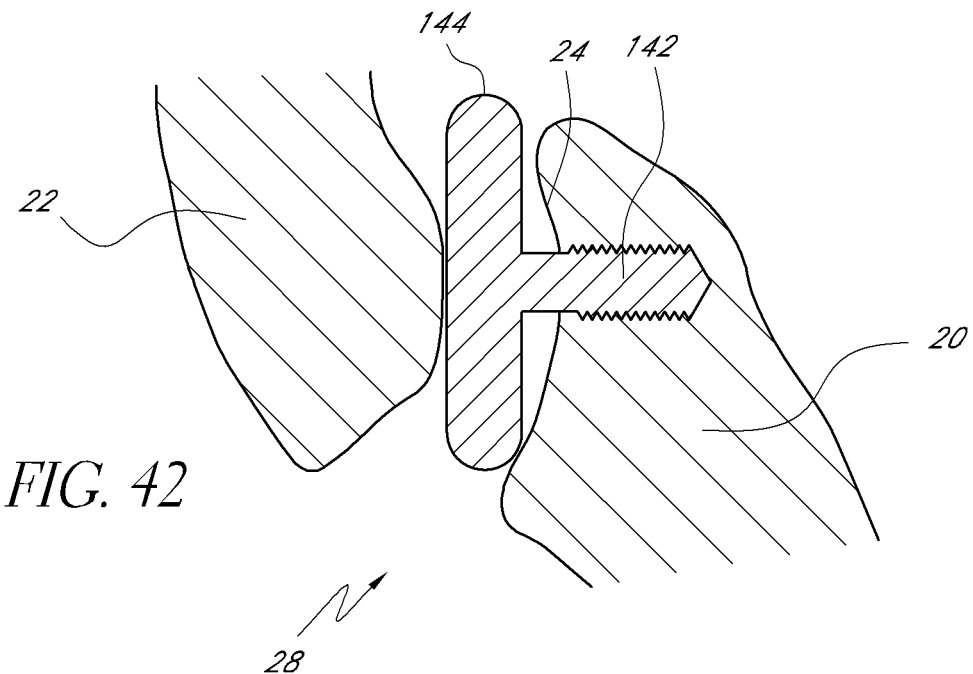
FIG. 42 depicts the prosthesis of FIG. 38A implanted into a facet joint.
Figure 43:
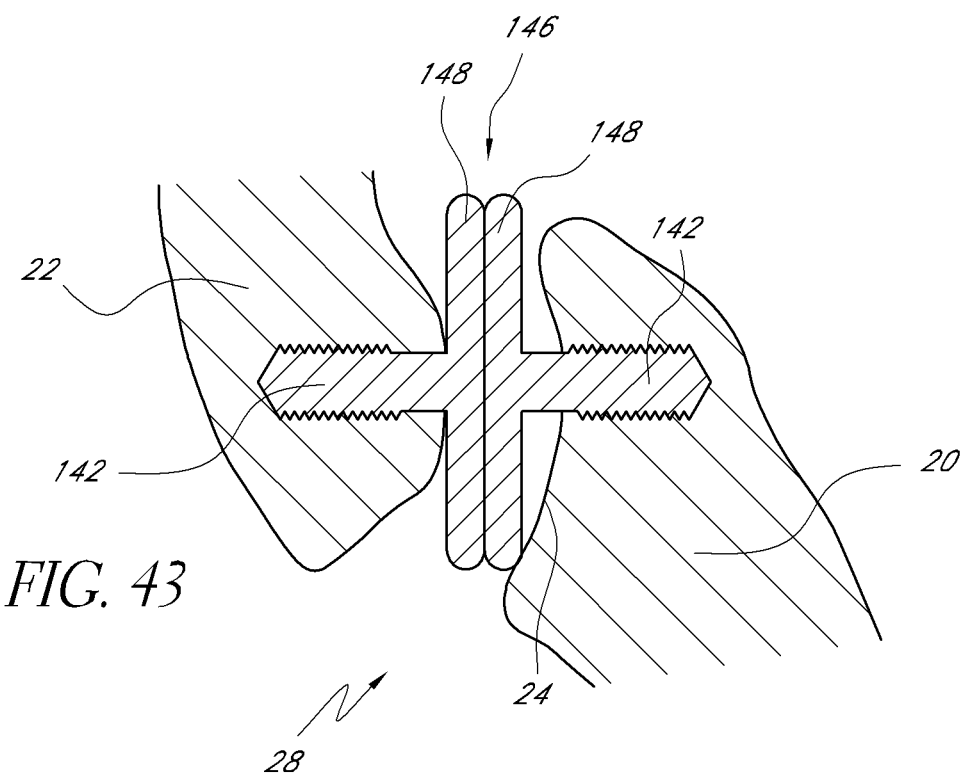
FIG. 43 illustrates a two-part prosthesis implanted into a facet joint.
Figure 44:
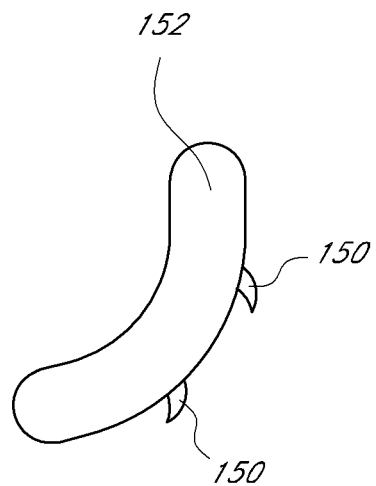
FIG. 44 shows one embodiment of the invention comprising a prosthesis with multiple anchoring projections.
Figure 45:
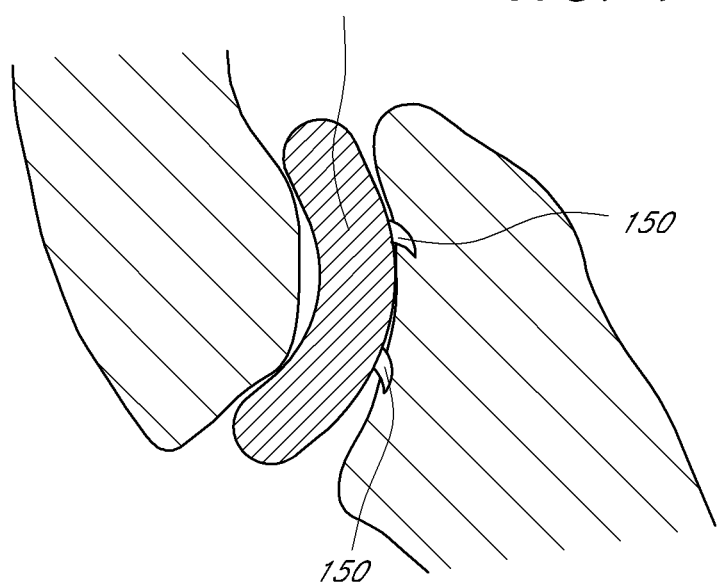
FIG. 45 shows the prosthesis of FIG. 44 implanted into a facet joint.
Figure 46A:
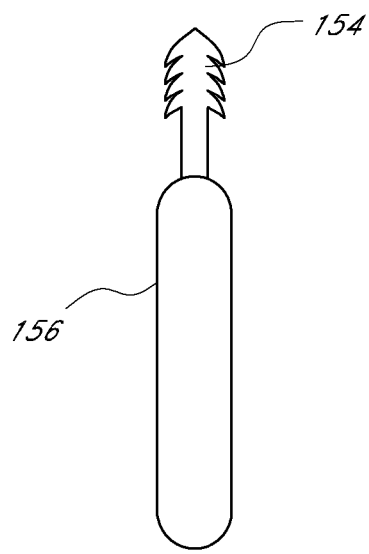
FIGS. 46A and 46B depict one embodiment of the invention comprising a prosthesis with a rigid soft tissue side anchor.
Figure 46B:
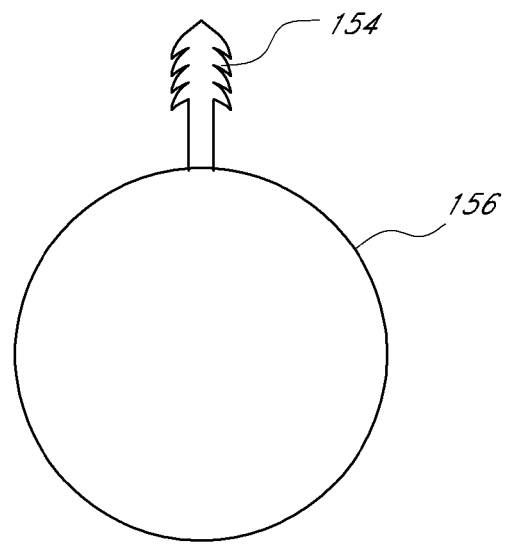

In some embodiments of the invention, shown in FIGS. 40A through 41B, the retaining member is integral with or attached to the prosthesis and comprises a projection 142 from the prosthesis 144 that is adapted to engage the adjacent articular process or surrounding tissue. In one embodiment, the projection comprises at least one spike 142 or hook projecting from one face of the prosthesis 144. In one embodiment, the spike 142 or hook can be ribbed, barbed or threaded to resist separation after insertion into bone or tissue. FIG. 42 depicts the prosthesis 144 of FIG. 40A engaged to a facet 24 of the facet joint 28. In one embodiment comprising a two-part prosthesis 146, shown in FIG. 43, each disc 148 may have its own projection-retaining member 142. In some embodiments of the invention, as depicted in FIG. 44, more than one projection 150 is provided on the prosthesis 152. FIG. 45 illustrates the prosthesis of FIG. 44 placed in a facet joint 28. The projections 150 may be angled with respect to the prosthesis 152 to resist dislodgement by the movement at the joint.

Figure 47A:
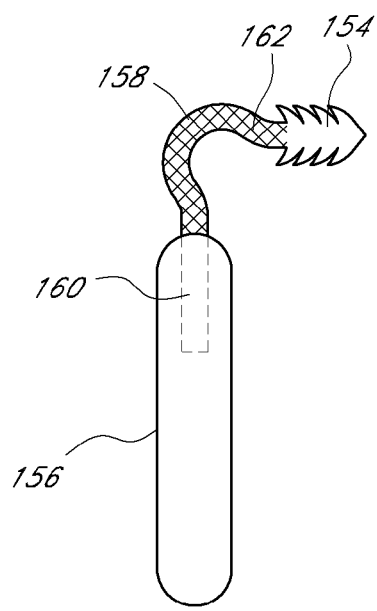
FIGS. 47A and 47B depict one embodiment of the invention comprising a prosthesis with an embedded flexible soft tissue side anchor.
Figure 47B:
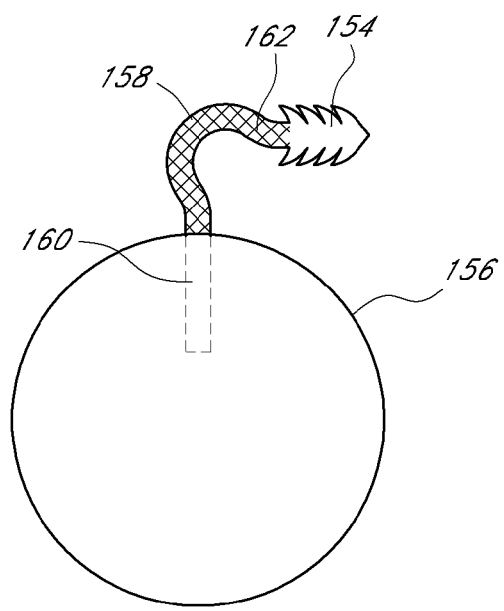

FIGS. 46A to 47B illustrate embodiments of the invention where the retaining member comprises a projection 154 extending laterally such as from the side of the prosthesis 156, and adapted to engage the soft tissue surrounding the facet joint, rather than a bony or cartilaginous articular process. In one example, the prosthesis of FIG. 46 could be inserted into a facet joint through an incision made in the joint capsule, but the integrity of the joint capsule opposite the incision site is maintained and used as an anchoring site for the prosthesis. The orientation of the projection can be fixed as in FIG. 44, or flexible. FIG. 47 depicts a flexible tether such as a wire 158 with its proximal end 160 embedded in or otherwise attached to the prosthesis and one or more barbs which may be attached to its distal end 162. A flexible projection may provide greater selection of soft tissue anchoring sites for the prosthesis.

In one embodiment of the invention, the joint capsule is closed after placement of the prosthesis. Closure may be performed using adhesives, suturing, stapling or any of a variety of closure mechanisms known in the art.

E. Accessing the Facet Joints

1. Surgical Approach to the Cervical Spine

Figure 48:
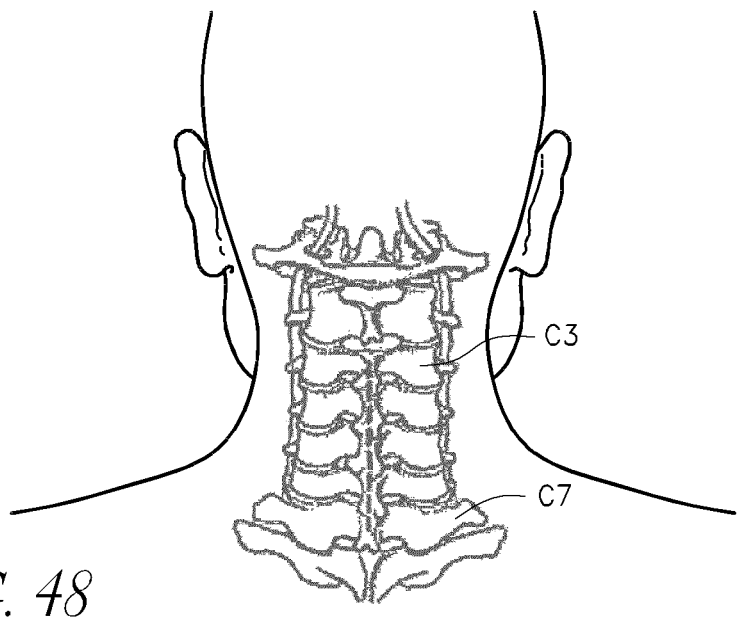
FIG. 48 depicts one embodiment of the invention depicting a posterior surgical approach for implanting a prosthesis in the cervical vertebrae.
Figure 49:
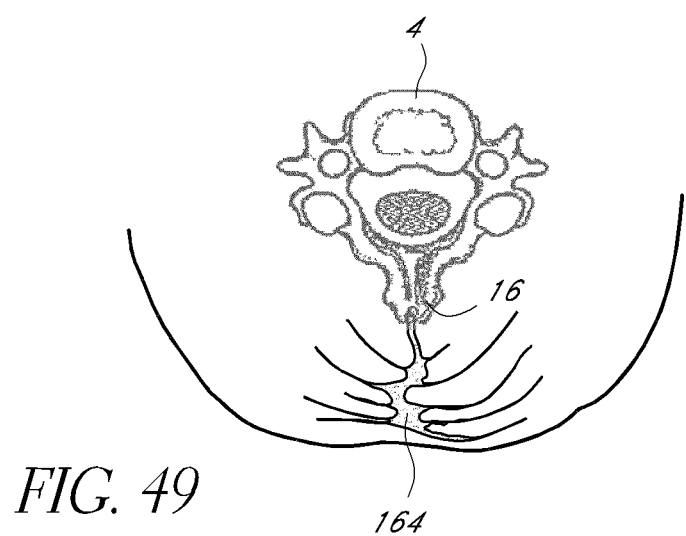
FIG. 49 depicts one embodiment of the invention depicting the cross-sectional surgical approach for implanting a prosthesis in the cervical vertebrae.

In one embodiment of the invention, general anesthesia is achieved and the patient is positioned prone on a turning frame or three-point head rest attached to the table. Skeletal traction is performed using tongs. The patient is prepped and draped in the usual sterile fashion. Pre-operative radiographic films are reviewed and any vertebral anomalies or variations are noted. In one embodiment, the spinous processes are palpated to identify the location of the cervical vertebrae and a skin incision is made over the desired vertebrae, as shown in FIG. 48. In another embodiment, a paraspinous skin incision is made over the desired facet joint. The exposed skin edges and subcutaneous tissue are injected with epinephrine 1:500,000 solution to facilitate hemostasis. Dissection to the spinous processor facet joint is performed using an electrocautery knife. In one embodiment, shown in FIG. 49, dissection is performed along the nuchal ligament 164 to avoid cutting into vascular muscle tissue. Soft tissue retractors are used to maintain tissue tension and aid the dissection process. The ligamentous attachments to the spinous process 16 are detached and the facet joints are exposed. In another embodiment, dissection is performed through the muscle tissue to directly access the facet joint. The joint capsule of the facet joint is opened by incision or piercing. The facets of the facet joint are distracted as required to provide access to the joint space. In one embodiment, the affected facet joint is sized and a joint prosthesis is selected. In one embodiment, the articular process or processes are prepared for receiving the joint prosthesis, including but not limited to roughening the articular surface of the articular process and/or creating a hole for the prosthesis anchor or retaining member. The prosthesis is inserted into the facet joint space and the anchor or retaining member, if any is attached to the articular process. The steps are repeated until all the joint prostheses have been inserted. The surgical site is closed in layers with a suction tube or drainage tube in place. The surgical site is cleaned and dressed.

2. Surgical Approach to the Thoracic Spine

Figure 50:
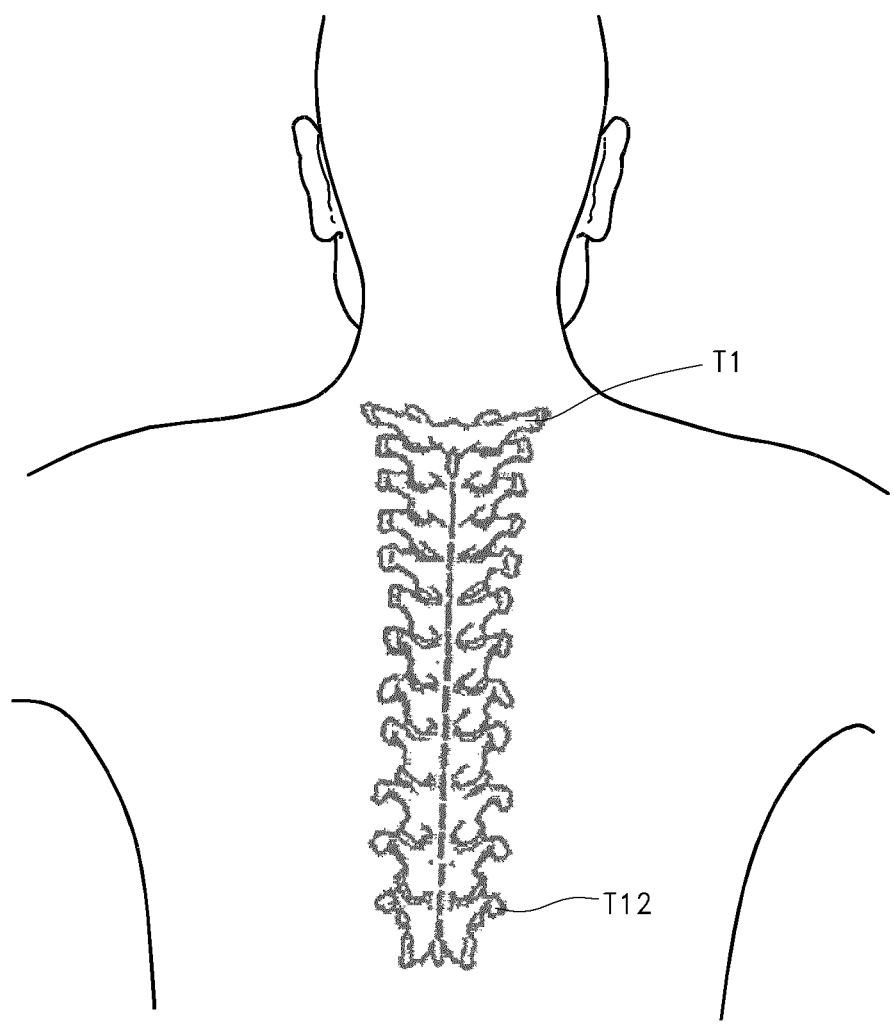
FIG. 50 depicts one embodiment of the invention depicting a posterior surgical approach for implanting a prosthesis in the thoracic vertebrae.

In one embodiment of the invention, general anesthesia is achieved and the patient is positioned prone on a padded spinal operating frame. The patient is prepped and draped in the usual sterile fashion. Pre-operative radiographic films are reviewed and any vertebral anomalies or variations are noted. In one embodiment, shown in FIG. 50, a midline skin incision is made over the desired vertebrae. In another embodiment, a paraspinous skin incision is made over the desired facet joint. The exposed skin edges, subcutaneous tissue and erector spinae muscles are injected with epinephrine 1:500,000 solution to facilitate hemostasis. Dissection is performed using an electrocautery knife or scalpel through the superficial and lumbodorsal fascia to the tips of the spinous processes. The erector spinae muscle is reflected laterally to the tips of the transverse processes, thereby exposing the posterior arch. After exposure of all the desired vertebrae is achieved, an intra-operative x-ray is obtained to confirm access to the desired vertebrae. The facets of the facet joint are distracted as required to provide access to the joint space. The joint capsule of the facet joint is opened by incision or piercing. In one embodiment, the affected facet joint is sized and a joint prosthesis is selected. In one embodiment, the articular process or processes are prepared for receiving the joint prosthesis, including but not limited to roughening the articular surface of the articular process and/or creating a hole for the prosthesis anchor or retaining member. The prosthesis is inserted into the facet joint space and the anchor or retaining member, if any is attached to the articular process. The steps are repeated until all the joint prostheses have been inserted. The surgical site is closed in layers with a suction tube or drainage tube in place. The surgical site is cleaned and dressed.

3. Surgical Approach to the Lumbar Spine

Figure 51C:
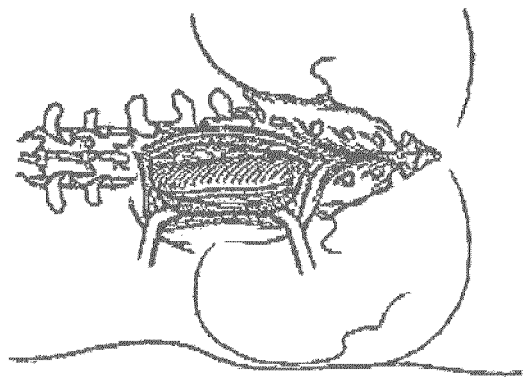
FIGS. 51A to 51E depicts one embodiment of the invention depicting a posterior surgical approach for implanting a prosthesis in the lumbar vertebrae.
Figure 51B:
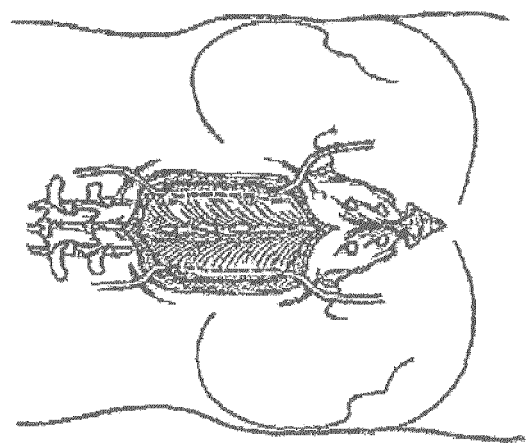
Figure 51A:
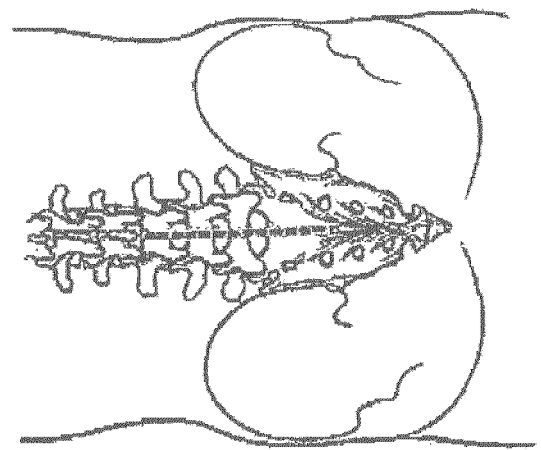
Figure 51E:
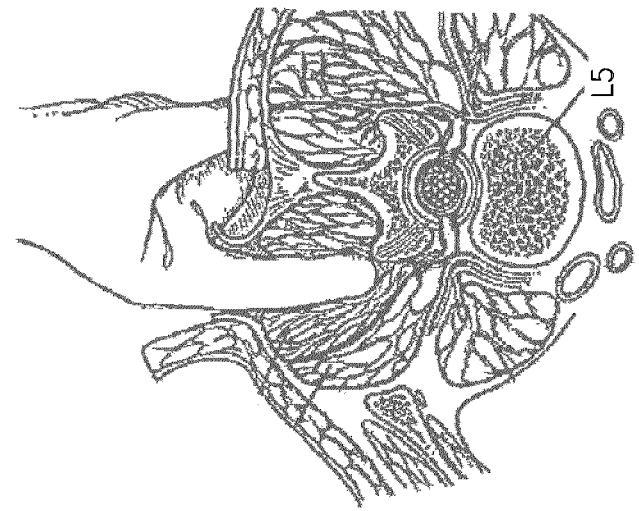
Figure 51D:
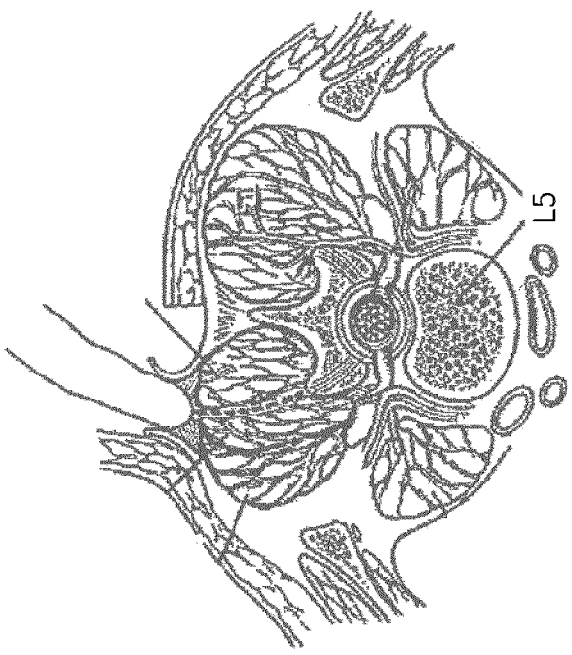

In one embodiment of the invention, general anesthesia is achieved and the patient is positioned prone or kneeling on a padded spinal operating frame. In one embodiment, by allowing the abdomen to hang free, intravenous pressure is reduced and blood loss during the procedure is decreased. The patient is prepped and draped in the usual sterile fashion. Pre-operative radiographic films are reviewed and any vertebral anomalies or variations are noted. FIG. 51A illustrates a midline skin incision is made over the desired vertebrae. The exposed skin edges and subcutaneous tissue are injected with epinephrine 1:500,000 solution to facilitate hemostasis. In FIGS. 51B and 51C, dissection is continued to the lumbodorsal fascia and the surgical site is exposed by retracting the skin and subcutaneous tissue laterally. In FIGS. 51D and 51E, blunt finger dissection is used between the multifidus and longissimus muscles to access the facet joints. Self-retaining Gelpi retractors are inserted between the muscle groups. Electrocautery or elevators are used to separate the transverse fibers of the multifidus from their heavy fascial attachments. Exposure of the transverse processes and fascial planes is continued. Cautery may be used to provide hemostasis from the lumbar arteries and veins along the base of the transverse processes. The facets of the facet joint are distracted as required to provide access to the joint space. The joint capsule of the facet joint is opened by incision or piercing. In one embodiment, the affected facet joint is sized and a joint prosthesis is selected. In one embodiment, the articular process or processes are prepared for receiving the joint prosthesis, including but not limited to roughening the articular surface of the articular process and/or creating a hole for the prosthesis anchor or retaining member. The prosthesis is inserted into the facet joint and the anchor or retaining member, if any is attached to the articular process. The steps are repeated until all the joint prostheses have been inserted. The surgical site is closed in layers over a suction tube and the skin flaps are sutured down to the fascia to eliminate any dead space in the tissue. The surgical site is cleaned and dressed.

4. Minimally Invasive Approach to the Cervical Spine

In one embodiment of the invention, general or local anesthesia is achieved and the patient is positioned prone on a turning frame or three-point head rest attached to the table. Skeletal traction is performed using tongs. The patient is prepped and draped in the usual sterile fashion. Pre-operative radiographic films are reviewed and any vertebral anomalies or variations are noted. The spinous processes are palpated to identify the location of the cervical vertebrae and a small 1 cm skin incision is made over the desired insertion site. Hemostasis is achieved with infiltration of epinephrine 1:500,000 solution around the incision site. Under fluoroscopy, a trocar or needle is inserted through the incision site and joint capsule to the desired facet joint. The needle or trocar is replaced with an introducer. In one embodiment, insertion is performed along the nuchal ligament to avoid cutting into vascular muscle tissue. In another embodiment, insertion is performed directly through the skin and muscle overlying the facet joint. The facets of the facet joint are distracted as required to provide access to the joint space. In one embodiment, the affected facet joint is sized by injecting a radio-contrast agent into the facet joint and a joint prosthesis is selected. In one embodiment, the articular process or processes are prepared for receiving the joint prosthesis, including but not limited to roughening the articular surface of the articular process and/or creating a hole using endoscopic instruments known in the art. The prosthesis is inserted into the facet joint space through the introducer and an anchor or retaining member, if any is attached to the articular process. The steps are repeated until all the joint prostheses have been inserted. The surgical site is closed, cleaned and dressed.

5. Minimally Invasive Approach to the Thoracic Spine

In one embodiment of the invention, general or local anesthesia is achieved and the patient is positioned prone on a padded spinal operating frame. The patient is prepped and draped in the usual sterile fashion. Pre-operative radiographic films are reviewed and any vertebral anomalies or variations are noted. A small 1 cm skin incision is made over the desired insertion site. Hemostasis is achieved by injecting epinephrine 1:500,000 solution around the incision site. Under fluoroscopy, a trocar or needle is inserted through the superficial and lumbodorsal fascia, the erector spinae muscle and joint capsule to access the facet joint. The trocar or needle is replaced with an introducer. The facets of the facet joint are distracted as required to provide access to the joint space. An intra-operative x-ray or fluoroscopy is obtained to confirm access to the desired facet joint. In one embodiment, the affected facet joint is sized and a joint prosthesis is selected. In one embodiment, the articular process or processes are prepared for receiving the joint prosthesis, including but not limited to roughening the articular surface of the articular process and/or creating a hole for the prosthesis anchor or retaining member, using endoscopic instruments known in the art. The prosthesis is inserted into the facet joint space and the anchor or retaining member, if any is attached to the articular process. The steps are repeated until all the joint prostheses have been inserted. The surgical site is closed, cleaned and dressed.

6. Minimally Invasive Approach to the Lumbar Spine

In one embodiment of the invention, general or local anesthesia is achieved and the patient is positioned prone or kneeling on a padded spinal operating frame. In one embodiment, by allowing the abdomen to hang free, intravenous pressure is reduced and blood loss during the procedure is decreased. The patient is prepped and draped in the usual sterile fashion. Pre-operative radiographic films are reviewed and any vertebral anomalies or variations are noted. A small 1 cm skin incision is made over the desired insertion site. Hemostasis is achieved by injecting epinephrine 1:500,000 solution around the incision site. Under fluoroscopy, a trocar or needle is inserted through the lumbodorsal fascia. The trocar or needle is replaced with an introducer. In one embodiment, radiocontrast agent is injected through the introducer to identify the junction between the lumbodorsal fascia and the multifidus and longissimus muscles. A blunt dissector is inserted through the introducer to dissect between the multifidus and longissimus muscles and pierce the joint capsule to access the facet joints. The facets of the facet joint are distracted as required to provide access to the joint space. In one embodiment, the affected facet joint is sized and a joint prosthesis is selected. In one embodiment, the articular process or processes are prepared for receiving the joint prosthesis, including but not limited to roughening the articular surface of the articular process and/or creating a hole for the prosthesis anchor or retaining member. The prosthesis is inserted into the facet joint space and the anchor or retaining member, if any is attached to the articular process. The steps are repeated until all the joint prostheses have been inserted. The surgical site is closed, cleaned and dressed.

F. Facet Drill

Other embodiments of the invention comprise tools and methods for creating holes or lumens through one or more articular processes of the vertebra to facilitate implantation of a prosthesis stabilizer or retainer. Preferably, the holes or lumens have a curved or non-linear configuration. The curved or non-linear configuration allows relatively greater penetration through the thicker portions of the articular process(es) and therefore the articular process(es) may be less likely to fracture during formation of the hole or lumen. While various instruments have been proposed for drilling into and through bone, including for example, the curved drills described in U.S. Pat. Nos. 5,700,265, 6,419,678, and 6,607,530, herein incorporated by reference in their entirety, the subject tool offers the benefits of lumen formation through the articular processes within the limited surgical access available about the vertebra. The preferred devices utilize one or more curved punch members or curved drills that rotate about an axis that is transverse to the movement plane of the curved punch or curved drill member. Unlike traditional orthopedic procedures that require unimpeded access to the surgical site due to the longitudinally-oriented surgical tools, the curved punch or curved drill members also permit access using a limited space or cavity around the articular processes. As used herein, the terms "lumen-forming" and "lumen formation" refer to the creation of a hole, passageway or indentation generally such as by, for example, piercing, punching, boring, puncturing, or drilling.

Figure 52A:
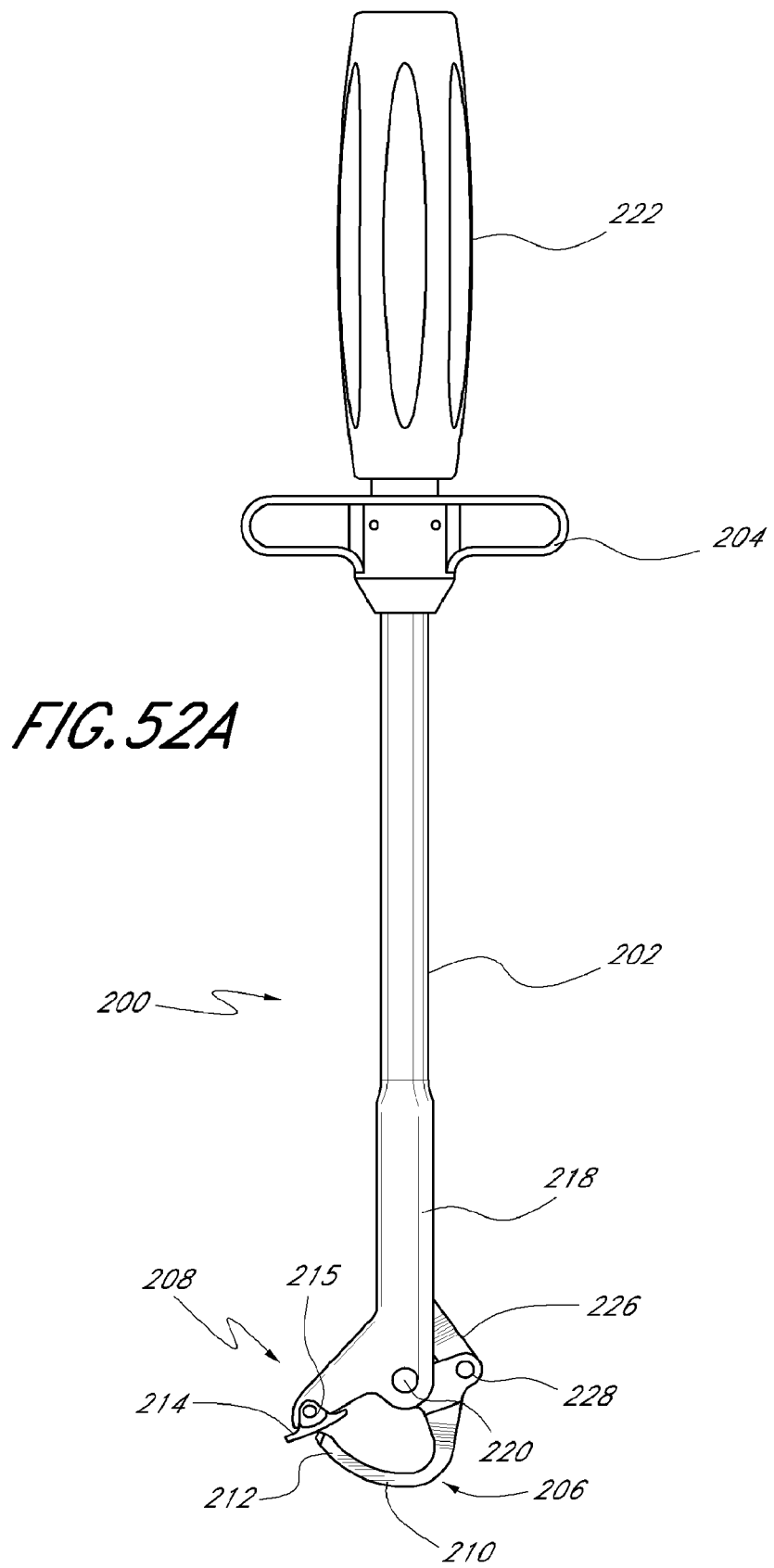
FIGS. 52A to 52E illustrate one embodiment of the tool with a single punch arm and plate.
Figure 52B:
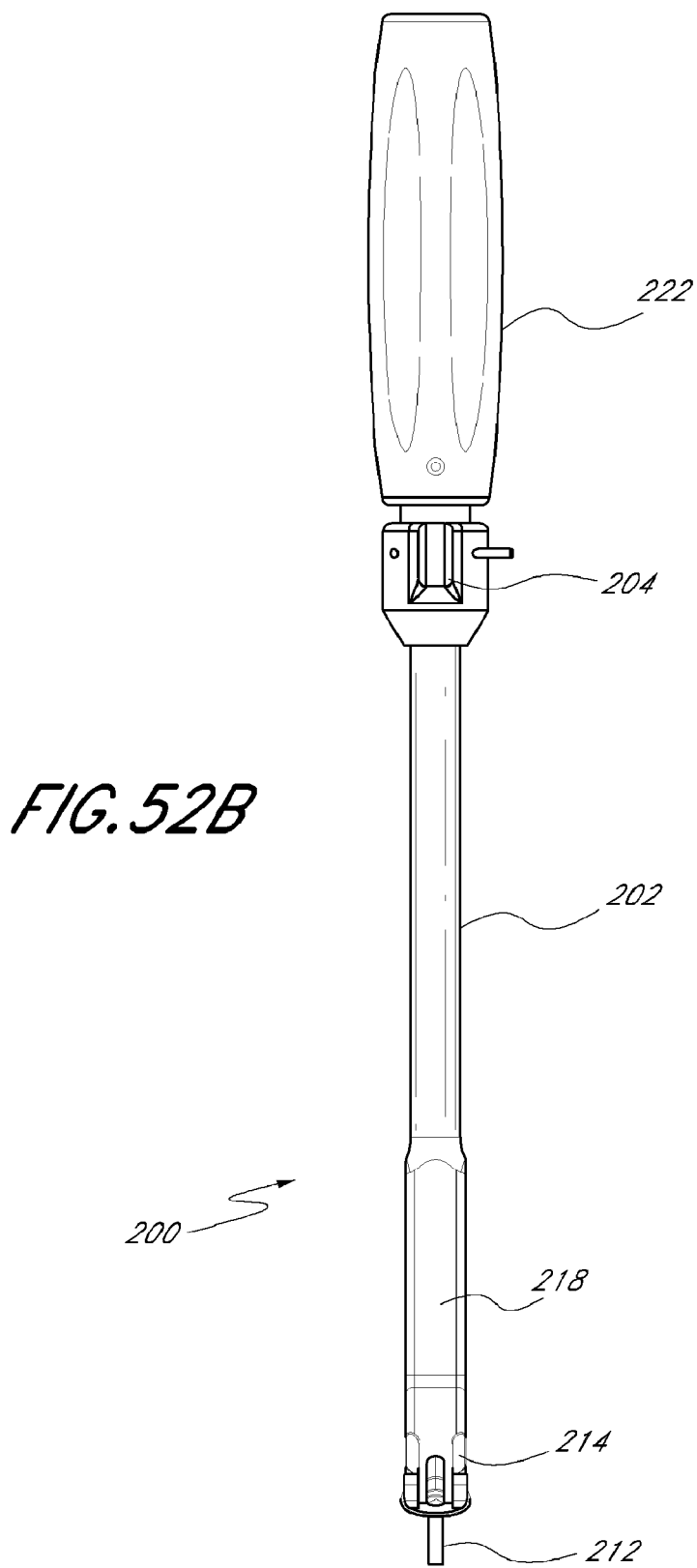
Figure 52C:
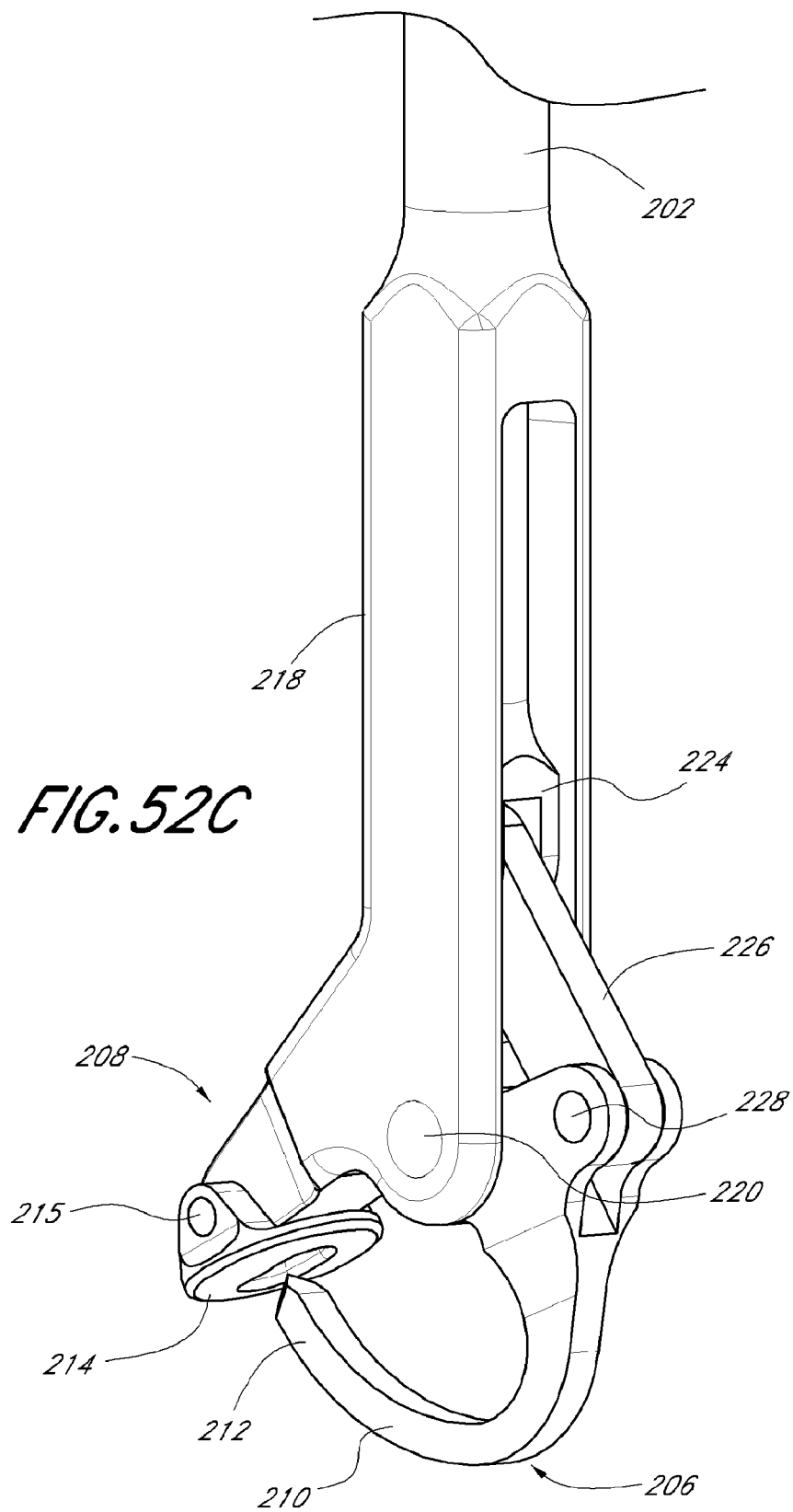
Figure 52D:
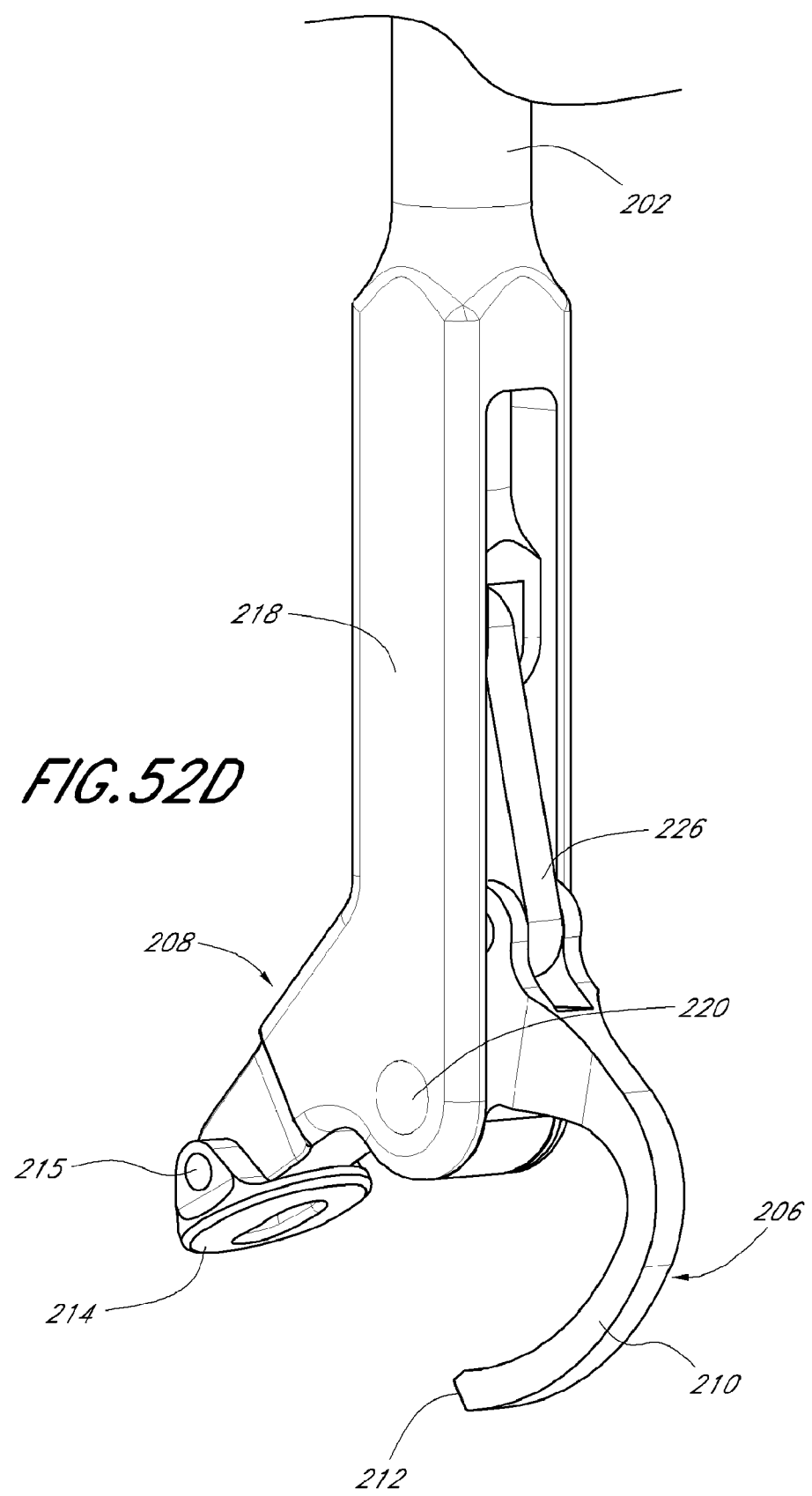
Figure 52E:
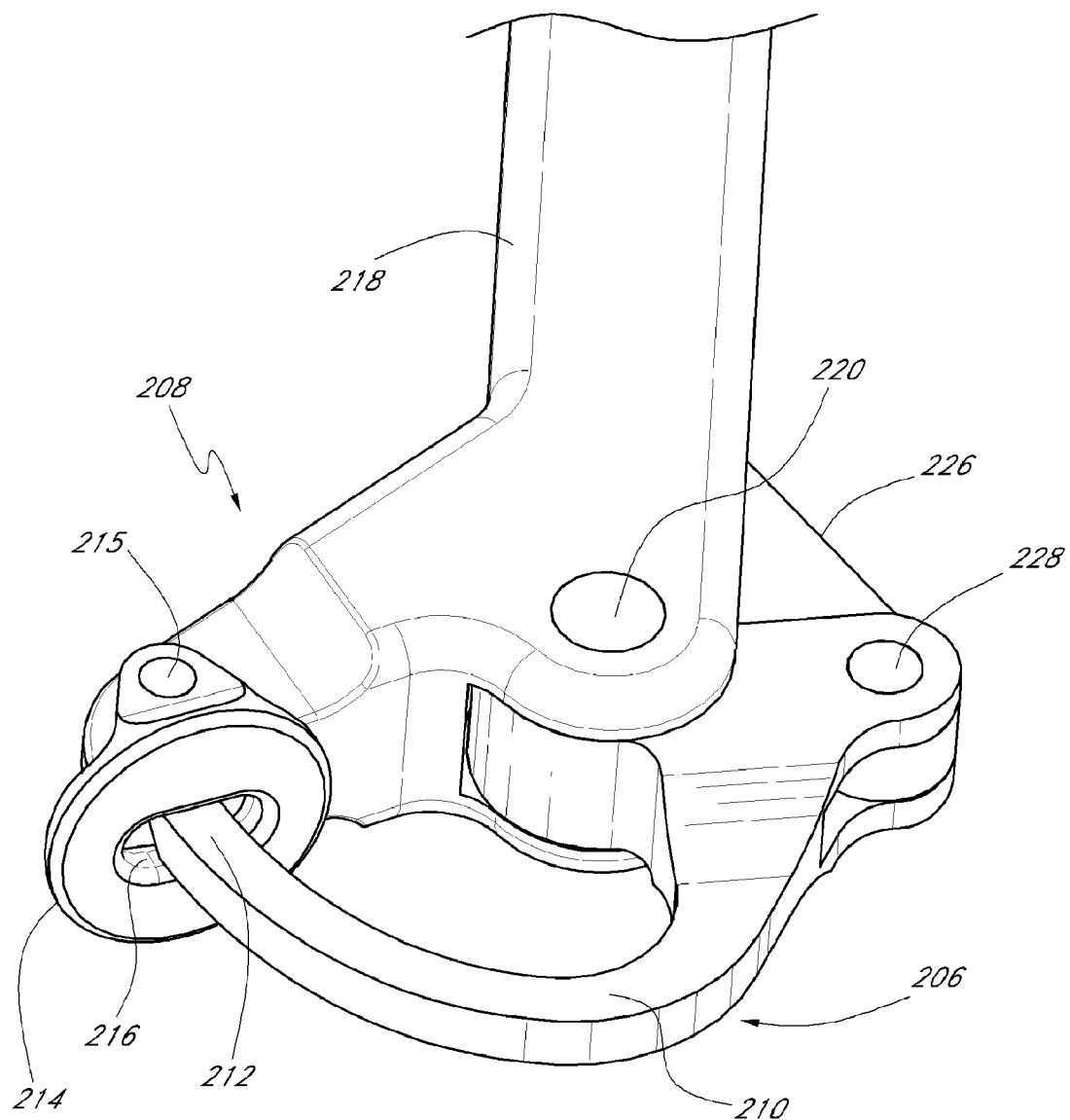
Figure 52F:
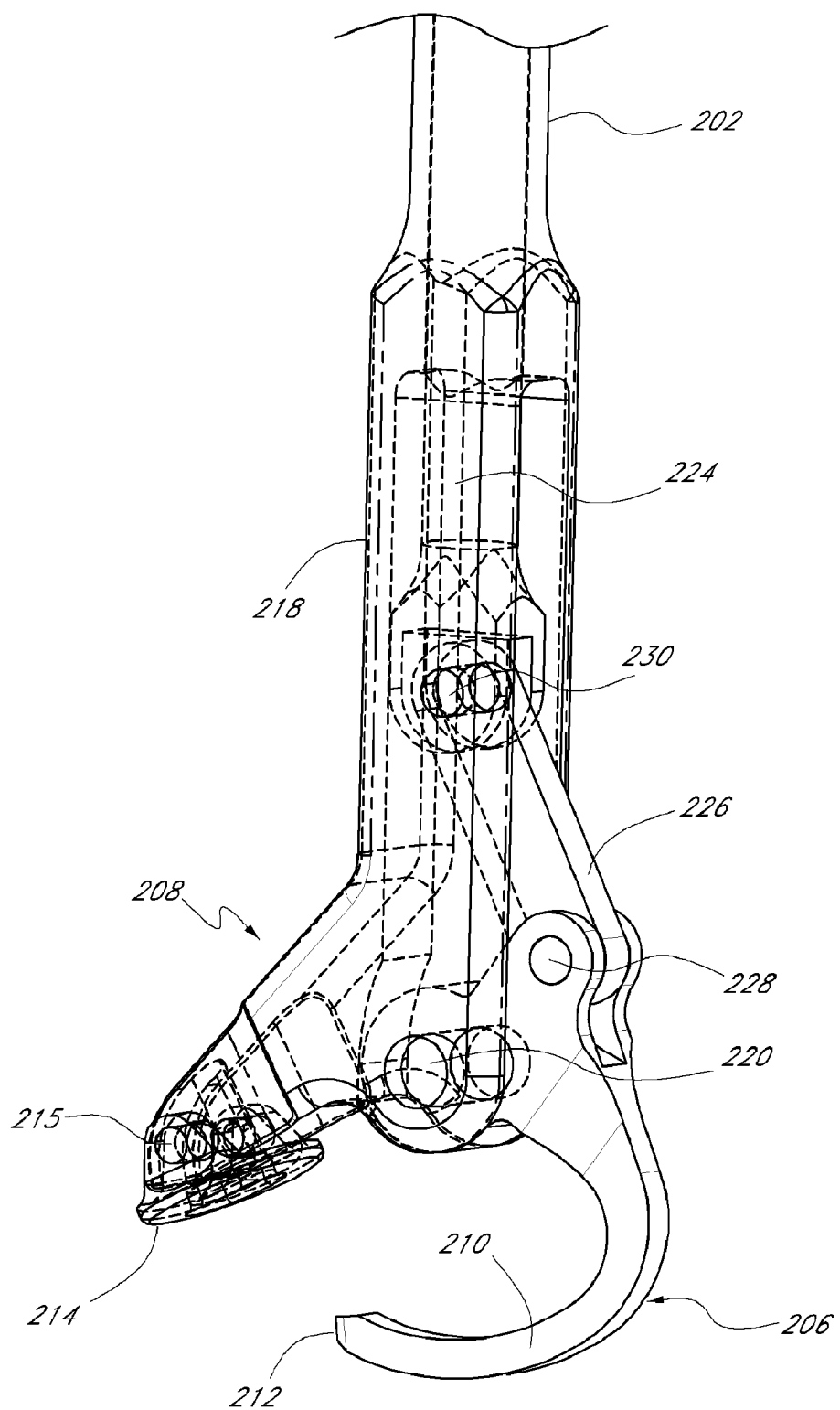
FIG. 52F is a wire frame model of the embodiment depicted in FIGS. 52A to 52E.

One embodiment of the tool 200, shown in FIGS. 52A and 52F, comprises a shaft 202 with a proximal handle 204 and a movable distal lumen-forming member 206 and a distal opposing support member 208. The lumen-forming member 206 may comprise a punch or lumen-forming arm 210 with a punch or lumen-forming tip 212. The arm 210 of the lumen-forming member 206 may have a diameter in the range of about 1 mm to 5 mm, preferably about 2 mm to 4 mm, and most preferably about 3 mm. The lumen-forming tip 212 can be of any appropriate configuration and with any number of points. In some embodiments, the lumen-forming tip 212 may be round, flat, beveled or stepped. In some embodiments of the lumen-forming tool with more than one tip, the tips may have a similar or different configurations.

The support member 208 permits stabilization of the articular processes as the lumen-forming member 206 passes or punctures through the bone. The support member 208 may comprise a plate 214 that is flat or curved. In some embodiments, the plate 214 may have a concave or convex configuration. The plate 214 may optionally comprise a recess 216, depicted in FIG. 52E, to seat the articular process and/or to allow the lumen-forming tip 212 of the lumen-forming member 206 to penetrate through the bone and into the recess 216. The support member 208 may also comprise a textured surface to resist slippage, including but not limited to serrations, ridges or indentations, or comprise a slip-resistant material. In some embodiments of the lumen-forming tool 200, as depicted in FIG. 52E, the support member 208 comprises a movable opposing plate 214. The movable opposing plate 214 may be connected by any of a variety of movable joints known in the art. For example, in the embodiment depicted in FIG. 52F, the plate 214 is connected to rest of the support member 208 with a pivot pin 215. In other embodiments, ball-and-socket joints may be used. The movable opposing plate allows increased conformance or seating of the tool against the articular process. In some embodiments, the movable opposing plate 214 pivots passively as the tool 200 is applied to the bone. In other embodiments, the position or orientation of the movable opposing plate 214 may be controlled at the proximal end of the tool 200. Manipulation of the plate may be performed using push/pull rods, gears pull wires or combinations thereof, as is known to those of skill in the art. The plate may be biased in a particular orientation using springs or other bias structures.

Referring to FIGS. 52C to 52F, the lumen-forming member 206 may be movably attached and secured to the distal frame 218 of the shaft 202 by a pivot pin 220. The lumen-forming member 206 may be moved between a closed configuration, depicted in FIG. 52C, to an open configuration, depicted in FIG. 52D, by a proximal actuator 222 that moves a control rod 224 within the shaft 202 of the tool 200. In the embodiment depicted in FIGS. 52C to 52F, manipulation of the actuator 222 causes a longitudinal movement of the control rod 224, which in turn causes a translational/angular movement of a link member 226 joining the control rod 224 and lumen-forming member 206 using pivot pins 228, 230. The actuator 222 may be connected to the control rod 224 directly, in which case the actuator 222 is also manipulated by pushing and pulling. The control rod 224 may be straight or curved or a combination of these shapes. The control rod 224 may be stiff, bendable, or partially stiff and partially bendable. In a preferred embodiment, the actuator 222 is manipulated by rotation, through a threaded surface that rotatably interfaces with a threaded surface on the control rod 224. A rotational coupling between the actuator 222 and the control rod 224 may provide increased mechanical advantage to the lumen-forming member 206 for piercing through bone. In still other embodiments, a power source may be provided for hydraulic, pneumatic or other power-assisted manipulation of the lumen-forming member 206.

As mentioned previously, the plate 214 can be fixed, or movable with respect to the frame 218. Various attachment means include, but are not limited to, welding, brazing, gluing, cementing, pin, hinge, and ball and socket. In one embodiment, the punch arm is curved. Different curved shapes of the punch arm are possible. In one embodiment the punch arm 210 is straight. In another embodiment the punch arm 210 has at least one straight segment and at least one curved segment. The segments may lie within the movement plane of the punch arm 210, or alternatively, one or more segments may lie outside the movement plane. Likewise, the movement of both lumen-forming tips 212 typically occurs in the same plane, but in other embodiments, the movement of each tip 212 may occur in different planes that intersect at the intermediate position. In other embodiments of the lumen-forming tool 200, only one arm moves or the two arms may move asymmetrically. In another embodiment of the lumen-forming tool, the lumen-forming arms move sequentially or in an alternating manner.

In one embodiment, the punch arm 210 is sized to be able to pass through the articular processes of the spine and the resulting hole is sized for a prosthesis retainer to be inserted. The size is appropriate for the retainer to slide or not slide in the hole, depending on the retainer design selected.

Referring to FIGS. 57A to 57E, the tool 200 may be used by positioning the lumen-forming tip 212 against one articular process 22 and positioning the plate 214 against the corresponding articular process 20. When the tool 200 is actuated, the tip 212 is forced through both articular processes 20, 22 while supported by the plate 214 support member 208.

Figure 57A:
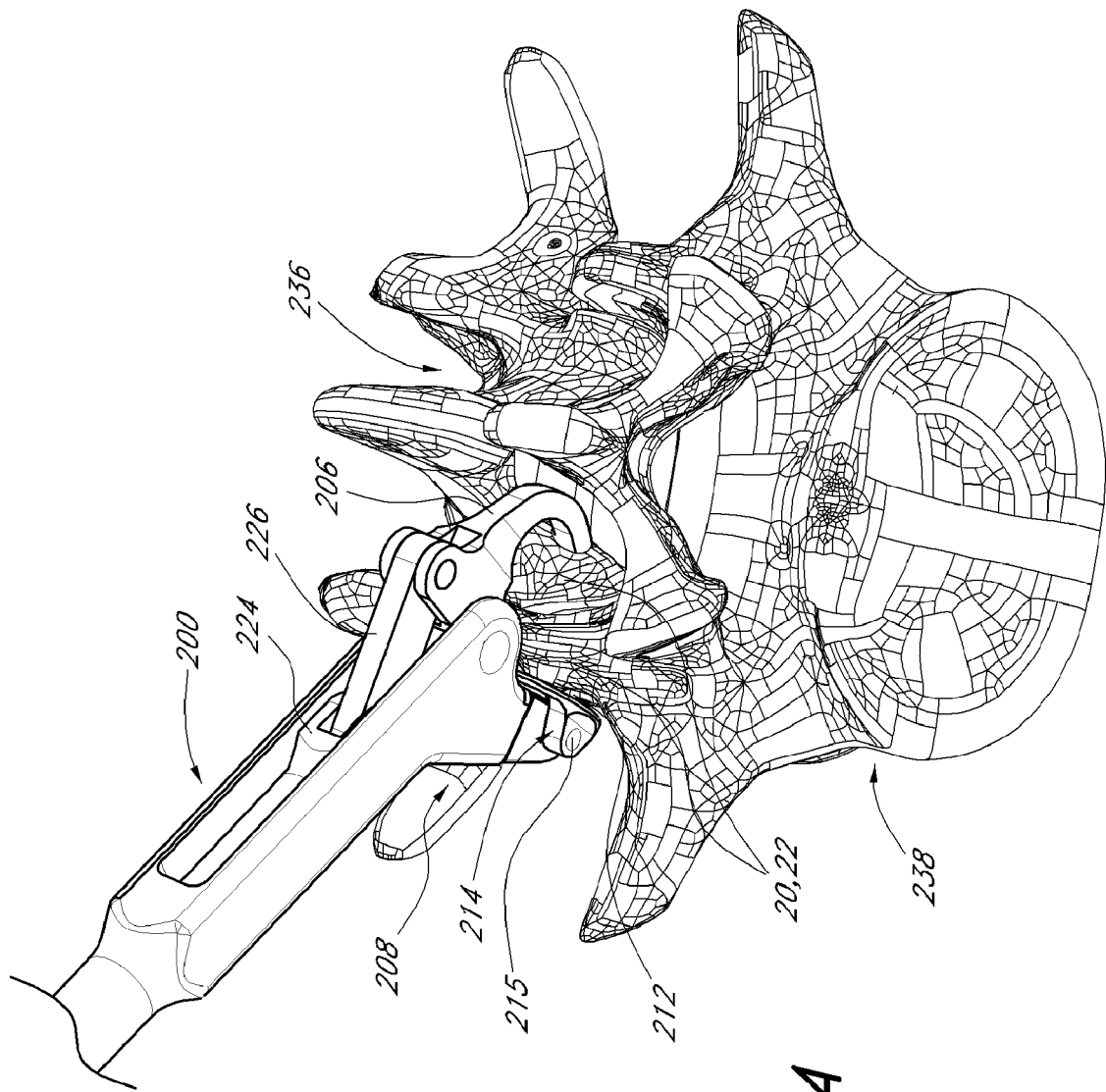
Figure 57B:
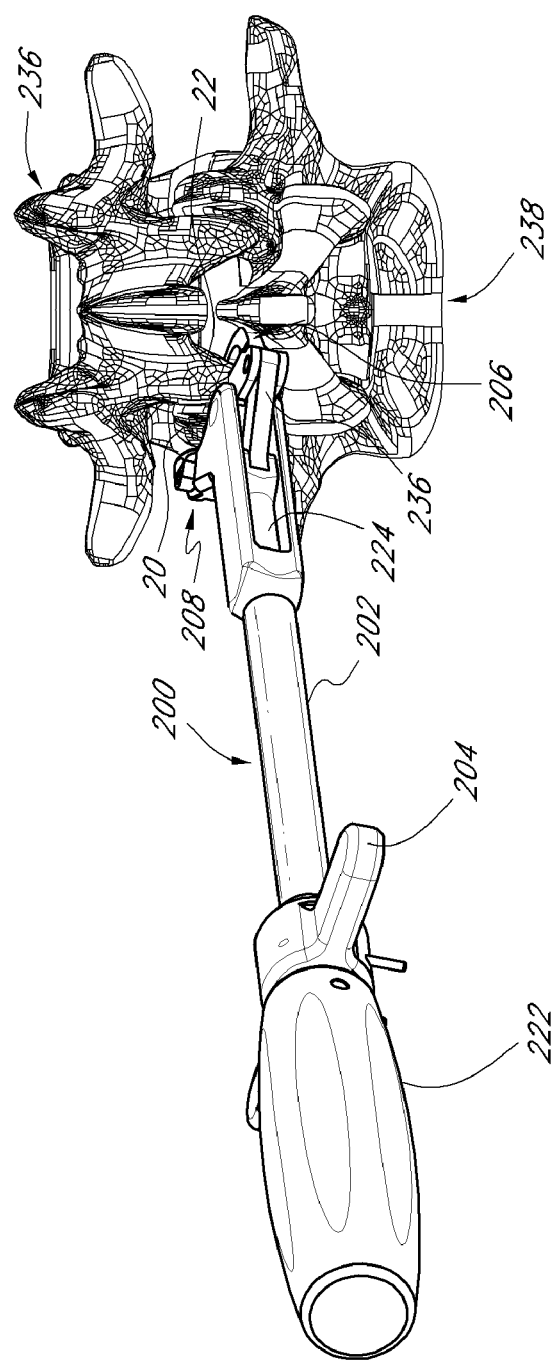
Figure 57D:
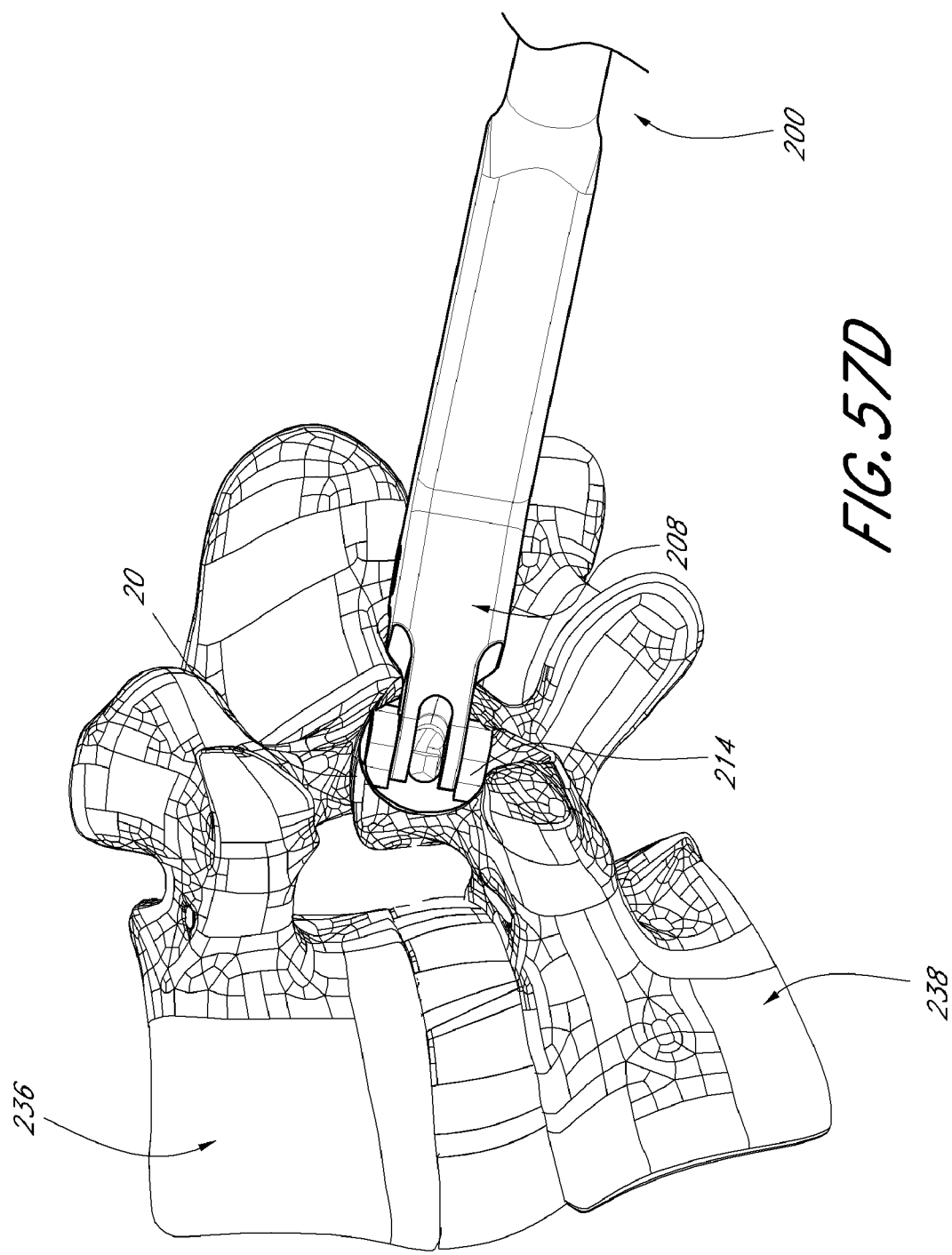
Figure 57E:
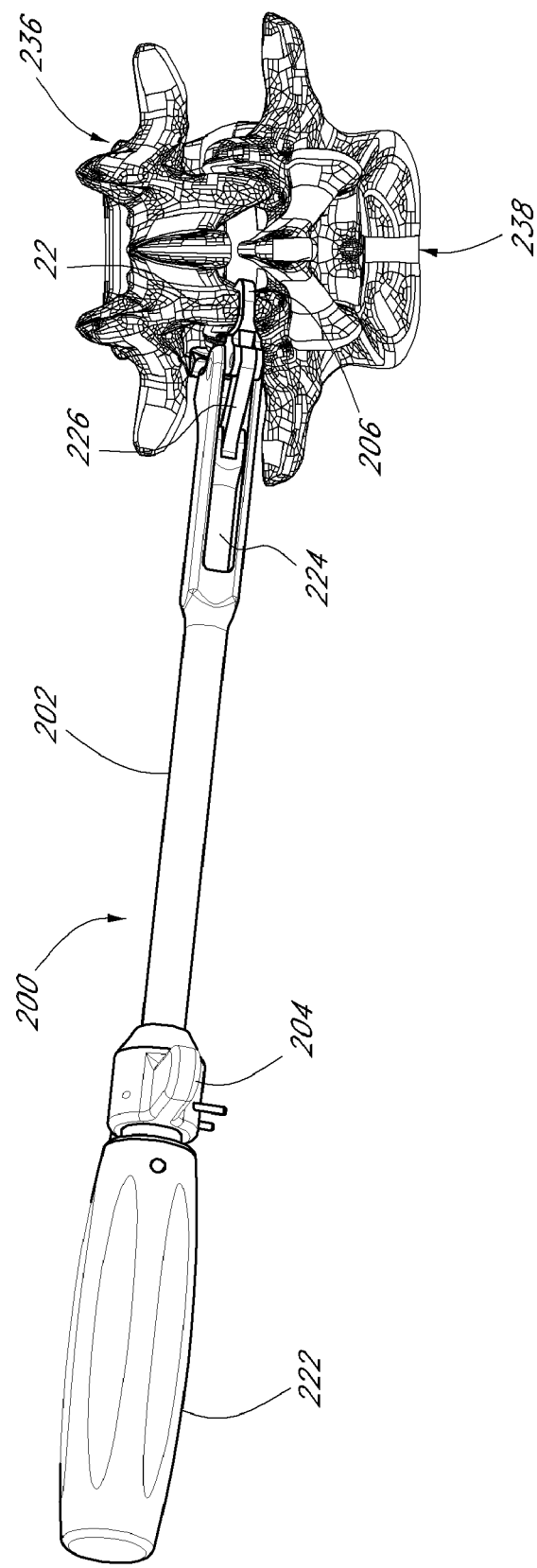

FIG. 57B depicts one approach to the articular processes 20, 22 that may be used with the tool 200. In this particular embodiment, the support member 208 is applied to the articular process 20 of the inferior vertebra 238, but in other embodiments, the support member 208 may be applied to the articular process 22 of the superior vertebra.

Figure 53B:
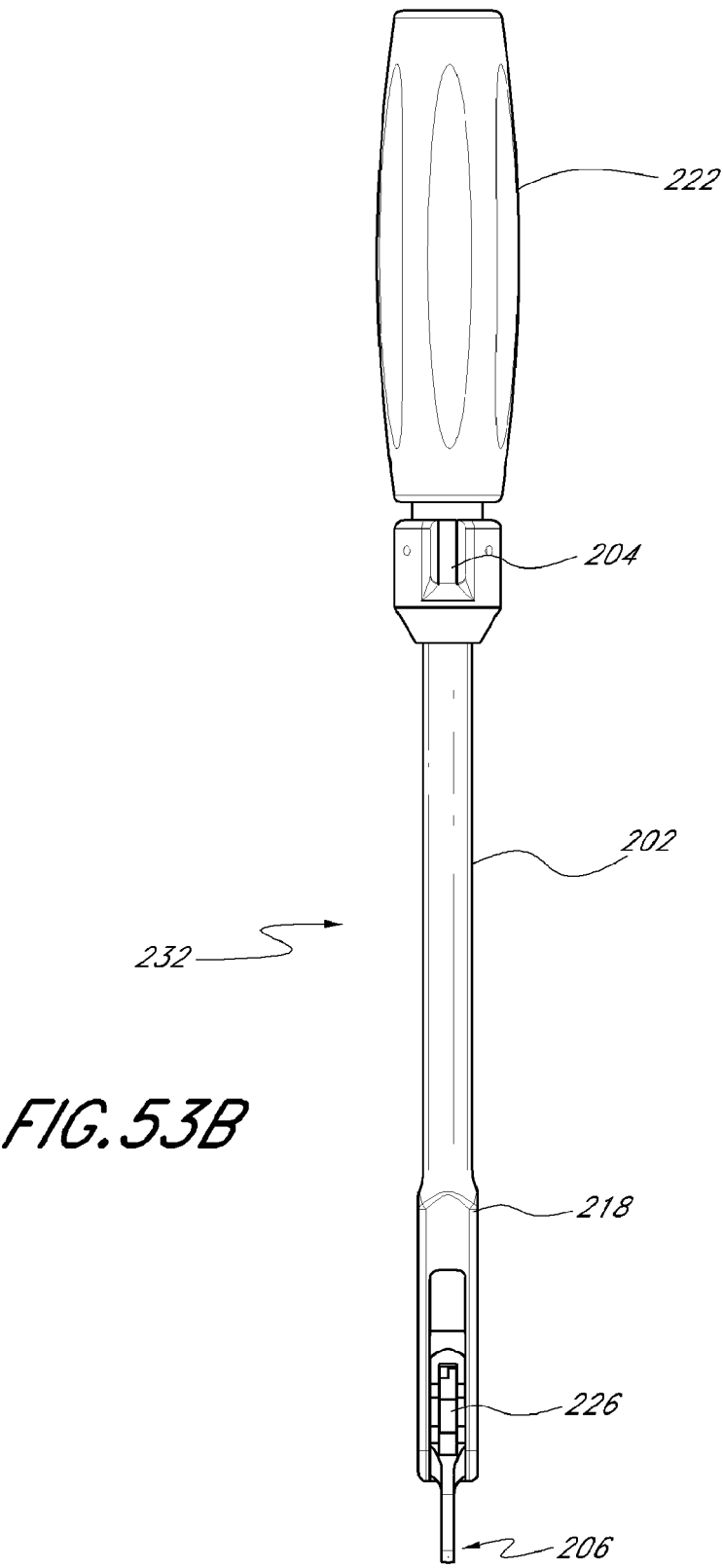
Figure 53C:
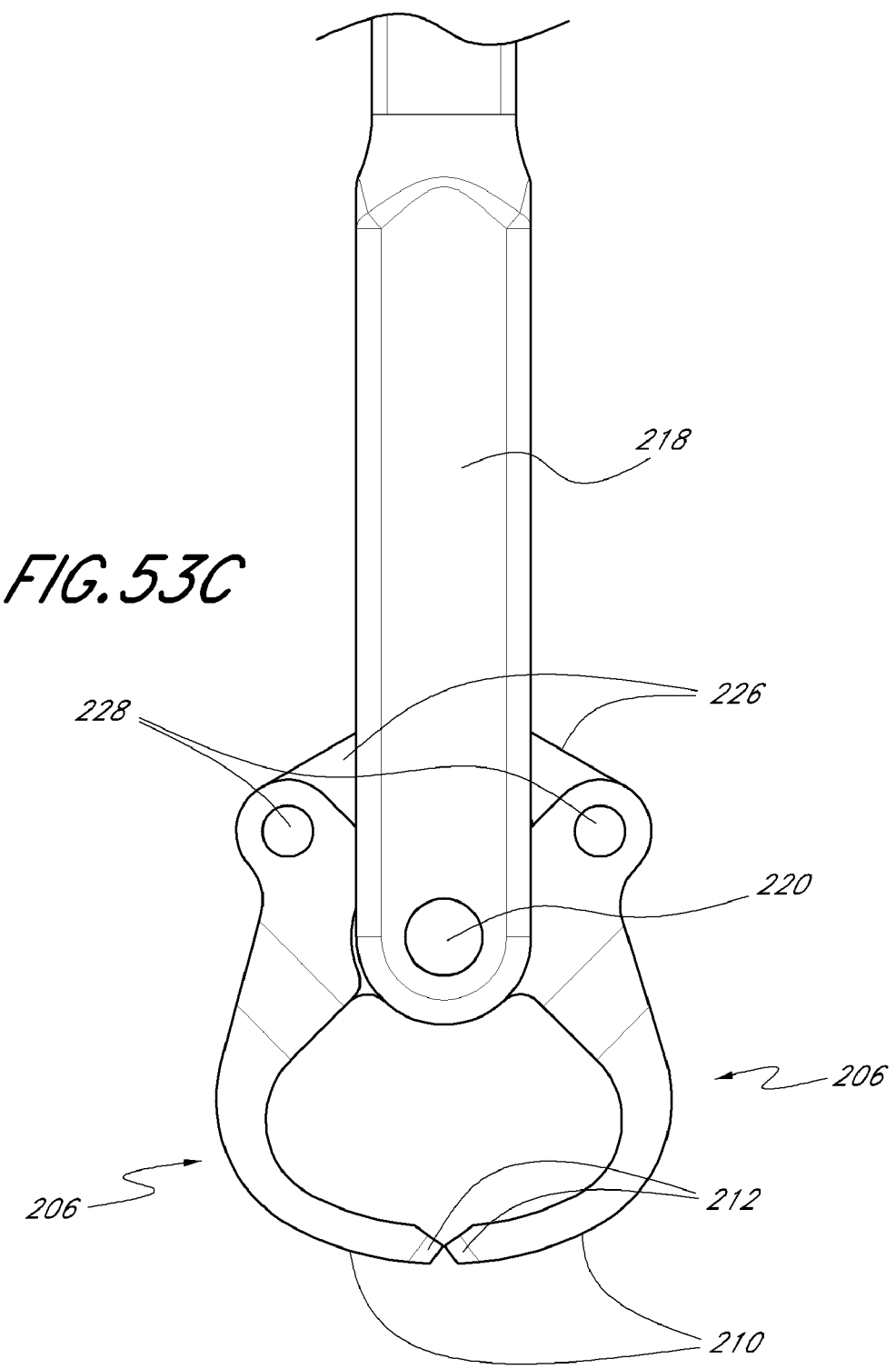
Figure 53D:
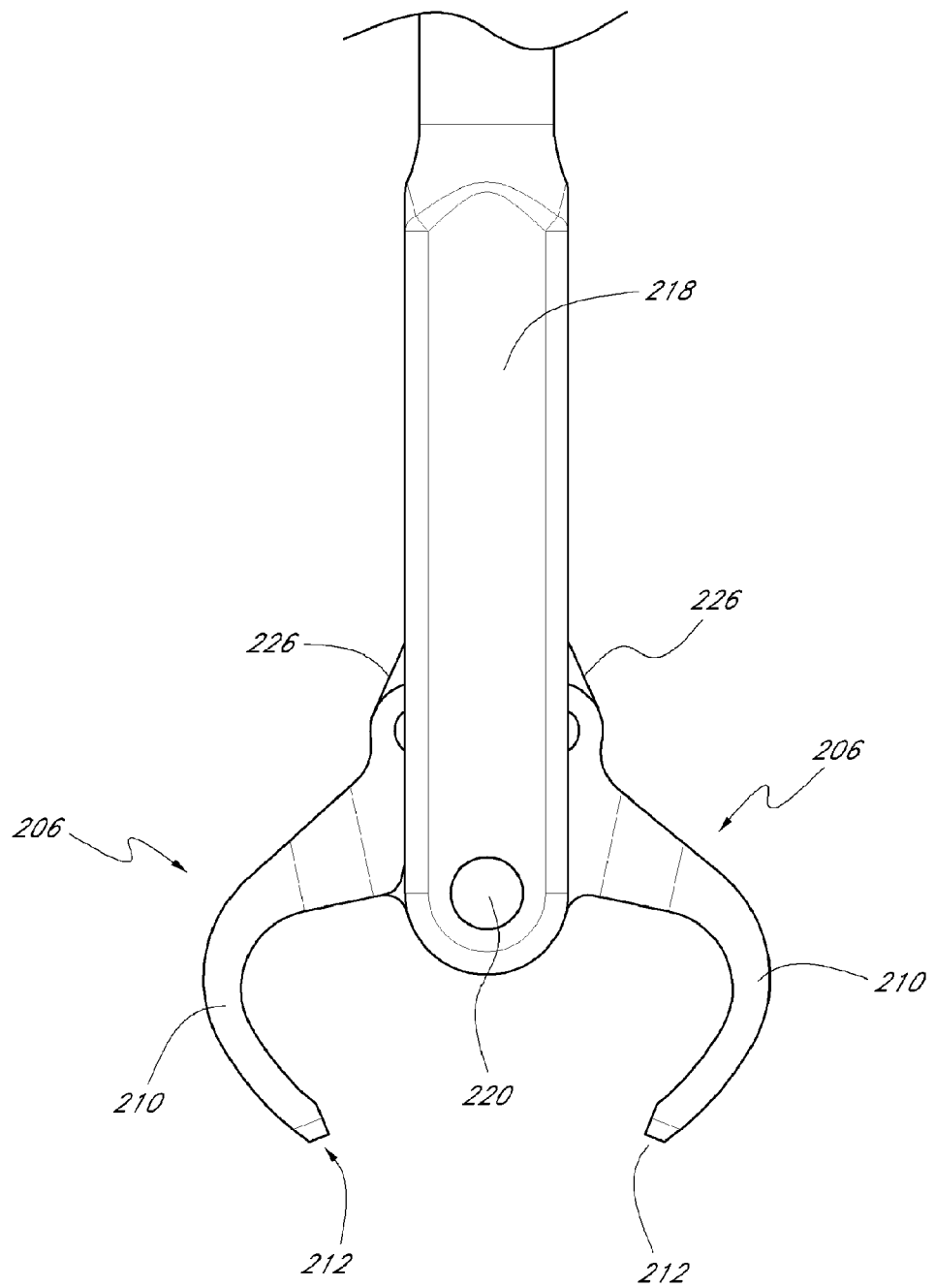
Figure 53E:
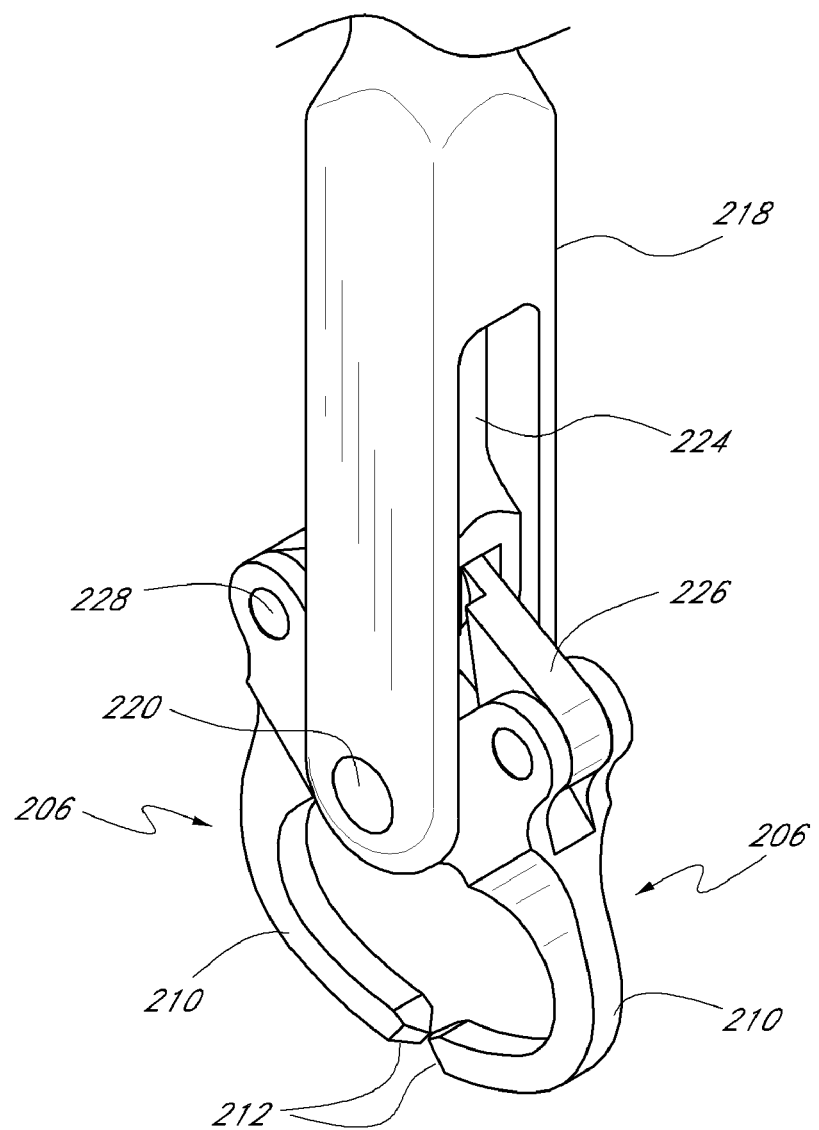
Figure 53F:
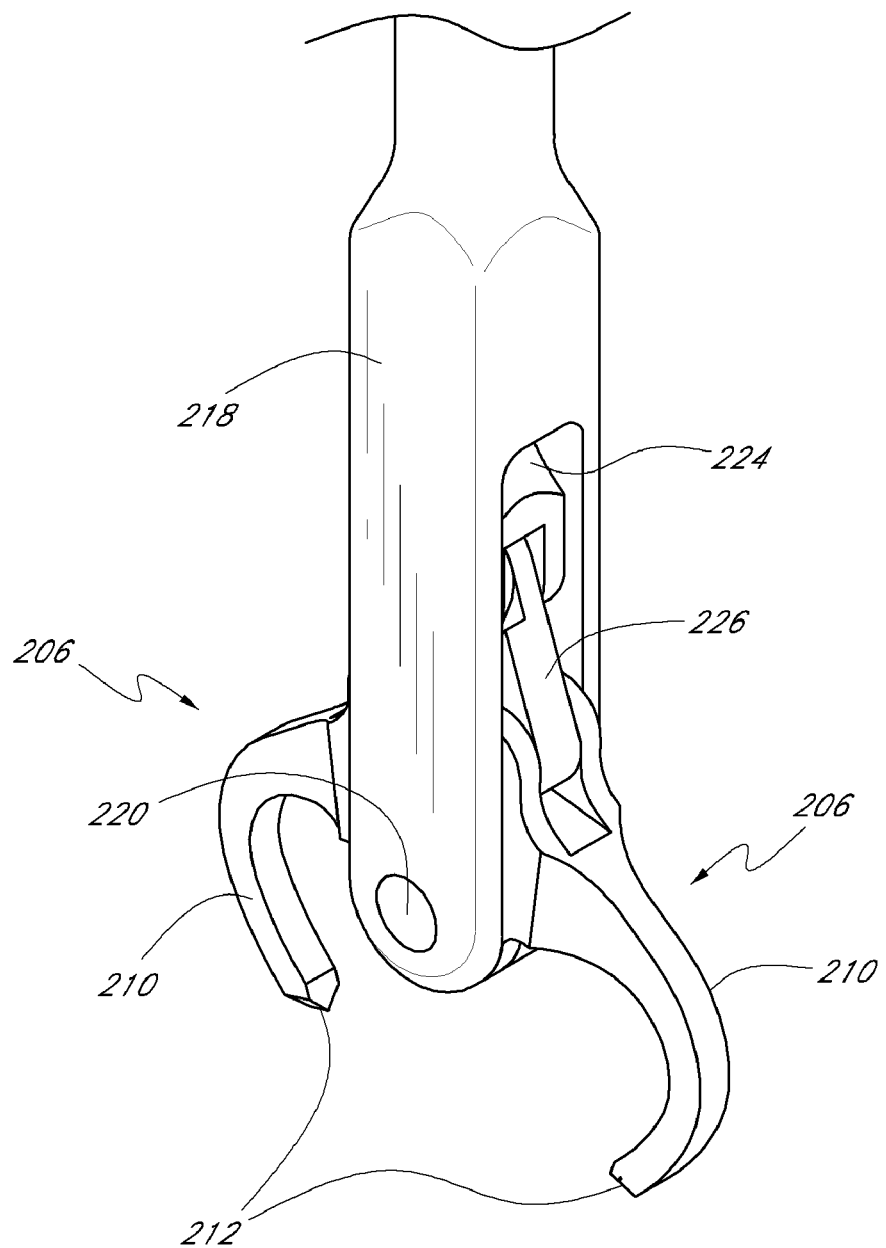
Figure 54:
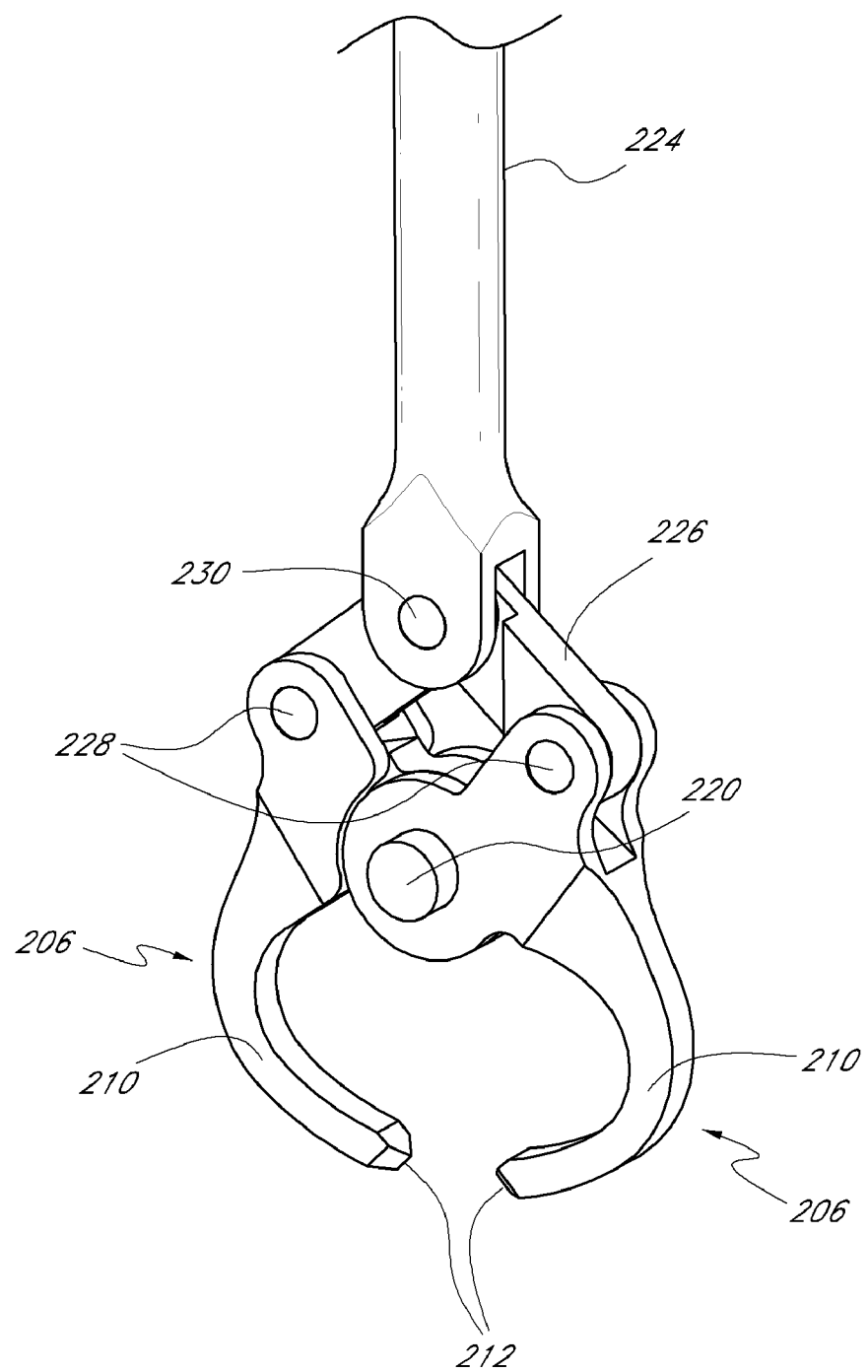
FIG. 54 depicts the distal end of the tool of FIGS. 53A to 53F without a frame member.
Figure 55:
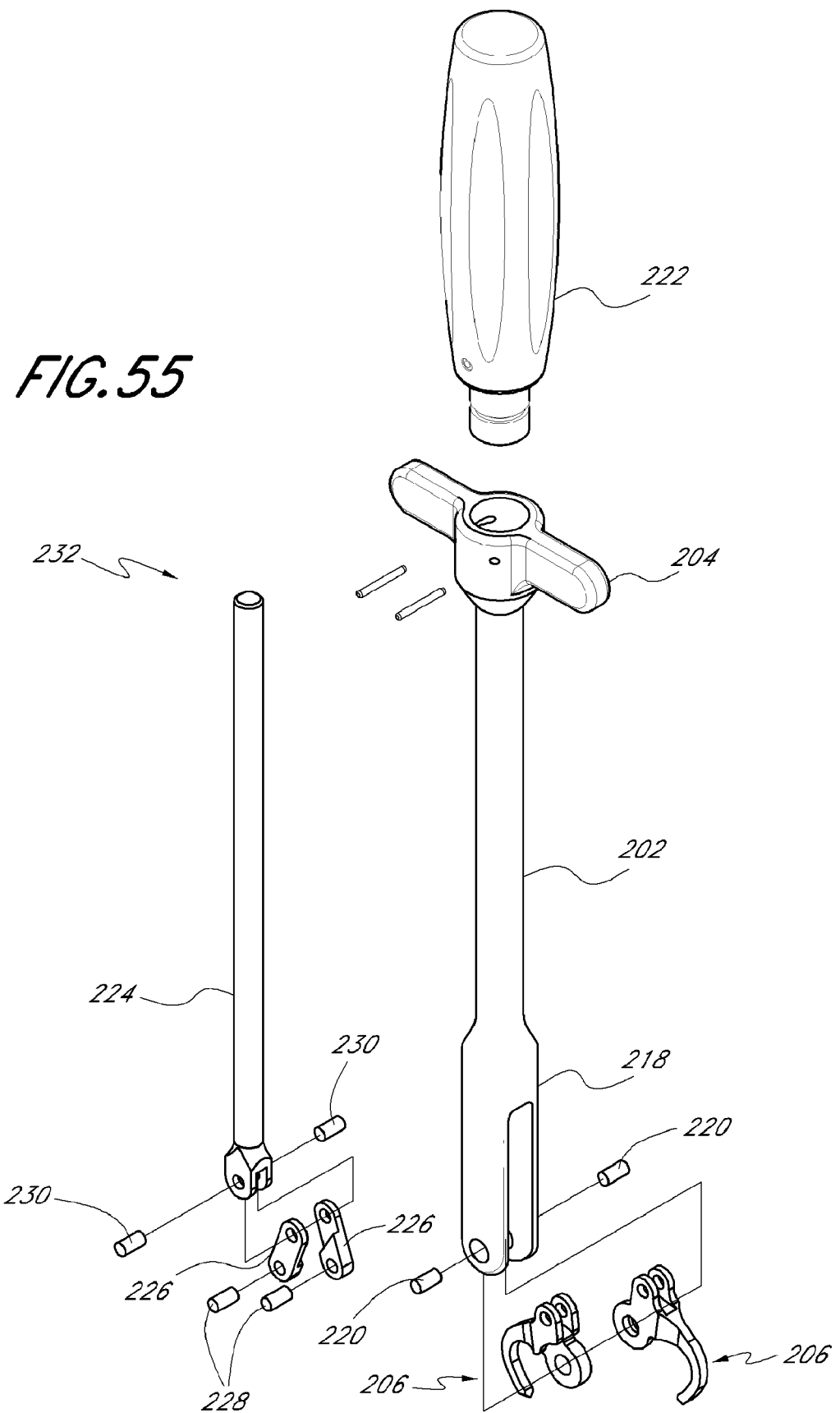
FIG. 55 is a component view of the tool shown in FIGS. 53A to 53F.

In another embodiment, illustrated in FIGS. 53A to 53F, the tool 232 comprises dual lumen-forming members 206 that are movable in a pincher-like fashion. The tool 232 comprises an shaft 202 with a proximal handle 204 and a distal frame member 218 with two lumen-forming members 206 connected to a frame 218. Each lumen-forming member 206 comprises an arm 210 with a piercing tip 212 at one end and is rotatably connected to the frame 218 by a pivot pin 220. Each lumen-forming member 206 is also joined to the control rod 224 by a link member 226 with pivot pins 228, 230, as depicted in FIGS. 54 and 55. The control rod 224 runs through the outer shaft 202 and connects to the actuator 222 preferably with threads. The outer shaft 202 is connected at one end to the handle 204. Although the embodiment depicted in FIGS. 53A to 55 have lumen-forming members that pivot in equal amounts, one of skill in the art will understand that the configuration may be modified to move differently. In one specific embodiment, only one lumen-forming member moves while the other member is fixed in position. One of skill in the art will also recognize that other movements of the control rod, link members and lumen-forming members are not limited to pivoting or angular movements. Alternate embodiments of the dual-arm tool 232 may include similar alternate structures as described for tool 200 above.

Figure 56A:
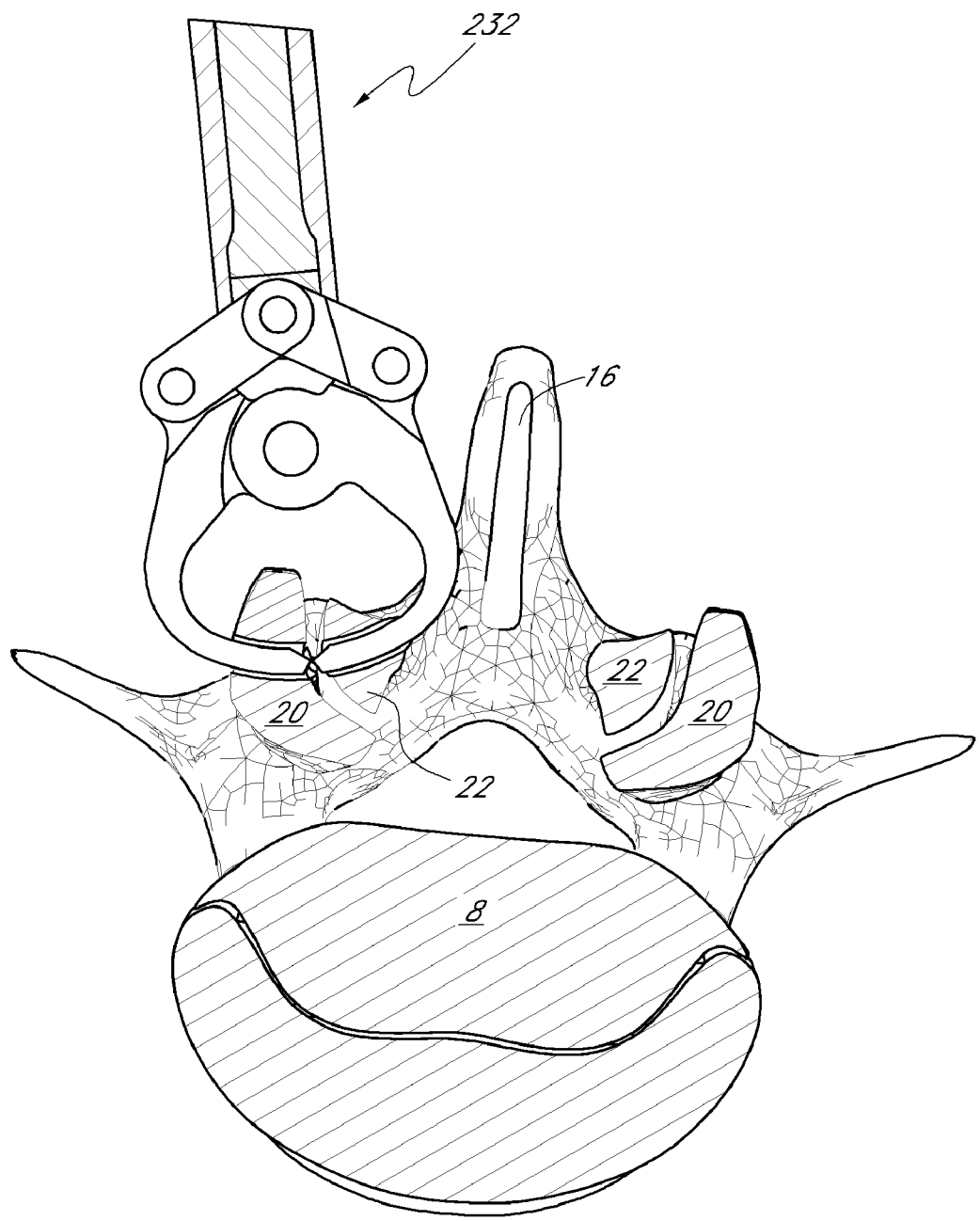
FIGS. 56A to 56C are sequential schematic representations of the use of the tool shown in FIGS. 53A to 53F.
Figure 56B:
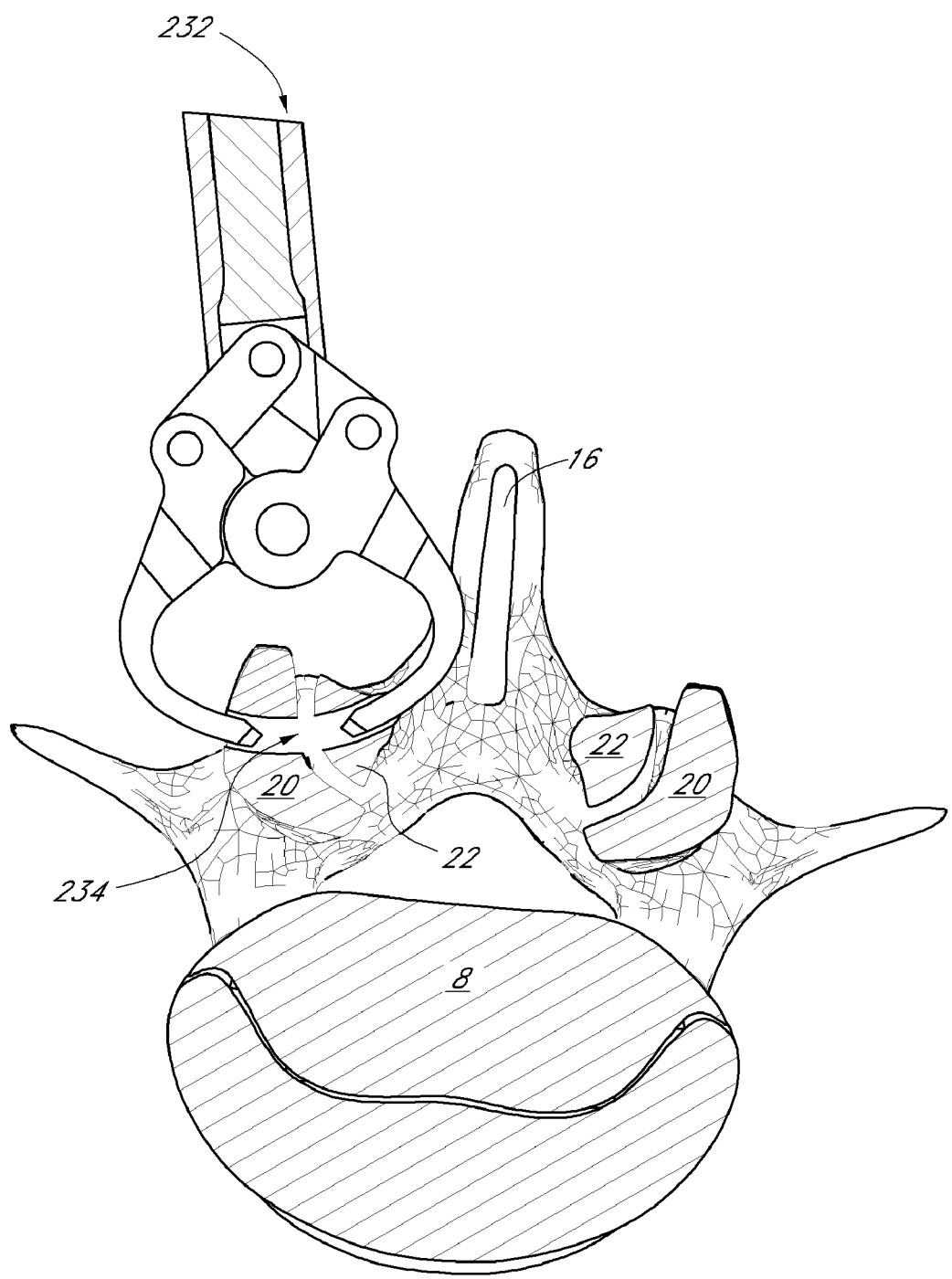
Figure 56C:
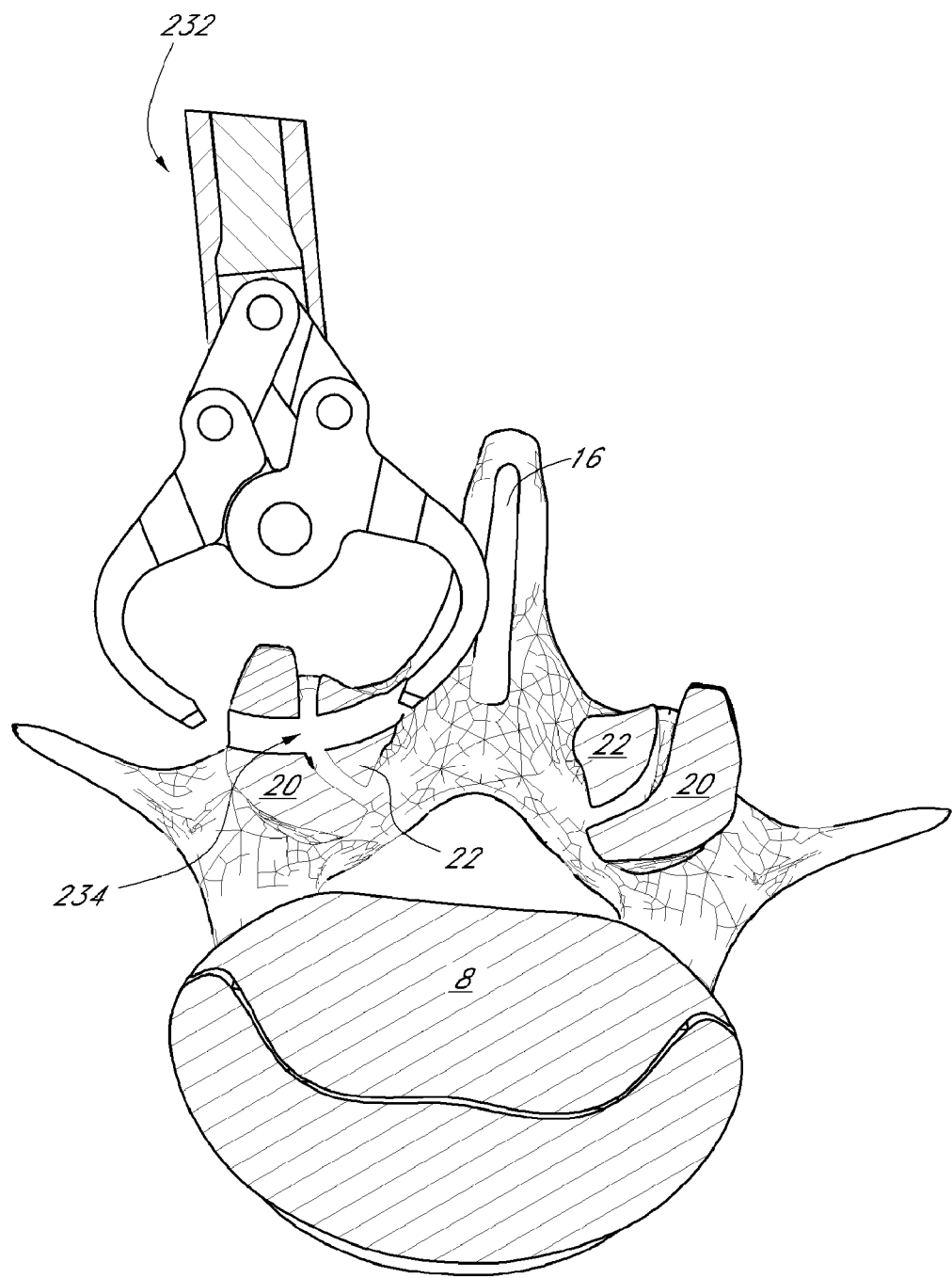
Figure 58B:
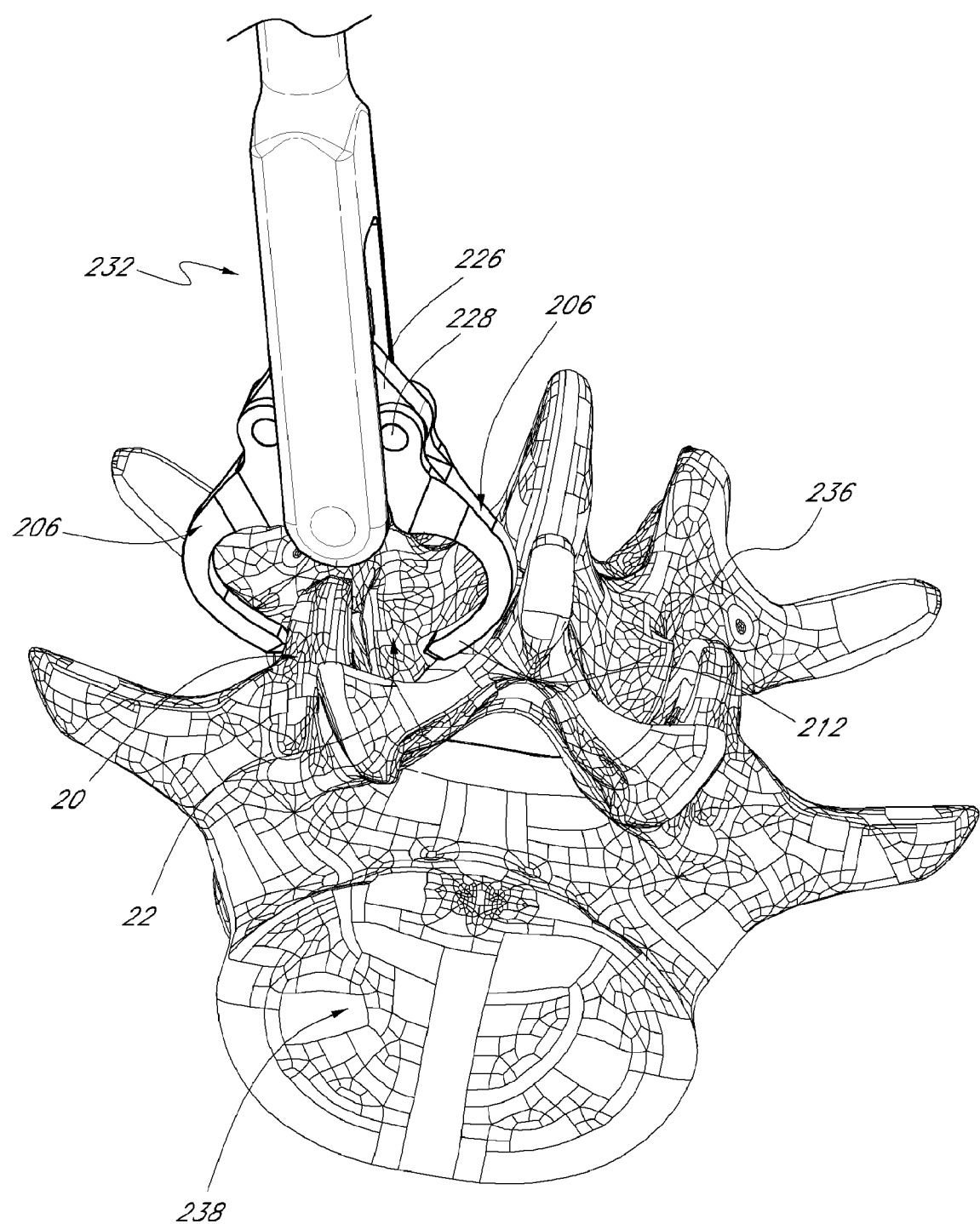
Figure 58C:
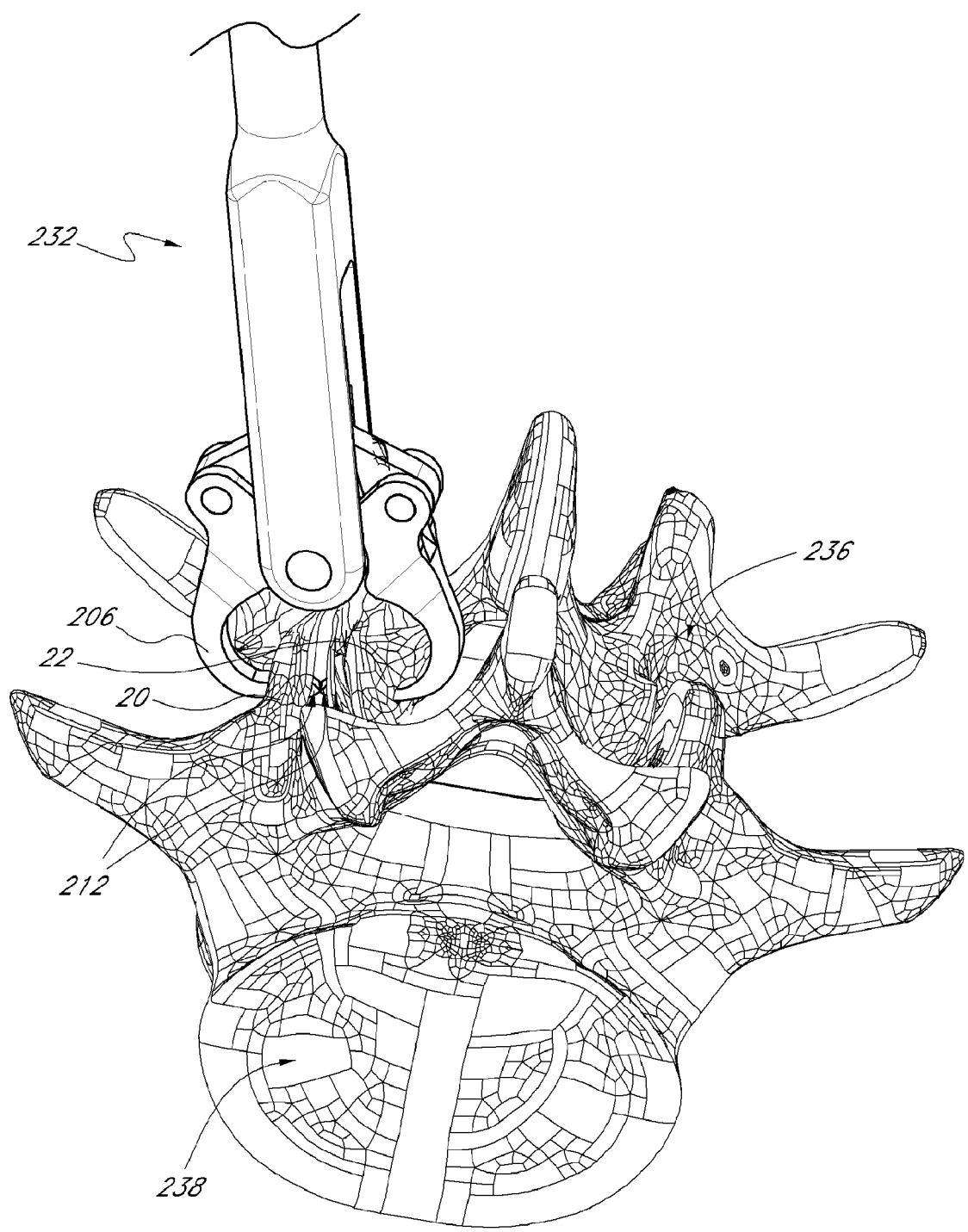
Figure 58D:
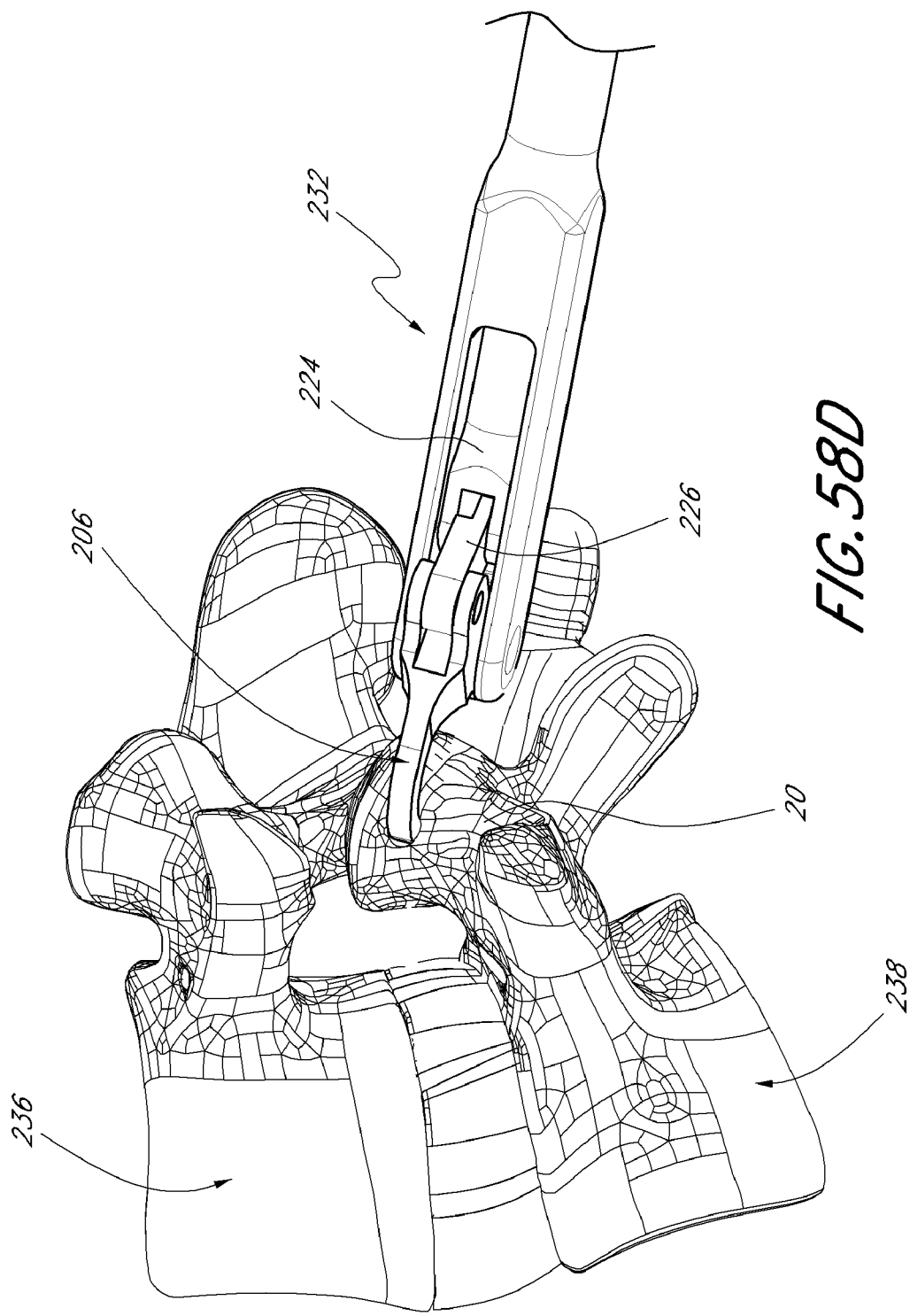
Figure 58E:
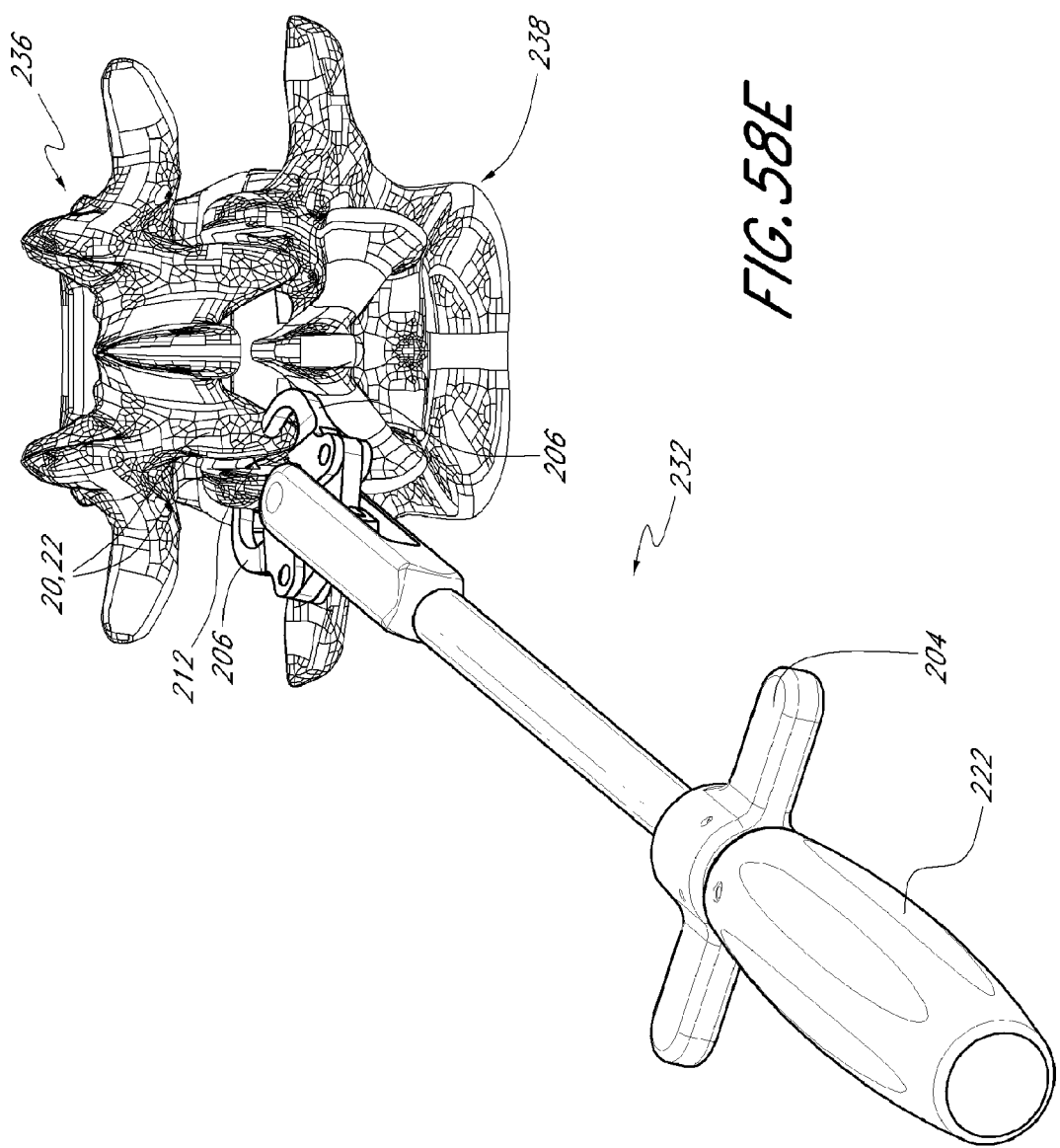
Figure 58G:
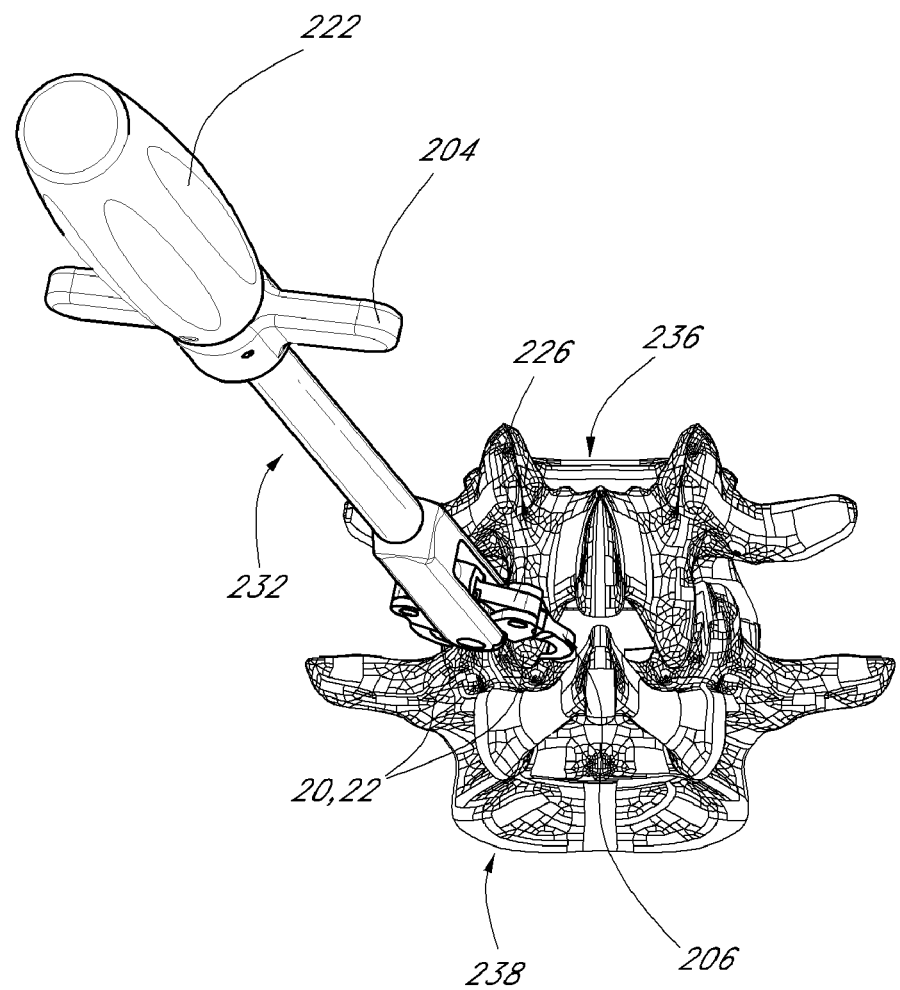

Referring to FIGS. 58A to 58C, one method of use for the tool 232 comprises placing one lumen-forming tip 212 against an exposed articular process 22 of a superior vertebra 236 and placing the other lumen-forming tip 212 against the corresponding articular process 20 of the inferior vertebra 238. The handle 204 of the tool 232 is held while the actuator 222 is rotated. Rotation motion of the actuator 222 is transferred to the control rod 224 as a linear motion away from the actuator 222 via the threaded connection. This movement of the control rod 234 is transferred to the lumen-forming members 206 via the link members 226 and pivot pins 228, 230 as a pinching motion where the piercing tips 212 approach each other through the bone of the articular processes 20, 22. Movement of the lumen-forming tips 212 continues until they meet at an intermediate position to form a curved or non-linear passageway 234 through the articular processes 20, 22. FIGS. 56A to 56C depict the tool 232 after the formation of the passageway 234, as the tool 232 is moved from a closed configuration, as shown in FIG. 56A, to an open configuration, as shown in FIG. 56C. The resulting passageway 234 through the articular processes 20, 22 may be straight or preferably curved, depending on the design of the lumen-forming member 206 and particularly the configuration of the lumen-forming arms 210. For example, the lumen-forming arm 210 can be straight or preferably curved or non-linear. When two lumen-forming arms 210 are present, the two arms 210 need not have the same configuration. They can be of any appropriate cross-section area or shape, including but not limited to triangular, square, rectangular, hexagonal, pentagonal, octagonal, heptagonal, round, elliptical, or any combination of shapes. These shapes are applicable to single-arm and two-arm tools 200, 232. In embodiments of the tool 232 with two arms 210, the arms 210 can have a similar configuration or different configurations. With two movable arms 210, the two arms preferably move in the same movement plane and preferably move by rotating around rotational axes that are generally perpendicular to the movement plane. In other embodiments, the arms may have cutting edges along its length and exhibit some rotation along its longitudinal axis, similar to a drill.

FIGS. 58D to 58G illustrate various approaches and relative orientations that may be taken with the tool 232 with respect to the articular processes 20, 22 and vertebrae 236, 238. The surgeon may select a particular rotational and/or angular approach to the surgical site, depending upon the particular vertebral morphology of the patient, the extent and location of damage or injury, prior surgery, and other factors known in the art.

In another embodiment, illustrated in FIGS. 59A to 59D, the tool 300 comprises dual lumen-forming members 206 that are movable in a pincher-like fashion in a manner similar to the tool 232 of FIGS. 53A to 53F described above. In this illustrated embodiment, the tool 300 comprises a shaft 202 with a proximal handle 204 and a distal frame member 218 with two lumen-forming members 206 connected to a frame 218. Each lumen-forming member 206 comprises an arm 210 with a piercing tip 212 at one end and is rotatably connected to the frame 218 by a pivot pin 220. Each lumen-forming member 206 is also joined to the control rod 224 by a link member 226 with pivot pins 228, 230. The control rod 224 runs through the outer shaft 202 and connects to the actuator 222 preferably with threads. The outer shaft 202 is connected at one end to the handle 204. In this illustrated embodiment, each lumen-forming member 206 comprises a bend that puts the lumen-forming arm 210 and the lumen-forming tip (i.e., piercing tip) 212 in the same plane as the longitudinal axis of a spacing member 310, to be described below. In this illustrated embodiment, the lumen-forming tip is out of the plane as the shaft 202.

The tool 300 further comprises a spacing member 310 that can be coupled to the shaft 202 through a detachable clipping member 306. In the illustrated arrangement, the spacing member 310 comprises a spacing member shaft 304 that is connected to the clipping member 306 at the proximal end and a spacer 302 at the distal end. The spacer 302, in turn, may comprise a disk-like member and two indentations 308 on each side of the disk-like member, and the indentations 308 are lined up or aligned with the lumen-forming member 206 to allow the lumen-forming tips 212 of the lumen-forming members 206 to penetrate through the bones and into the indentations 308. In some embodiments, the disk-like member of the spacer 302 may have an opening or a hole instead of the indentations 308, and the two lumen-forming tips 212 could make contact with each other through the opening or the hole after penetrating the bones. The spacer 302 may have a curved shape disk-like member to facilitate positioning between the articular processes 20 and 22. In some embodiments, the disk-like member of the spacer 302 may have different shape, size and thickness for used with different sized vertebra. The clipping member 306 allows the spacing member 310 to be detached from and attached to the facet drill tool with ease.

Although the tool 300 depicted in FIGS. 59A to 59D have a straight spacing member 310, a person skilled in the art would understand that the spacing member shaft 304 or the connection between the spacing member shaft 304 and the spacer 302 can be modified to have a bend, corner or curvature to position the spacer 302 for placing between the articular processes 20, 22 and for lining up with the lumen-forming members. For example, in an alternative embodiment, the spacing member 310 may be configured to have the spacer 302 bend toward the lumen-forming members 206, so the indentations 308 or the hole on the disk-like member of the spacer 302 are aligned with the lumen-forming tips. In some embodiments, the spacing member 310 may be used with either tool 200 or 232, wherein the lumen-forming member 206 is in the same plane as the shaft 202, as shown in FIGS. 52B and 53B. The spacing member 310 may have a bend near the distal end of the spacer member spacing member shaft 304 that allows the spacer 302 to bend into the plane of the longitudinal axis of the shaft 202, and the indentations 308 of the spacer 302 would be aligned with the lumen-forming tip 212.

In another alternative embodiment, the spacing member 310 may be used with tool 200. The spacing member 310 may be configured to have a bend to allow the spacer 302 to bend into the plane of the lumen-forming arm 210 and the piercing tip 212. In addition, the spacer 302 may also be movably connected to the spacing member shaft 304 through a pivot joint, wherein the disk-like member of the spacer 302 may be tilted out of the plane of the spacing member shaft 304 to allow for adjusting the distance between the plate 214 and the spacer 302 when positioning the tool 200 onto the articular processes 20, 22.

Figure 60:
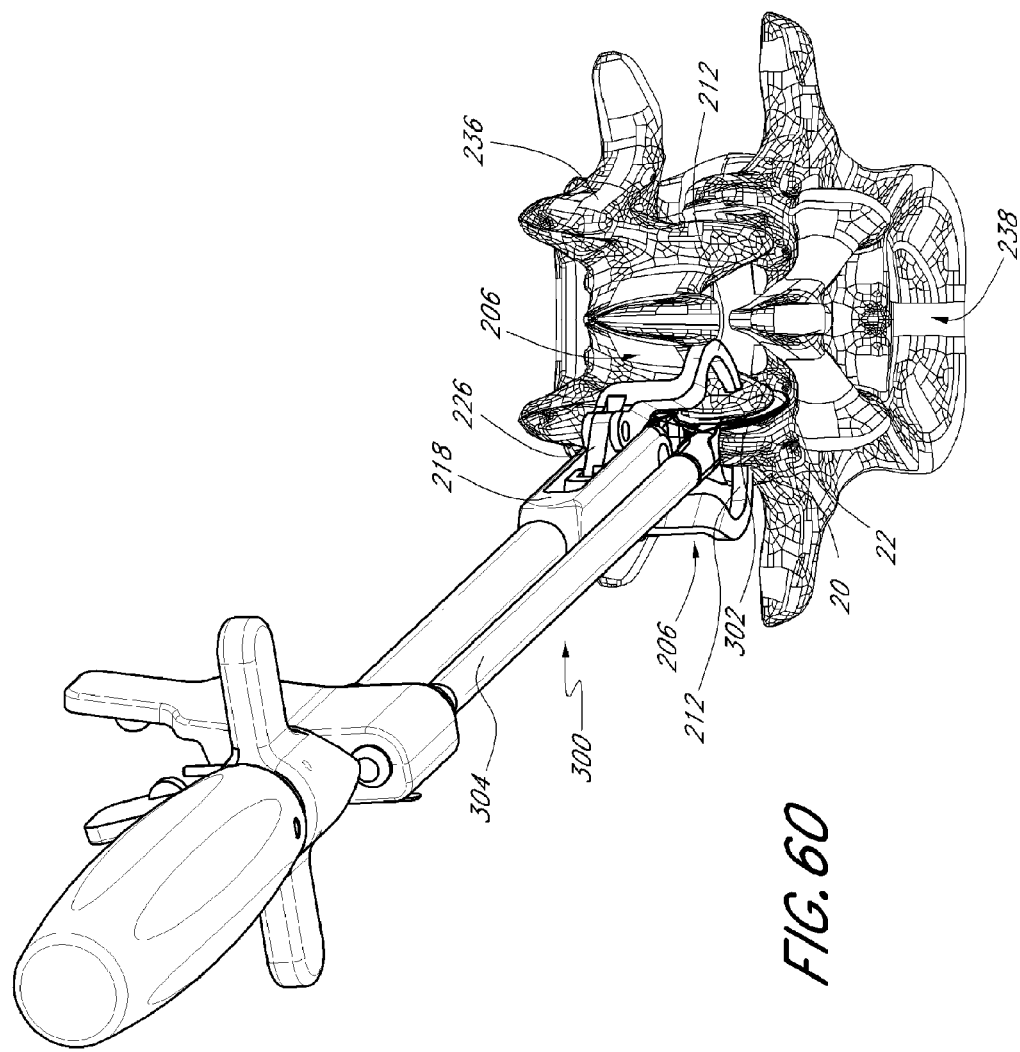
FIG. 60 shows an embodiment of the method of use of the tool in FIGS. 59A to 59D 53E wherein it is used to create a hole in the articular process of the vertebra.

Referring to FIG. 60, one method of use for the tool 300 comprises placing one lumen-forming tip 212 against an exposed articular process 22 of a superior vertebra 236, placing the other lumen-forming tip 212 against the corresponding articular process 20 of the inferior vertebra 238, and positioning the spacer 302 between the articular processes 20 and 22. The handle 204 of the tool 232 is held while the actuator 222 is rotated. Rotation motion of the actuator 222 is transferred to the control rod 224 as a linear motion away from the actuator 222 via the threaded connection. This movement of the control rod 234 is transferred to the lumen-forming members 206 via the link members 226 and pivot pins 228, 230 as a pinching motion where the piercing tips 212 approach each other through the bone of the articular processes 20, 22. Movement of the lumen-forming tips 212 continues until they pierce through the articular processes 20 and 22 and make contact with the indentations 308 to form a curved or non-linear passageway 234. In embodiments where the spacer has a hole instead of indentations, the lumen-forming tips 212 moves until they meet at an intermediate position to form a curved or non-linear passageway 234 through the articular processes 20, 22.

Figure 59A:
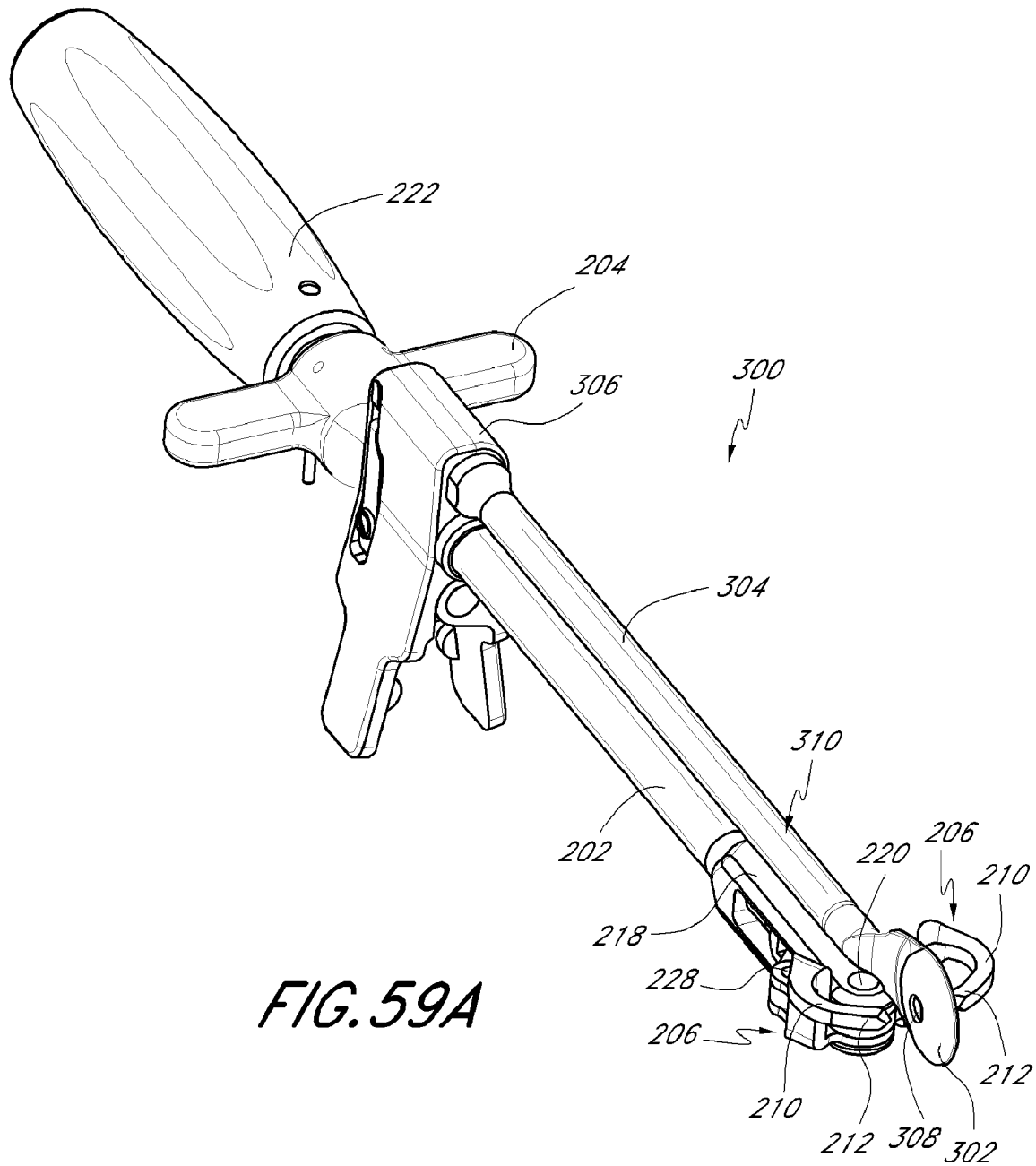
FIGS. 59A to 59D show one embodiment of the tool with dual punch arms and a spacer.
Figure 59B:
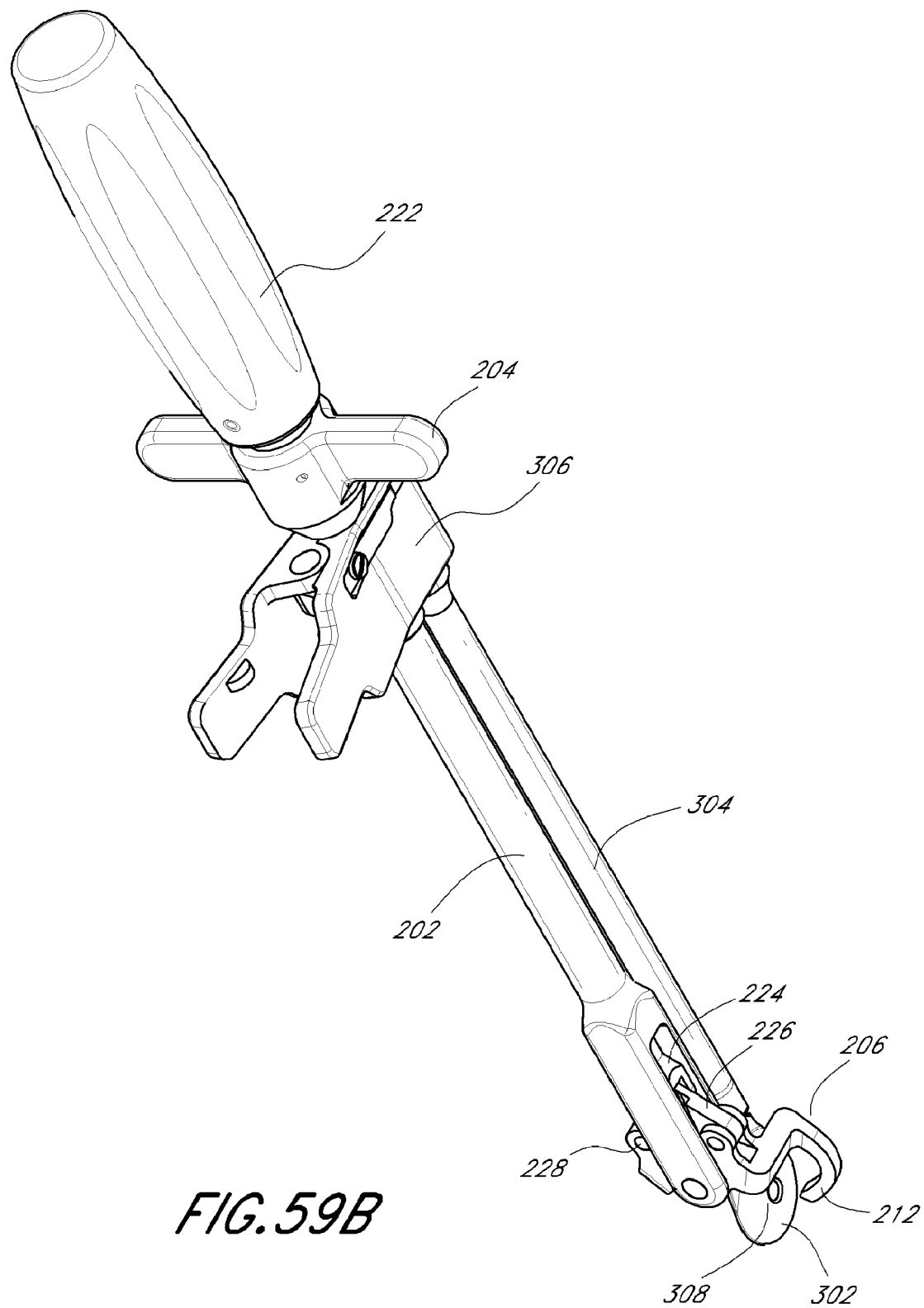
Figure 59C:
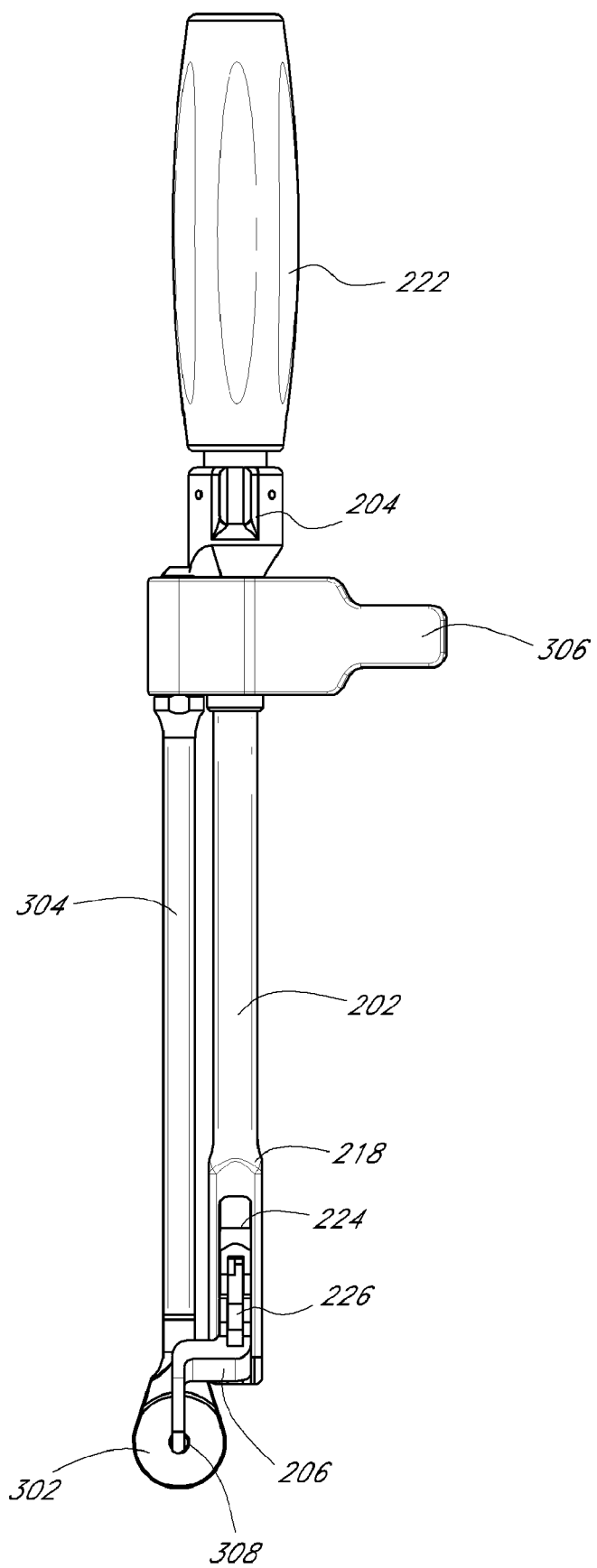
Figure 59D:
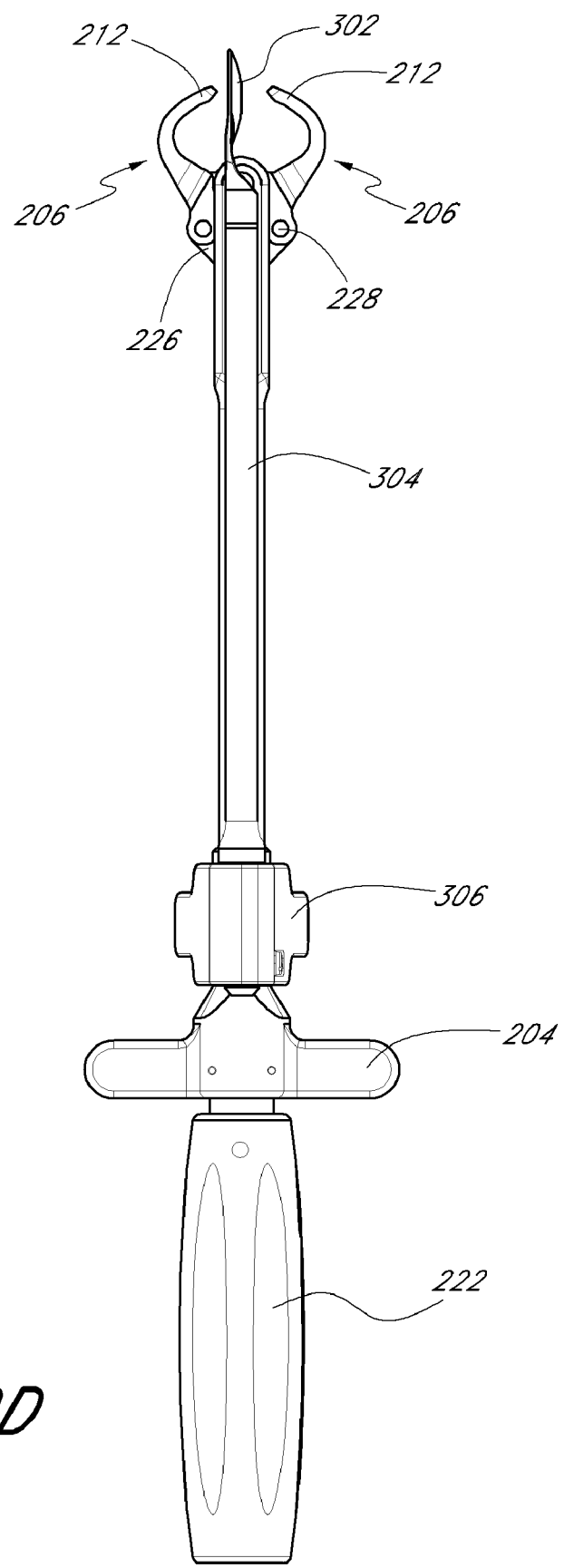

Although the embodiment depicted in FIGS. 59A to 60 have lumen-forming members that pivot in equal amounts, one of skill in the art will understand that the configuration may be modified to move in differently. In one specific embodiment, only one lumen-forming member moves while the other member is fixed in position. One of skill in the art will also recognize that other movements of the control rod, link members and lumen-forming members are not limited to pivoting or angular movements. Alternate embodiments of the tool 300 may include similar alternate structures as described for tool 200 above and with reference to FIGS. 52A-58G.

In some embodiments of the either tool 200, 232 or 300, the movement of the lumen-forming members 206 and/or plate 214 can be effected by manual force applied by a person, such as by his or her hands, or alternatively it can be supplied or supplemented with a motor, pneumatics, hydraulics, springs, and/or magnetics. A movable grip may be used to manipulate and actuate the lumen-forming members of the tool. The grip may be designed for rotational, pivoting linear relative movement, or combination thereof, depending on the mechanical advantage that may be needed to facilitate movement of the lumen-forming arm(s) and piercing through the articular processes. One embodiment of the tool may comprise a squeeze handle for actuating the tool. In other embodiments, the tool comprises an actuator with a switch or trip mechanism. Movement of the lumen-forming tips can be effected with coaxial shafts, non-coaxial shafts, wires, rods, springs, hydraulics, gas cylinder, piston, gears, motor, electrical signal, magnetics, or other suitable means for communicating a signal or transferring movement or providing the closing force. Other embodiments of the tool include closing mechanisms that include compound leverage, ratcheting, and/or multistep closing.

G. Powered Facet Drill

Another embodiment of the tool 400, shown in FIGS. 61A-62B, can comprise a shaft 402 with a proximal handle 404 and a distal arm guide 406. The arm guide 406 contains a lumen-forming arm 410 that can be moved in the proximal-distal direction by manipulation of a proximal actuator 422. The distal portion also comprises an opposing target member 408 having a target plate 414, as described in more detail below. The lumen-forming arm 410 comprises a rotating drill bit 412 that can be connected to a drill motor by a drill coupler 424 disposed toward the proximal end of the tool 400. A spacing member 500 with a spacer 502 at the distal end can be coupled to the tool 400. The spacing member 500 can be at least partially supported on the tool 400 by a frame 418 and the proximal handle 404. In some embodiments, the spacing member 500 can be secured to the tool 400 by a hook 510, which can be released by a release button 514, as discussed further below.

Figure 61B:
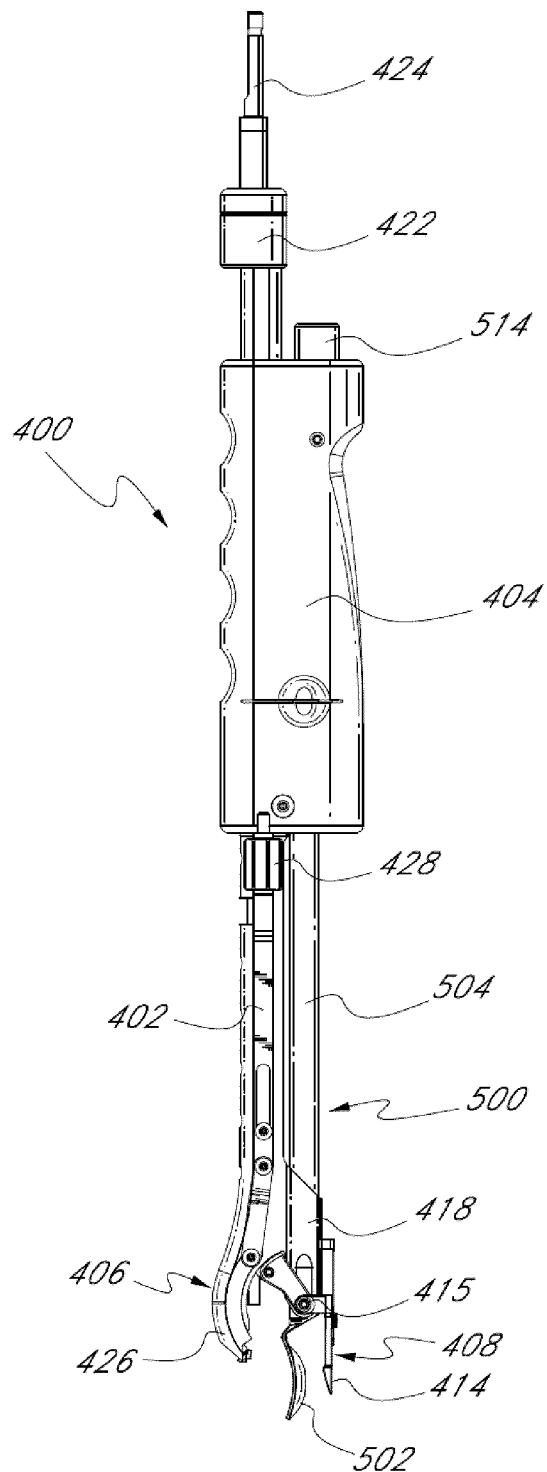
Figure 61C:
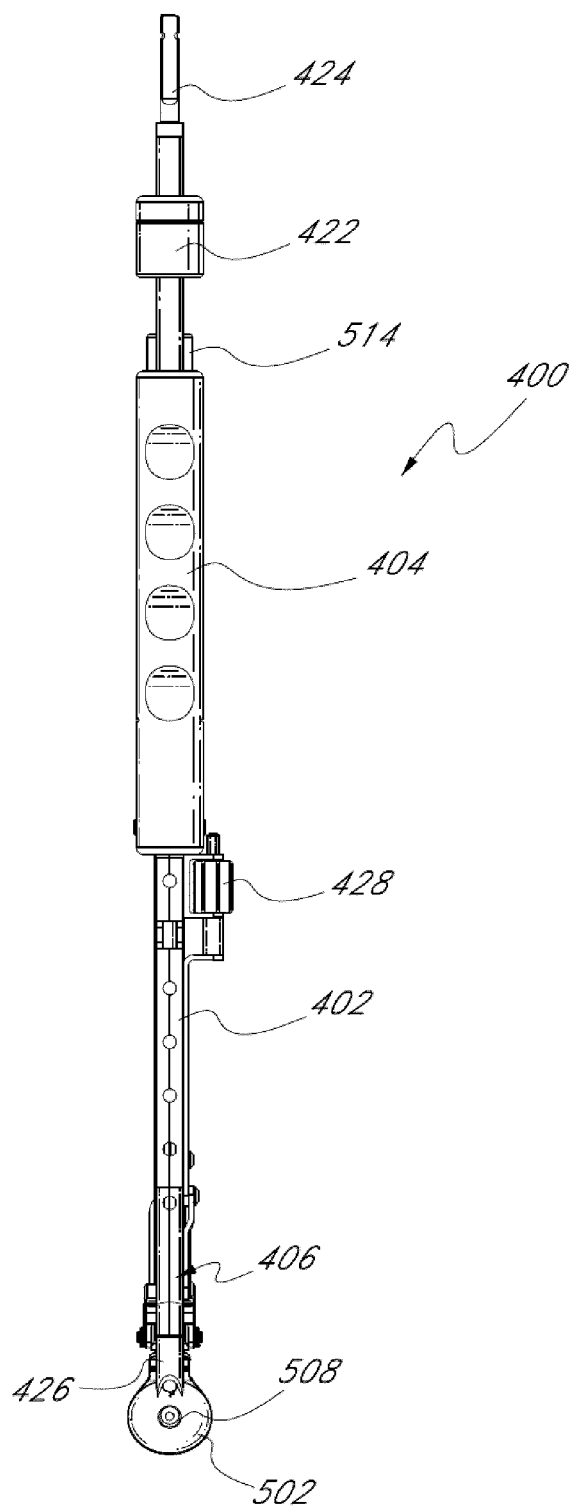
Figure 61D:
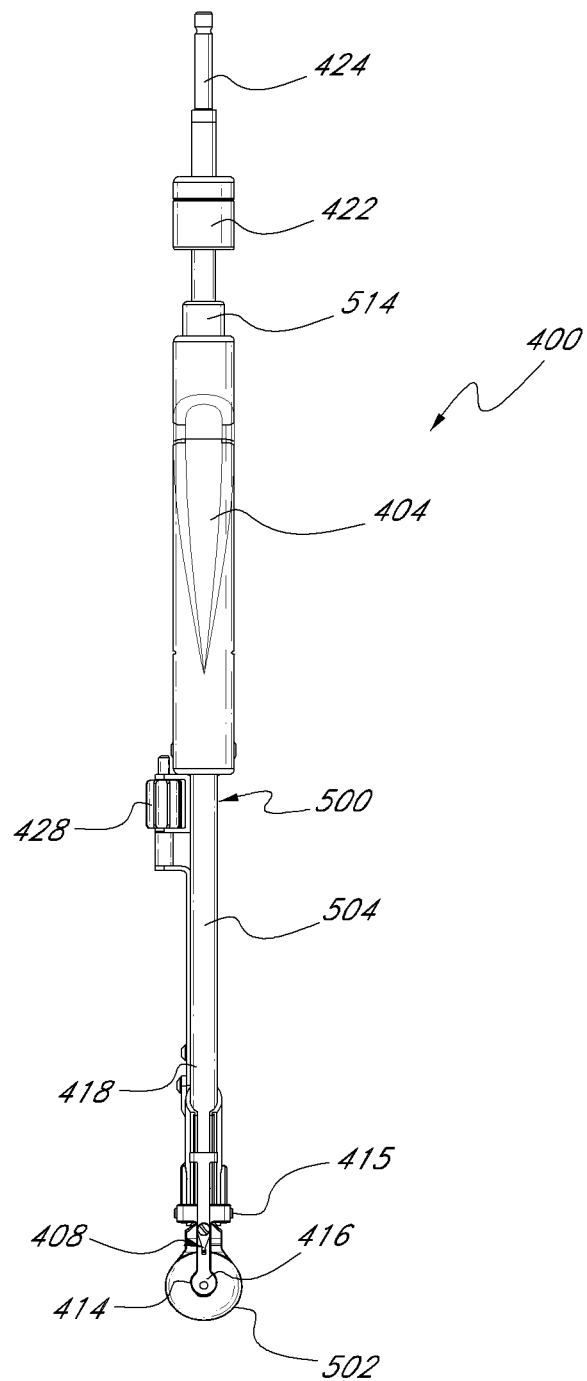
Figure 61E:
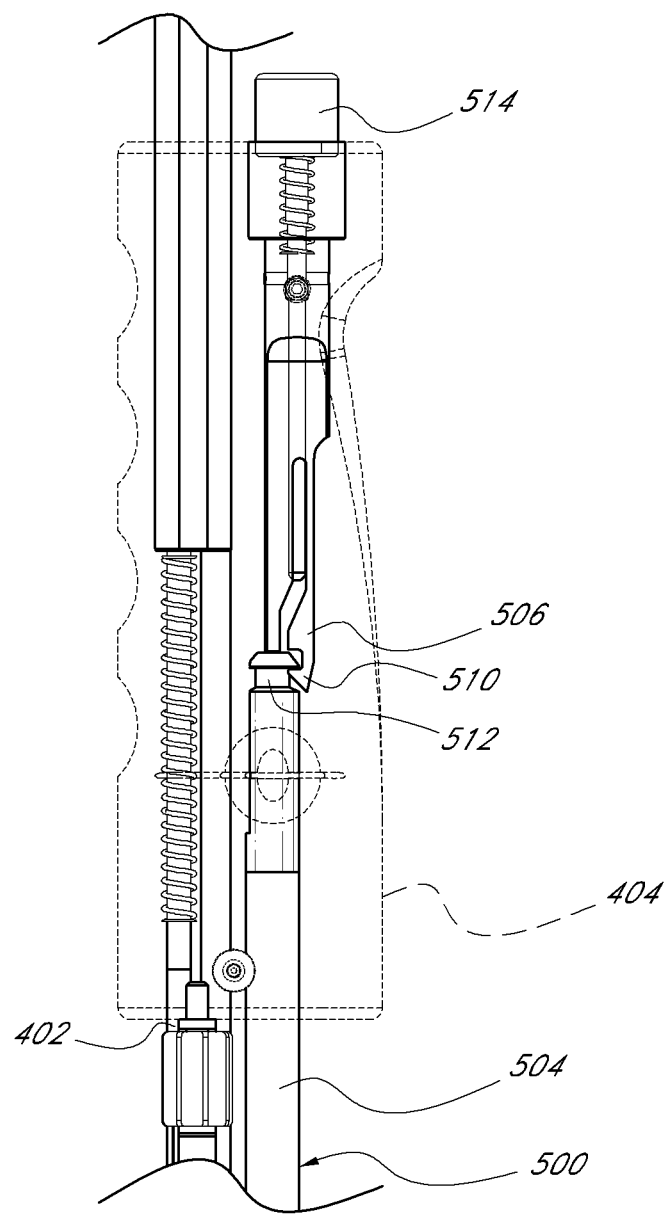
FIG. 61E illustrates the internal components of the handle in FIGS. 61A to 61D.
Figure 62A:
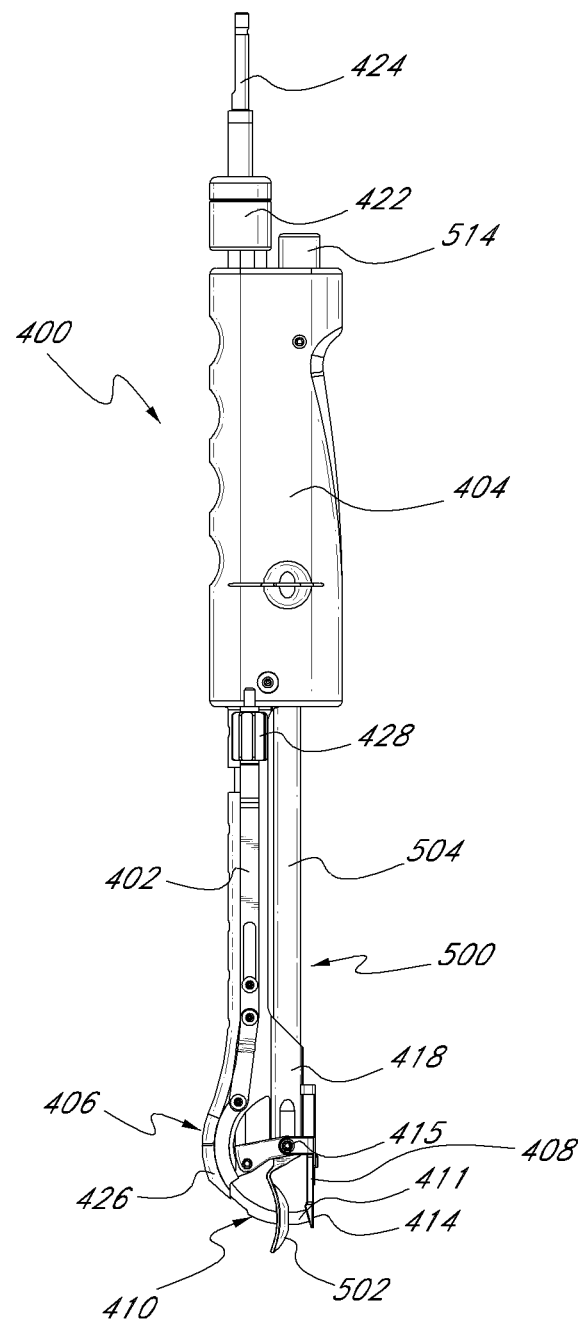
Figure 63B:
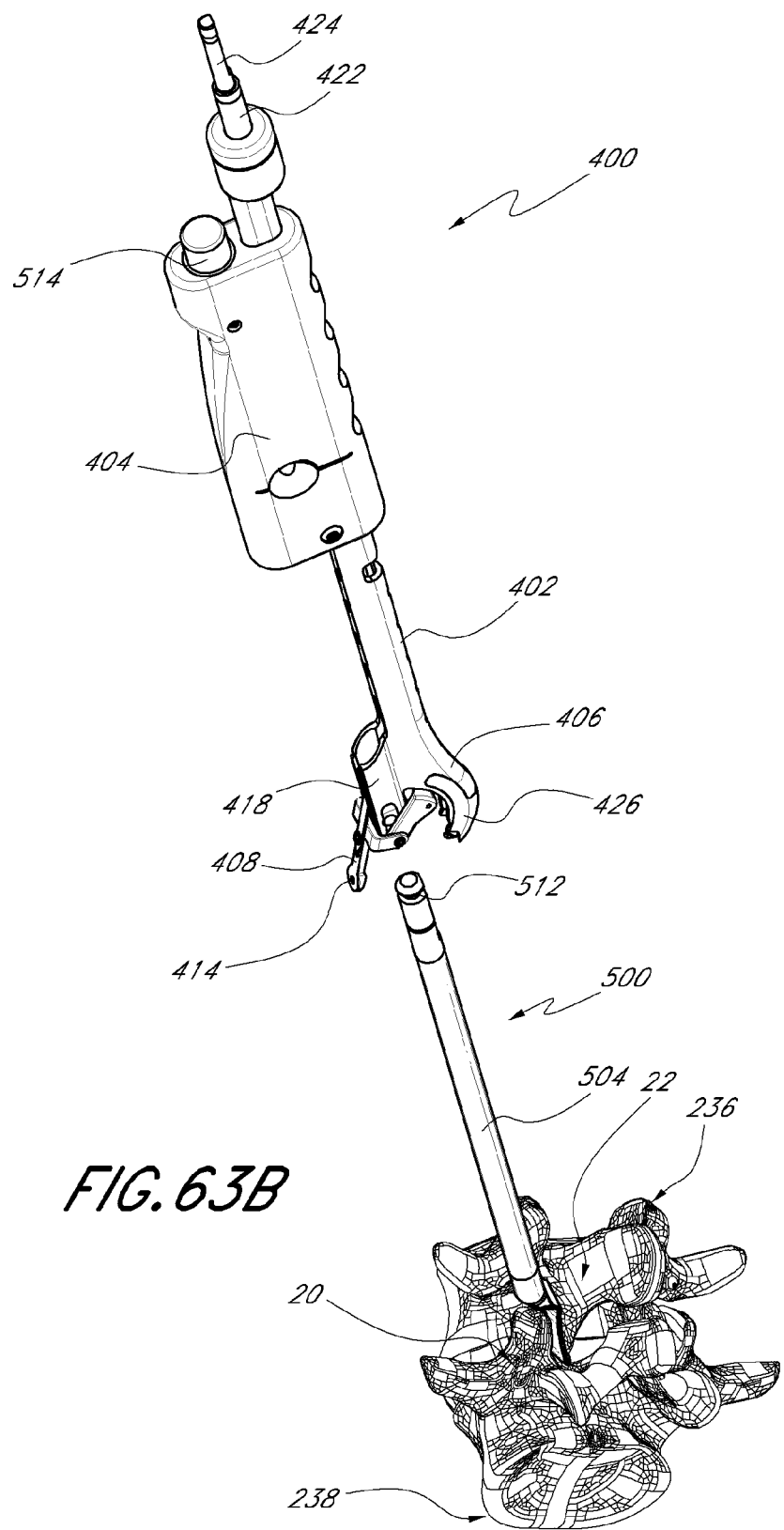
Figure 63C:
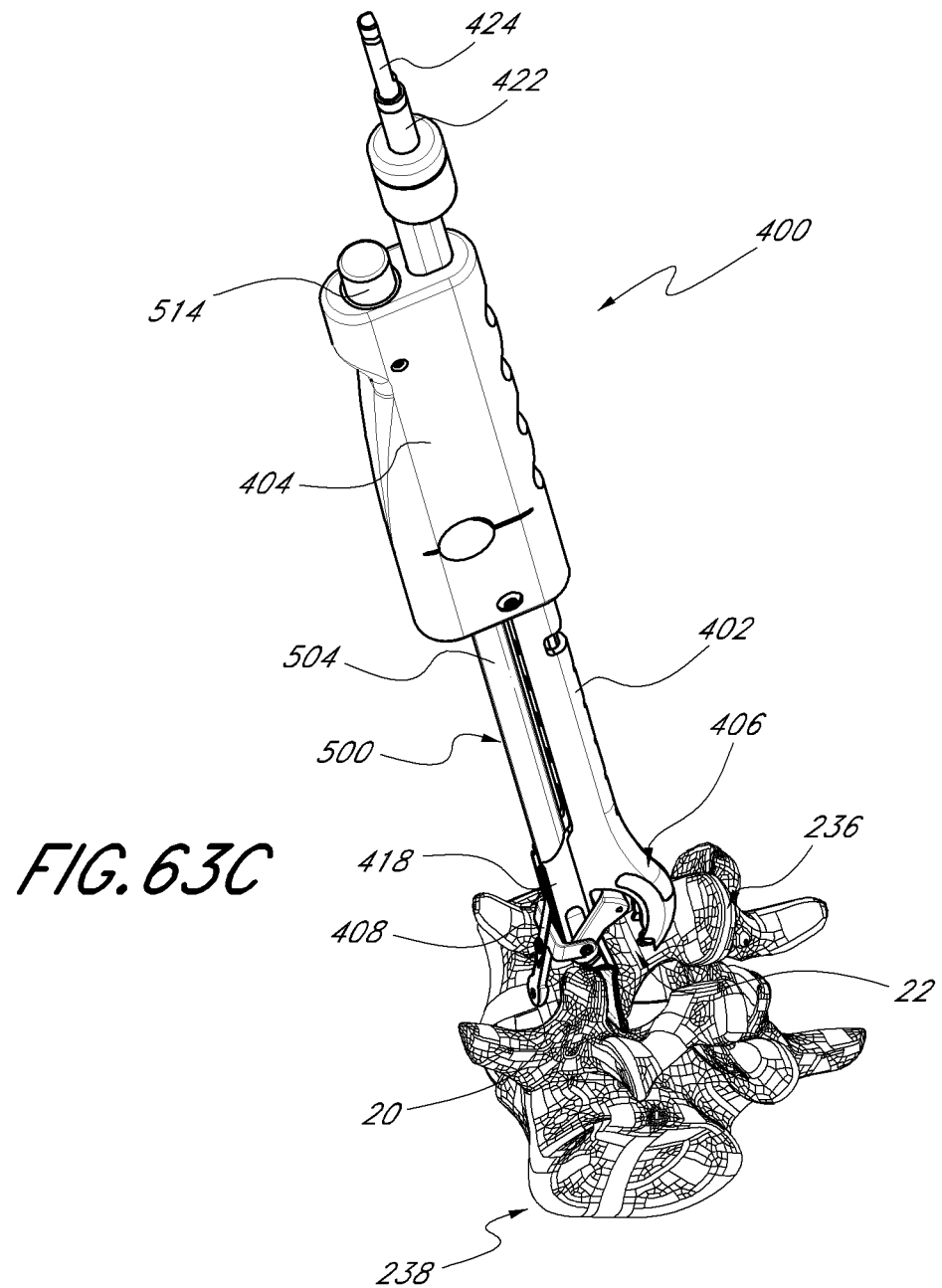
Figure 63D:
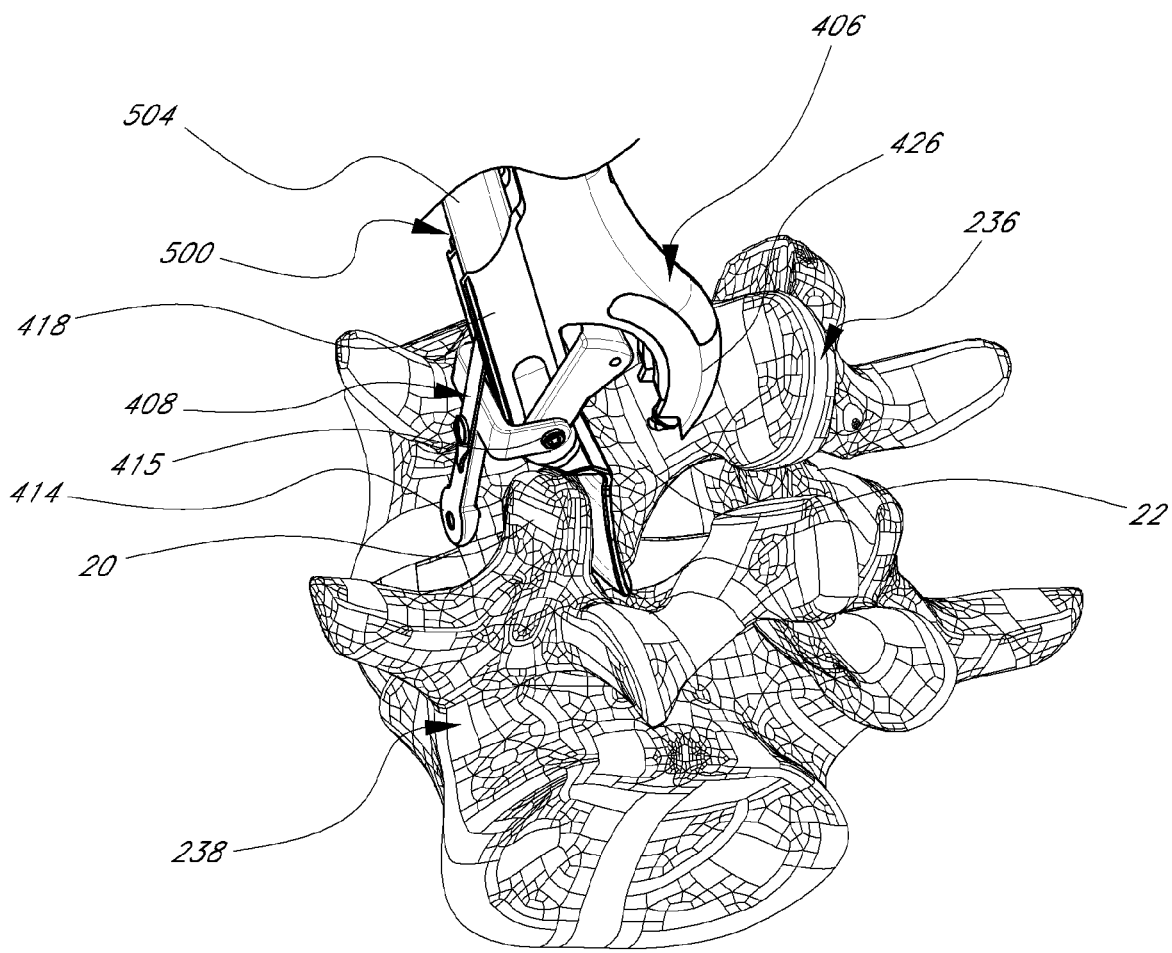

Referring to FIGS. 62A to 62B, the lumen-forming arm 410 can be slideably contained within the shaft 402 and arm guide 406. The lumen-forming arm 410 can be moved between an advanced configuration, depicted in FIG. 62A, and a retracted configuration, depicted in FIG. 61B, by a proximal actuator 422 that moves the lumen-forming arm 410 axially along the shaft 402 of the tool 400. In the embodiment depicted in FIGS. 61A-62B, manipulation of the actuator 422 causes a longitudinal movement of the lumen-forming arm 410. In some embodiments, the actuator 422 can be connected to the lumen-forming arm 410 directly, in which case the actuator 422 is also manipulated by pushing and pulling. In other embodiments, the actuator 422 can be connected to the lumen-forming arm 410 through mechanisms such as gears or hinges, wherein manipulation of the actuator 422 translates into longitudinal movement of the lumen-forming arm 410. The lumen-forming arm 410 can be straight or curved or a combination of these shapes. Different curved shapes of the arm are possible. In other embodiments, the lumen-forming arm 410 can have at least one straight segment and at least one curved segment. In the illustrated embodiment, the lumen-forming arm 410 is shaped to have a curved distal portion that has a desired arc so that the lumen-forming arm 410 follows a specified path when extended. The lumen-forming arm 410 may be stiff, bendable, or partially stiff and partially bendable. In preferred embodiments, the lumen-forming arm 410 is sufficiently stiff such that the distal portion is biased in the desired arc shape. In still other embodiments, a power source may be provided for hydraulic, pneumatic or other power-assisted manipulation of the lumen-forming arm 410.

The lumen-forming arm 410 can comprise a tubular cover 411 with a rotating drill bit 412 disposed coaxially within the tubular cover's 411 central lumen, as illustrated in FIG. 62B. The rotating drill bit 412 can be flexible and can be guided by the tubular cover 411, which as described previously can have sufficient rigidity to guide the flexible rotating drill bit 412 into the shape of the desired facet lumen. When the rotating drill bit 412 is described as flexible, it should be understood that in some embodiments the drill bit 412 can bend in the lateral direction, such that it can create a curved cutting path. In some embodiments, the lumen-forming arm 410 can comprise a rotating drill bit 412 without a tubular cover 411. In these embodiments, the rotating drill bit 412 is preferably at least partially rigid and biased in the shape of the desired facet lumen so that the drill bit 412 can form the desired shaped lumen.

In some embodiments, the lumen-forming arm 410 can be sized to be able to pass through the articular processes of the spine and the resulting hole is sized for a prosthesis retainer to be inserted. The lumen-forming arm 410 can have a diameter in the range of about 1 mm to 5 mm, preferably about 2 mm to 4 mm, and most preferably about 3 mm. At an end of the rotating drill bit 412 can be a drill bit tip 413 with a cutting surface for creating the lumen in the facets. The rotating drill bit tip 413 can be of any appropriate configuration and with any number of points. In some embodiments, the lumen-forming tip 413 may be round, flat, beveled or stepped. In some embodiments, the cutting surface can comprise any configuration that is known in the art for cutting through bone.

The rotating drill bit 412 can be connected to a drill coupler 424 to provide the axial rotation. The drill coupler 424 can have a configuration that is complementary to a coupling of a hand or powered drill. In some embodiments, the drill coupler 424 can have a feature to provide an anti-rotational connection with the coupling on the drill, such as for example a flat surface, or a shaft having a square or hexagonal cross-section. In some embodiments, the drill coupler 424 can have a configuration to fit with a standard drill chuck. In other embodiments, the drill coupler 424 can have any other configuration that is complementary to a coupling on a drill.

A target member 408 having a target plate 414 can be connected to the frame 418. The target plate 414 is in the path of travel of the lumen forming arm 410 and thus the position of the target plate 414 against an articular process can provide indication to the user of where the lumen forming arm 410 will emerge from the articular processes during the drilling procedure. The target member 408 can advantageously help the user avoid neural or other structures in and around the articular processes by visualizing and understanding the trajectory of the lumen forming arm 410 through the articular processes. In some embodiments, the target member 408 can provide some stabilization of the articular processes as the lumen forming arm 410 passes or cuts through the bone. The target plate 414 can be flat or curved. In some embodiments, the target plate 414 can have a concave or convex configuration. The target plate 414 can comprise an aperture 416, depicted in FIG. 61D, to seat the articular process and/or to allow at least a portion of the lumen-forming arm 410 of the arm guide 406 to penetrate through the bone and through the aperture 416. The target member 408 can also comprise a textured surface to resist slippage, including but not limited to serrations, ridges or indentations, or comprise a slip-resistant material. In some embodiments, as depicted in FIG. 61A, the lumen-forming tool 400 comprises a movable target member 408. The movable target member 408 may be connected by any of a variety of movable joints known in the art. For example, in the embodiment depicted in FIG. 61A, the target member 408 is connected to rest of the lumen-forming tool 400 with pivot pins 415. Various other attachment means include, but are not limited to, welding, brazing, gluing, cementing, pin, hinge, and ball and socket. The movable target member 408 allows increased conformance or adjustment of the tool 400 against the articular processes. In some embodiments, the movable target member 408 pivots passively as the tool 400 is applied to the bone. In other embodiments, the position or orientation of the movable target member 408 can be controlled at the proximal end of the tool 400. Manipulation of the plate may be performed using push/pull rods, gears pull wires or combinations thereof, as is known to those of skill in the art. The plate may be biased in a particular orientation using springs or other biasing structures.

The tool 400 can further comprise a spacing member 500 that can be coupled to the handle 404, as illustrated in FIG. 61E. The spacing member 500 can comprise a spacing member shaft 504 that is connected to a retention member 506 at the proximal end and has a spacer 502 at the distal end. The spacer 502, in turn, can comprise a disk-like member and a spacer aperture 508 that is lined up with the lumen-forming arm 410 to allow the drill bit tip 413 of the lumen-forming arm 410 to penetrate through the bones and through the aperture 508. The spacer 502 can have a curved or cupped shape to facilitate positioning between the articular processes 20 and 22. In some embodiments, the spacer 502 may have different shapes, sizes and thicknesses for use with different sized vertebra.

Preferably, the retention member 506 allows the spacing member 500 to be detached from and attached to the facet drill tool 400 with ease. In the embodiment illustrated in FIG. 61E, the retention member 506 is disposed inside the proximal handle 404 and comprises a hook 510 that can engage with a notch 512 on the proximal end of the spacing member shaft 504 to secure the spacing member 500 to the tool 400. The hook 510 can have a tapered distal surface such that it automatically engages with the notch 512 when the spacing member shaft 504 is inserted proximally into the handle 404. A release button 514 can be disposed on the proximal handle 404 that disengages the hook 510 from the notch 512 when depressed, releasing the spacing member 500. Although an embodiment of the retention member 506 is described herein, it is to be understood that any of a variety of retention mechanisms capable of easily attaching and detaching the spacing member 500 and tool 400 are also envisioned, including clamps, clips, ties, pins, adhesives and other structures that will be apparent to those of skill in the art in view of the disclosure herein.

Although the tool 400 depicted in FIGS. 61A to 62B have a generally straight spacing member 500, a person skilled in the art would understand that the spacing member shaft 504 or the connection between the spacing member shaft 504 and the spacer 502 can be modified to have a bend, corner or curvature to position the spacer 502 for placing between the articular processes 20, 22 and for lining up with the lumen-forming members. For example, in an alternative embodiment, the spacing member 500 can be disposed laterally adjacent the shaft 402 and may be configured such that the spacer 502 bends toward the arm guide 406, so the spacer aperture 508 or indentations on the disk-like member of the spacer 502 are aligned with the path of the lumen-forming arm 410.

In some embodiments, the spacer member 500 can rotate about its longitudinal axis while coupled to the tool 400 to accommodate variations in the shapes and positions of the articular processes 20, 22, as illustrated in FIG. 62B. The spacer aperture 508 is sufficiently large to allow the lumen-forming arm 410 to pass through the aperture 508 even when the spacer member 500 is at an angle to the lumen-forming arm 410.

Referring to FIGS. 63A to 66, a method of use for the tool 400 can comprise inserting the spacing member 500 in the patient and positioning the spacer 502 in the facet joint space between the articular processes 20, 22. The tool 400 can be guided over the spacing member shaft 504 until the hook 510 in the proximal handle 404 engages with the notch 512 on the spacing member 500 to lock the spacing member 500 to the tool 400, as illustrated in FIGS. 63B and 63C. Referring to FIGS. 63A to 66, the tool 400 may be used by positioning the drill bit tip 413 against one articular process 22 and positioning the target plate 414 against the corresponding articular process 20. FIG. 63D is a close-up of the distal portion of the tool 400 in position around articular processes 20, 22 and illustrating the arm guide 406, target plate 414 and the spacer 502. The tool 400 can be rotated axially relative to the spacing member 500 to adjust for variations in the native anatomy of the articular processes 20, 22. The surgeon may select a particular rotational and/or angular approach to the surgical site, depending upon the particular vertebral morphology of the patient, the extent and location of damage or injury, prior surgery, and other factors known in the art. When the tool 400 is actuated, the drill bit tip 413 cuts through both articular processes 20, 22 toward the target plate 414 of the opposing target member 408.

Figure 64A:
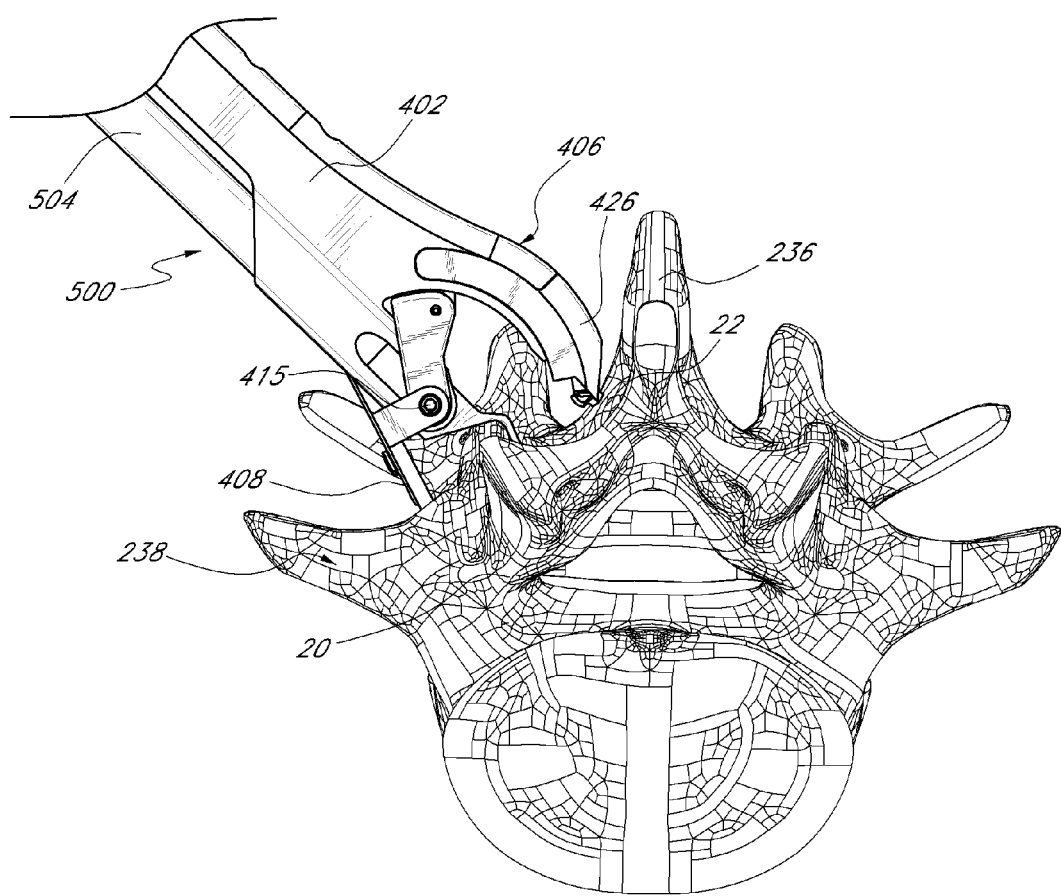
FIGS. 64A and 64B illustrate sequential schematic representations of the use of the tool in FIGS. 61A to 61D to secure the tool to the articular processes of the vertebrae.
Figure 64B:
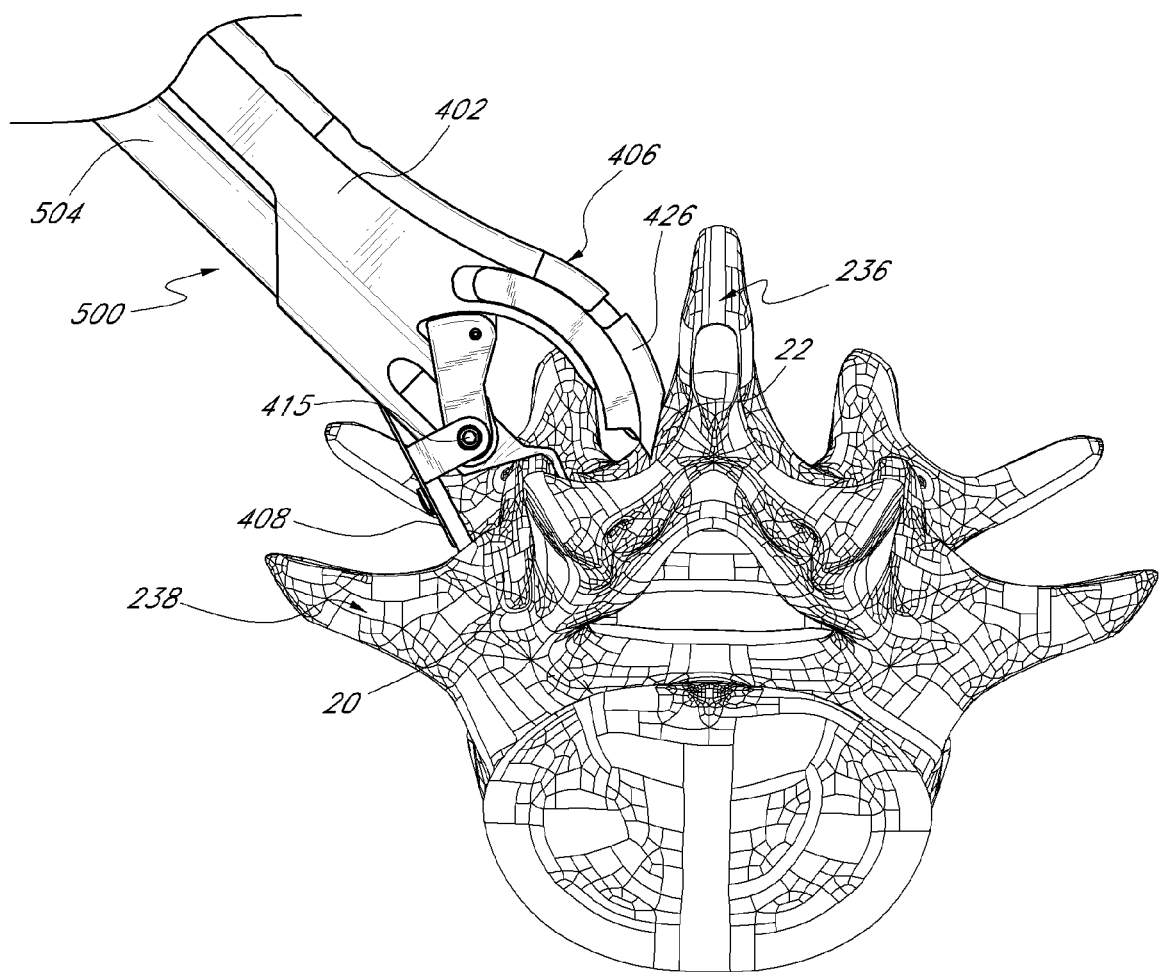

With reference to FIG. 64A, the arm guide 406 can be placed against an exposed articular process 22 of a superior vertebra 236, placing the opposing target member 408 against the corresponding articular process 20 of the inferior vertebra 238. FIG. 64A depicts one approach to the articular processes 20, 22 that may be used with the tool 400. In some embodiments, the target member 408 can be applied to the articular process 20 of the inferior vertebra 238, but in other embodiments, the target member 408 may be applied to the articular process 22 of the superior vertebra 236. The spacer 502 of the spacing member 500 is disposed in the facet joint space between the two articular processes.

The tool 400 can be adjusted so that a movable member of the tool 400 can secure to the outside of a facet joint or lamina. In the illustrated embodiment of FIG. 64B, the anchor portion 426 of the arm guide 406 is movable and has a pointed tip to secure to the facet 22. The tool 400 can have an arm guide adjustor 428 that can be actuated to extend and/or retract the anchor portion 426 of the arm guide 406.

Figure 65A:
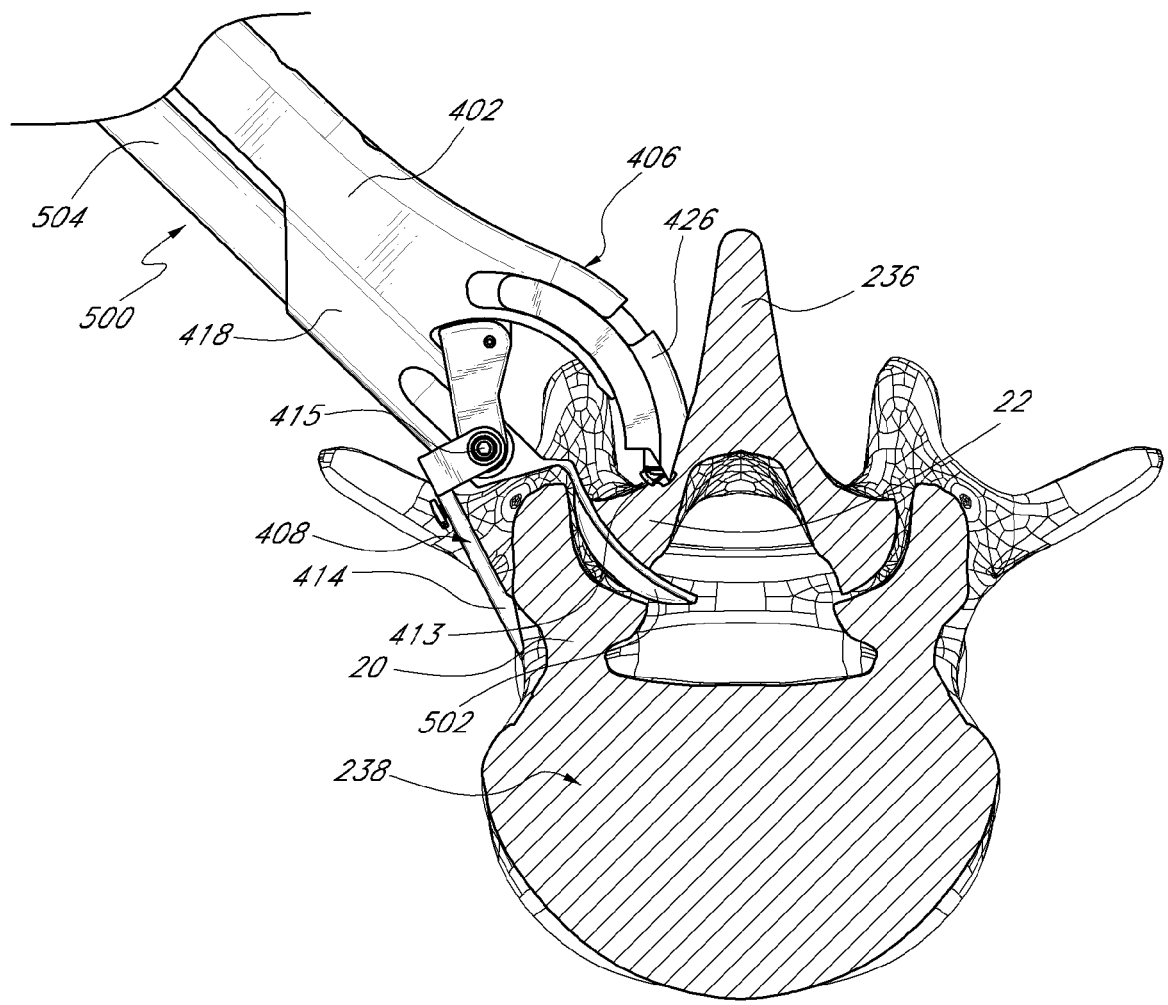
FIGS. 65A to 65D illustrate sequential schematic representations of the use of the tool in FIGS. 61A to 61D to create a hole in the articular processes of the vertebrae.
Figure 65B:
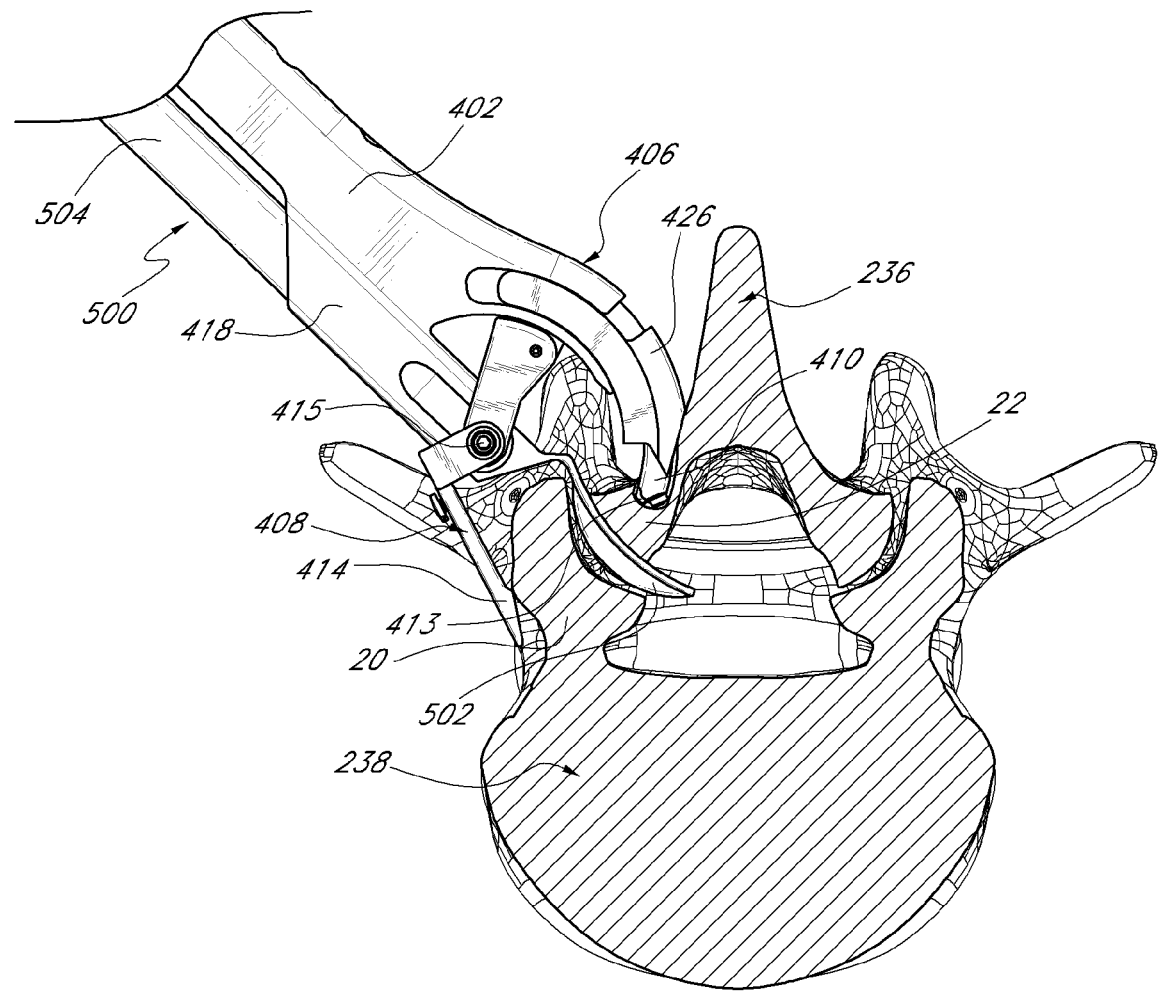
Figure 65C:
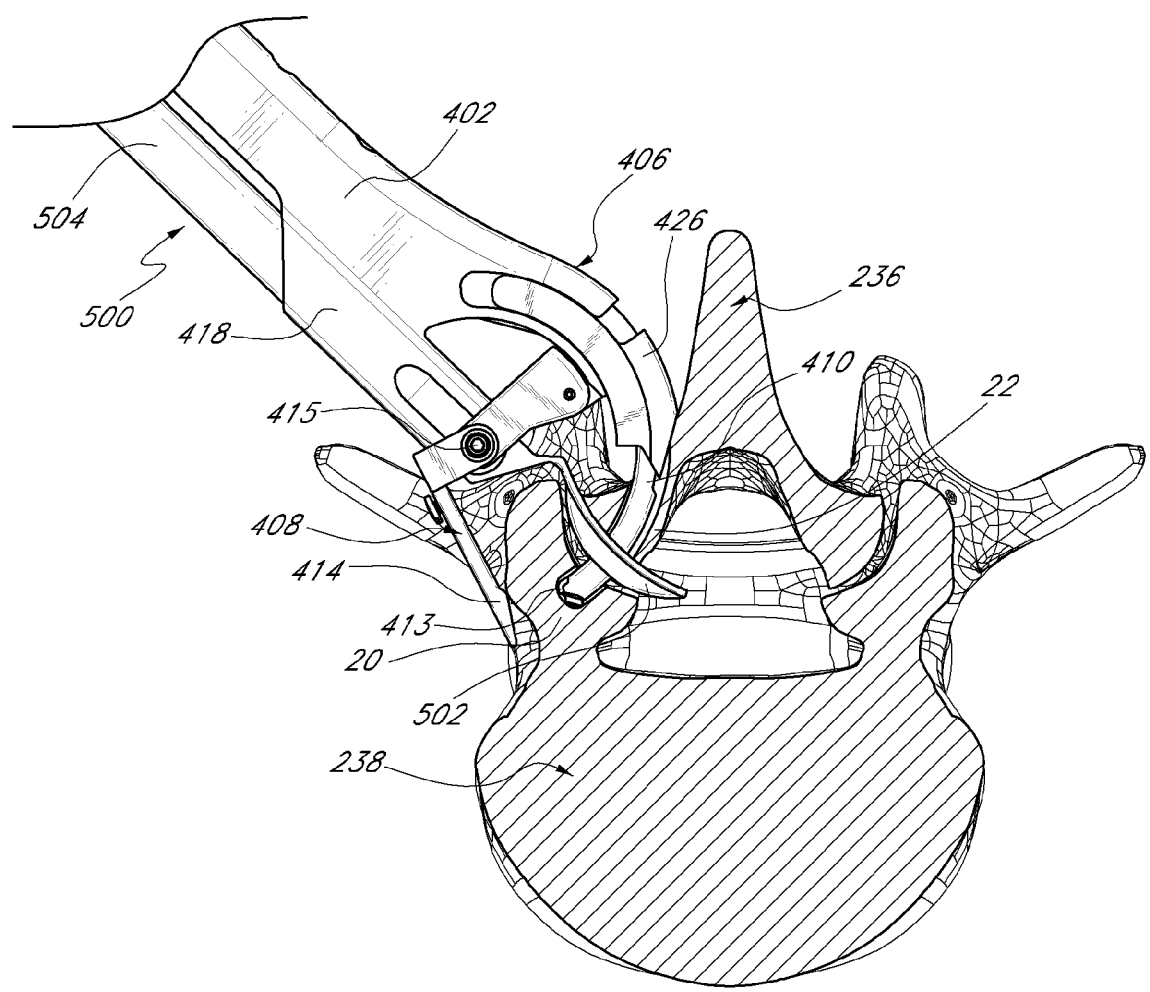
Figure 65D:
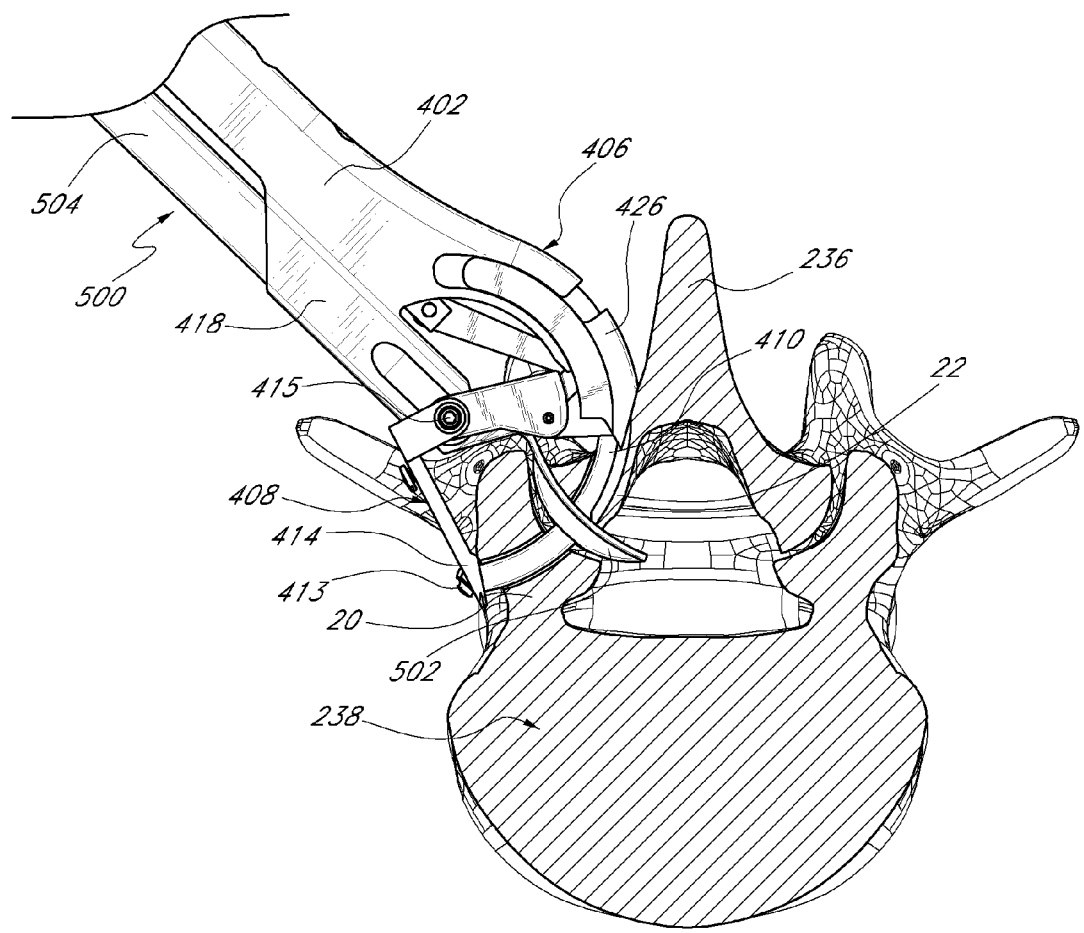
Figure 66:
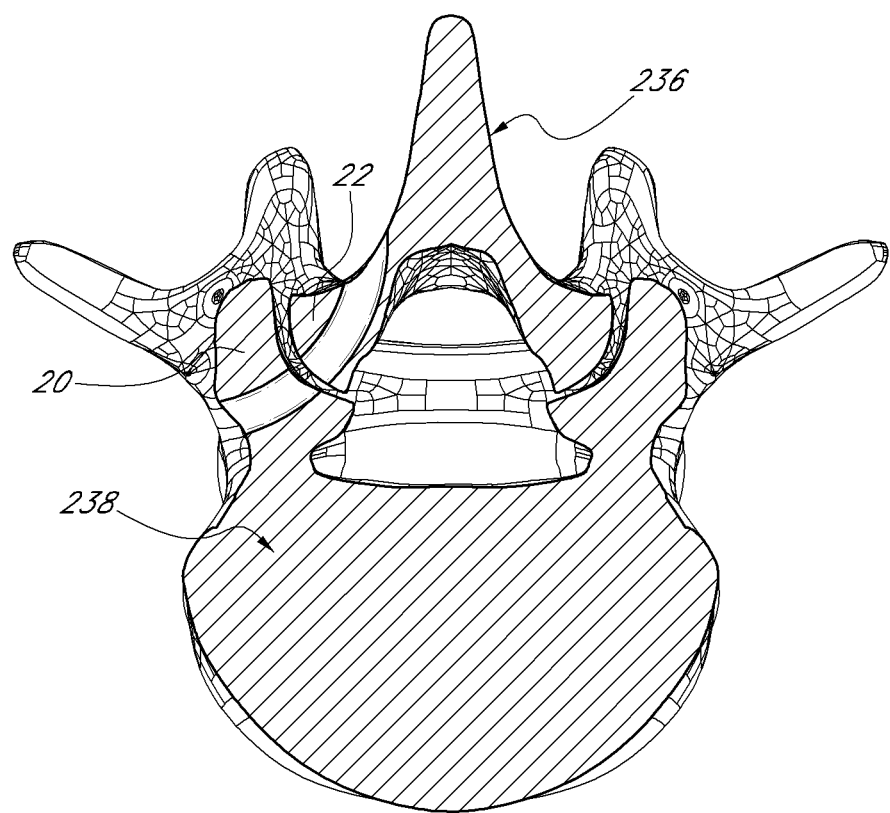
FIG. 66 illustrates a hole created in the articular processes of the vertebrae by the tool in FIGS. 61A to 61D.

A drill motor can be attached to the drill coupler 424 to power the rotating drill bit 412 within the lumen-forming arm 410. While the drill motor rotates the drill bit 412, the proximal actuator 422 can be advanced in the distal direction to extend the lumen-forming arm 410 from the arm guide 406 and form a hole in the articular processes 20, 22, as illustrated in the cross-sectional views of FIGS. 65A-65D. In some embodiments, the shape of the distal portion of the lumen-forming arm 410 is curved, as described above, to create a curved hole in the articular processes 20, 22. As illustrated in the embodiment of FIG. 65A, the anchor portion 426 of the arm guide 406 can extend and secure to the articular process 22. Then the lumen-forming arm 410 with the rotating drill bit 412 and the drill bit tip 413 can be extended to cut the lumen in the articular processes 20, 22, as illustrated in FIG. 65B. With reference to FIG. 65C, the lumen-forming arm 410 can extend through the spacer aperture 508. Then the lumen-forming arm 410 can continue to extend to the target plate 414 of the opposing target member 408, as illustrated in FIG. 65D.

Once the curved hole is formed, the lumen-forming arm 410 can be retracted by pulling the proximal actuator 422 in the proximal direction. Methods of using the resulting holes to anchor or stabilize facet joint prosthesis, and also altering the spacing and motion at the facet joints of the vertebral column, are provided above.

Figure 67:
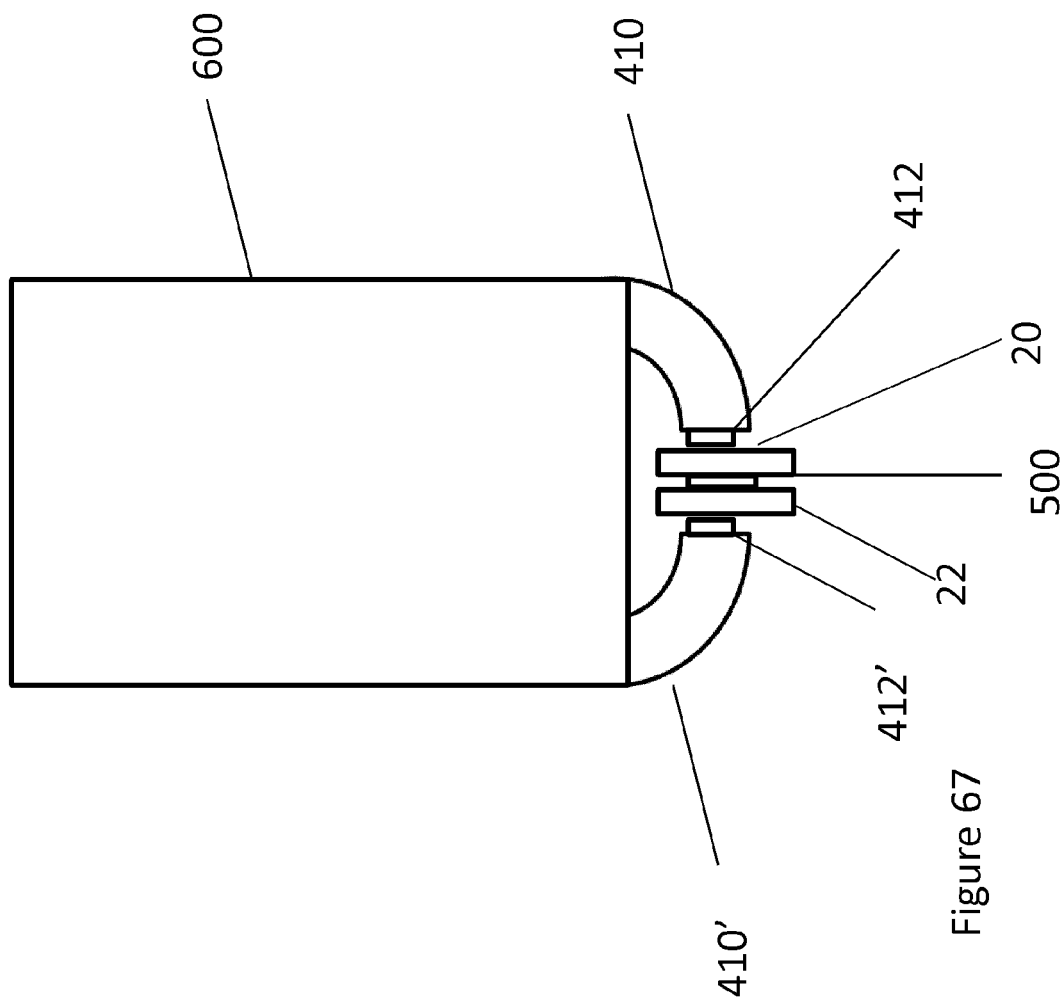
FIG. 67 shows one embodiment of the tool with dual-lumen forming arms.

In another embodiment (shown schematically in FIG. 67), the tool 600 can comprise dual lumen-forming arms 410, 410' that can extend toward each other in a pincher-like fashion, similar to the dual-arm tool 232 described above. Each lumen-forming arm 410, 410' can comprise rotating drills 412, 412' that are connected to two separate drill motors or a common drill motor. One of skill in the art will understand that in some embodiments, only one lumen-forming arm may move at a time while the other arm is fixed in position. In other embodiments of the lumen-forming tool, the two arms may move asymmetrically. In some embodiments, both lumen-forming arms may move at the same time until they meet at an intermediate position. The movement of both lumen-forming arms typically occurs in the same plane, but in other embodiments, the movement of each arm may occur in different planes that intersect at the intermediate position.

In some embodiments, the disk-like member of the spacer may have indentations on each side of the disk-like member instead of a spacer aperture, and the indentations can be lined up or aligned with the lumen-forming arms to allow the drill tips to penetrate through the bones and into the indentations. In embodiments where the spacer has a hole instead of indentations, the lumen-forming tips moves until they meet at an intermediate position to form a curved or non-linear passageway through the articular processes 20, 22.

The size of the tool is appropriate for drilling the particular bone in the way that is desired. Smaller devices can be used for smaller vertebra and larger devices for larger vertebra. In addition, the device can be use on bones other than the vertebra and on bones for humans and non-humans. Other applications of the tool are for creating anchor points in bone for sutures and for bone immobilization such as with pins.

Other means of attaching the actuator to the inner shaft or other movement-transmitting member such that a movement of the actuator results in a desired corresponding movement of the inner shaft are possible and are considered within the scope of the invention.

The tool can be made of any appropriate material for the particular part. Exemplary materials include, but are not limited to, stainless steel, surgical steel, cutlery steel, tool steel, cobalt and its alloys, nickel and its alloys, chromium and its alloys, titanium and its alloys, zirconium and its alloys, aluminum and its alloys, magnesium and its alloys, polymers, elastomers, and ceramics. Ceramics may include, but are not limited to silicon carbide, silicon oxide(s), silicon nitride, aluminum oxide, alumina, zirconia, tungsten carbide, other carbides.

Other embodiments of the invention comprise a method of forming a passageway in the articular processes of the vertebra using a facet lumen-forming tool described herein. The method may comprise placing the lumen-forming tips of the facet lumen-forming against a pair of articular processes of the vertebra, and actuating the lumen-forming member(s). Another embodiment may comprise placing the lumen-forming tip and plate of the single-arm facet lumen-forming against the articular processes of the vertebra, and actuating the lumen-forming.

A further embodiment of the invention is a method of anchoring or restraining a prosthesis between the facet joints of the vertebra comprising forming a curved lumen through the articular processes with the facet lumen-forming tool described herein, positioning a facet joint implant into the facet joint associated with the articular processes and inserting an anchoring member through the curved lumen.

While embodiments of this invention have been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method for forming a through lumen in a first articular process of a vertebral facet joint, comprising:
   accessing the first articular process;
   positioning a spacer having a spacer aperture between a first articulating surface of the first articular process and a second articulating surface of a second articular process;
   positioning a lumen-forming arm comprising a drill bit against an outside surface of the first articular process;
   rotating the drill bit by coupling a rotational power source to the drill bit; and
   manipulating the lumen-forming arm through the first articular process to penetrate a the first articulating surface of the first articular process and pass through the spacer aperture, forming the through lumen.

2. The method of claim 1, further comprising positioning a target member against an outside surface of the second articular process of the vertebral facet joint during the movement of the lumen-forming arm.

3. The method of claim 1, wherein the through lumen is non-linear.

4. The method of claim 1, wherein the through lumen is curved.

5. The method of claim 1, wherein the through lumen is curved toward a base of the first articulating surface of the first articular process.

6. The method of claim 1, further comprising:
   positioning a second lumen-forming arm comprising a second drill bit against the second articular process of the vertebral facet joint;
   rotating the second drill bit; and
   manipulating the first lumen-forming arm and the second lumen-forming arm through the first articular process and second articular process to form a through lumen through the first articular process and second articular process.

7. The method of claim 1, further comprising inserting an anchoring member through the through lumen.

8. The method of claim 7, further comprising positioning a facet joint implant into the vertebral facet joint.

9. The method of claim 6, further comprising inserting an anchoring member through the through lumen.

10. The method of claim 9, further comprising positioning a facet joint implant into the vertebral facet joint.

11. The method of claim 1, further comprising:
    securing an anchor portion of a movable arm guide to the outside surface of the first articular process; and
    placing the lumen-forming arm through the movable arm guide.

12. The method of claim 2, further comprising manipulating the lumen forming arm through the second articular process to form a through lumen in the second articular process.

13. The method of claim 1, further comprising positioning a facet joint implant to restore a distance between the first articulating surface of the first articular process and the second articulating surface of the second articular process.

14. The method of claim 1, further comprising aligning the lumen forming arm with the hole prior to manipulating the lumen-forming arm through the first articular process to penetrate the hole.

15. The method of claim 1, wherein the spacer includes a disc-like member.

16. The method of claim 1, wherein the first surface of the spacer is configured to abut the first articulating surface of the first articular process and the second surface of the spacer is configured to abut the second articulating surface of the second articular process.

17. The method of claim 1, further comprising:
   removing the spacer; and
   inserting a facet joint implant between the first articular process and the second articular process of the vertebral facet joint.

18. A method for forming a through lumen in a first articular process and a second articular process of a vertebral facet joint, comprising:
   accessing the first articular process and the second articular process;
   placing a spacer between the first articular process and second articular process;
   positioning a first lumen-forming arm comprising a drill bit against a first, outside surface of the first articular process;
   rotating the drill bit by coupling a rotational power source to the drill bit;
   positioning a second lumen-forming arm comprising a second drill bit against a second articular process of the vertebral facet joint;
   rotating the second drill bit; and
   manipulating the first lumen-forming arm and the second lumen-forming arm through the first articular process and second articular process to form a through lumen through the first articular process and second articular process;
   wherein the first lumen-forming arm penetrates the first articular process and into a first surface of the spacer and the second lumen-forming arm penetrates the second articular process and into a second surface of the spacer.

19. A method for forming a through lumen in a first articular process of a vertebral facet joint, comprising:
   accessing the first articular process;
   positioning a spacer between the first articular process and a second articular process of the vertebral facet joint;
   positioning a lumen-forming arm comprising a drill bit against a first, outside surface of the first articular process;
   rotating the drill bit by coupling a rotational power source to the drill bit;
   manipulating the lumen-forming arm through the first articular process to penetrate a second, facet joint surface of the first articular process, forming the through lumen; and
   manipulating the lumen-forming arm through a hole in the spacer and through the second articular process to form a through lumen in the second articular process.

* * * * *

UNITED STATES PATENT AND TRADEMARK OFFICE
CERTIFICATE OF CORRECTION

| | | |
|---|---|---|
| PATENT NO. | : 8,992,533 B2 | Page 1 of 1 |
| APPLICATION NO. | : 12/859009 | |
| DATED | : March 31, 2015 | |
| INVENTOR(S) | : Jason Daniel Blain | |

It is certified that error appears in the above-identified patent and that said Letters Patent is hereby corrected as shown below:

Title Page

In column 2 (page 1, item 56) at line 15, Under Other Publications, change "tecnhique;" to --technique;--.

Claims

In column 28 at line 15 (approx.), In Claim 1, change "a the" to --the--.

In column 28 at line 54, In Claim 12, change "lumen forming" to --lumen-forming--.

Signed and Sealed this
Fifth Day of January, 2016

Michelle K. Lee
*Director of the United States Patent and Trademark Office*